(12) United States Patent
Hirano et al.

(10) Patent No.: US 12,240,886 B2
(45) Date of Patent: Mar. 4, 2025

(54) PEPTIDE-HLA COMPLEXES AND METHODS OF PRODUCING SAME

(71) Applicant: University Health Network, Toronto (CA)

(72) Inventors: Naoto Hirano, Toronto (CA); Munehide Nakatsugawa, Sapporo (JP); Muhammed Aashiq Rahman, Brisbane (AU); Kenji Murata, Toronto (CA)

(73) Assignee: University Health Network, Toronto (CA)

( * ) Notice: Subject to any disclaimer, the term of this patent is extended or adjusted under 35 U.S.C. 154(b) by 41 days.

(21) Appl. No.: 17/814,401

(22) Filed: Jul. 22, 2022

(65) Prior Publication Data

US 2023/0192809 A1 Jun. 22, 2023

Related U.S. Application Data

(62) Division of application No. 16/095,913, filed as application No. PCT/CA2017/000102 on Apr. 27, 2017, now Pat. No. 11,396,536.

(60) Provisional application No. 62/328,325, filed on Apr. 27, 2016.

(51) Int. Cl.
| | |
|---|---|
| *A61K 39/00* | (2006.01) |
| *A61K 39/12* | (2006.01) |
| *A61K 39/395* | (2006.01) |
| *A61K 47/64* | (2017.01) |
| *C07K 7/06* | (2006.01) |
| *C07K 14/74* | (2006.01) |
| *C07K 16/28* | (2006.01) |
| *C12N 5/0783* | (2010.01) |
| *C12N 5/0784* | (2010.01) |

(52) U.S. Cl.
CPC .... *C07K 14/70539* (2013.01); *A61K 39/4611* (2023.05); *A61K 39/4632* (2023.05); *A61K 39/464488* (2023.05); *A61K 39/464491* (2023.05); *C07K 7/06* (2013.01); *C12N 5/0638* (2013.01); *C12N 5/0639* (2013.01); *C07K 2319/02* (2013.01); *C07K 2319/21* (2013.01)

(58) Field of Classification Search
CPC .......... A61P 35/00; A61P 37/04; A61P 43/00; A61P 37/02; A61K 39/00
See application file for complete search history.

(56) References Cited

U.S. PATENT DOCUMENTS

2003/0124613 A1 7/2003 Hildebrand et al.
2010/0168390 A1 7/2010 Brix et al.

FOREIGN PATENT DOCUMENTS

CN 101687910 A 3/2010
WO WO-2017185169 A1 11/2017

OTHER PUBLICATIONS

Allard, M., et al., "Soluble HLA-I/Peptide Monomers Mediate Antigen-Specific CD8 T Cell Activation through Passive Peptide Exchange with Cell-Bound HLA-I Molecules," The Journal of Immunology 192(11):5090-5097, The American Association of Immunologists, Inc., United States (Jun. 2014).
Altman, J., et al., "Phenotypic analysis of antigen-specific T lymphocytes," Science 274(5284):94-96, American Association for the Advancement of Science, United States (Oct. 1996).
Bakker, A., et al., "Conditional MHC class I ligands and peptide exchange technology for the human MHC gene products HLA-A1, -A3, -A11, and -B7," Proc Natl Acad Sci, 105(10):3825-3830, National Academy of Sciences, United States (Mar. 2008).
Butler, M., et al., "A panel of human cell-based artificial APC enables the expansion of long-lived antigen-specific CD4+ T cells restricted by prevalent HLA-DR alleles," Int Immunol 22(11):863-873, Oxford University Press, United Kingdom (Nov. 2010).
Butler, M., et al., "Long-lived antitumor CD8+ lymphocytes for adoptive therapy generated using an artificial antigen-presenting cell," Clin Cancer Res 13(6):1857-1867, American Association for Cancer Research Inc., United States (Mar. 2007).
Chen, X., et al., "Fusion protein linkers: Property, design and functionality" Adv Drug Deliv Rev 65(10):1357-1369, Elsevier B.V., Netherlands (Oct. 2013).
Dolton, G., et al., "More tricks with tetramers: a practical guide to staining T cells with peptide-MHC multimers," Immunology 146(1):11-22, Wiley-Blackwell Publishing LTD., United Kingdom (Sep. 2015).
Feldman, S., et al., "Adoptive Cell Therapy—Tumor-infiltrating Lymphocytes, T-Cell Receptors, and Chimeric Antigen Receptors," Semin Oncol 42(4):626-639, W.B. Saunders, United States (Aug. 2015).
Hirano, N., et al., "Autoantibodies frequently detected in patients with aplastic anemia," Blood 102(13):4567-4575, Elsevier B.V., United States (Dec. 2003).
Hirano, N., et al., "Efficient presentation of naturally processed HLA class I peptides by artificial antigen-presenting cells for the generation of effective antitumor responses," Clin Cancer Res 12(10):2967-2975, American Association for Cancer Research Inc., United States (May 2006).

(Continued)

*Primary Examiner* — Barry A Chestnut
(74) *Attorney, Agent, or Firm* — Sterne, Kessler, Goldstein & Fox P.L.L.C.

(57) ABSTRACT

There is provided herein, the use of mammalian derived HLA class I molecule for in vitro peptide exchange. For example, there is provided a method of producing an HLA class I molecule complexed to a pre-selected peptide comprising: (a) providing a mammalian derived HLA class I molecule complexed to an existing peptide; (b) incubating, in vitro, the HLA class I molecule complexed to the existing peptide with the pre-selected peptide, wherein the pre-selected peptide is at a concentration sufficient to replace the existing peptide to produce the HLA class I molecule complexed to the pre-selected peptide; and the HLA class I molecule comprises α1, α2, α3 and β2m domains.

16 Claims, 33 Drawing Sheets

Specification includes a Sequence Listing.

(56) References Cited

OTHER PUBLICATIONS

Hirano, N., et al., "Engagement of CD83 ligand induces prolonged expansion of CD8+ T cells and preferential enrichment for antigen specificity," Blood, 107(4): 1528-1536, Elsevier B.V., United States (Feb. 2006).

Hirano, N., et al., "Identification of an immunogenic CD8+ T-cell epitope derived from gamma-globin, a putative tumor-associated antigen for juvenile myelomonocytic leukemia," Blood 108(8):2662-2668, Elsevier B.V., United States (Oct. 2006).

Imataki, O., et al., "IL-21 can supplement suboptimal Lck-independent MAPK activation in a STAT-3-dependent manner in human CD8(+) T cells," J Immunol 188(4):1609-1619, American Association of Immunologists, United States (Feb. 2012).

International Search Report and Written Opinion issued in International Patent Application No. PCT/CA2017/000102, dated Jul. 13, 2017, 9 pages.

Kagoya, Y., et al., "BET bromodomain inhibition enhances T cell persistence and function in adoptive immunotherapy models" J. Clin. Invest 126(9):3479-3494, The American Society for Clinical Investigation, United States (Sep. 2016).

Kawana-Tachikawa, A., et al., "An efficient and versatile mammalian viral vector system for major histocompatibility complex class I/ peptide complexes," Journal of Virology 76(23):11982-11988, American Society for Microbiology, United States (Dec. 2002).

Kawase, T., et al., "Alternative splicing due to an intronic SNP in HMSD generates a novel minor histocompatibility antigen," Blood 110(3):1055-1063, Elsevier B.V., United States (Aug. 2007).

Klenerman, P., et al., "Tracking T cells with tetramers: new tales from new tools," Nat Rev Immunol 2(4):263-272, Nature Publishing Group, United Kingdom (Apr. 2002).

Laugel, B., et al., "Different T cell receptor affinity thresholds and CD8 coreceptor dependence govern cytotoxic T lymphocyte activation and tetramer binding properties," J Biol Chem 282(33):23799-23810, American Society for Biochemistry and Molecular Biology Inc., United States (Aug. 2007).

Marrack, P., et al., "Evolutionarily conserved amino acids that control TCR-MHC interaction" Annu Rev Immunol 26:171-203, Annual Reviews Inc., United States (2008).

Migueles, S., et al., "HLA B*5701 is highly associated with restriction of virus replication in a subgroup of HIV-infected long term nonprogressors," Proc Natl Acad Sci U.S.A. 97(6):2709-2714, National Academy of Sciences, United States (Mar. 2000).

Nakatsugawa, M., et al., "Specific roles of each TCR hemichain in generating functional chain-centric TCR," J Immunol 194(7):3487-3500, American Association of Immunologists, United States (Apr. 2015).

Nguyen, L., et al., "Expansion and characterization of human melanoma tumor-infiltrating lymphocytes (TILs)," PLoS One 5(11):e13940, Public Library of Science, United States (Nov. 2010).

NIH Tetramer Core Facility, "Production Protocols—Class I MHC Tetramer Preparation: Overview," accessed at URL:[https://tetramer.yerkes.emory.edu/support/protocols] on May 21, 2021, 21 pages.

Ochi, T., et al., "Optimization of T-cell reactivity by Exploiting TCR Chain Centricity for the Purpose of Safe and Effective Antitumor TCR Gene Therapy," Cancer Immunol Res 3(9):1070-1081, American Association for Cancer Research Inc., United States (Sep. 2015).

Parker, K., et al., "Scheme for ranking potential HLA-A2 binding peptides based on independent binding of individual peptide side-chains," J Immunol 152(1):163-175, American Association of Immunologists, United States (Jan. 1994).

Robbins, P., et al., "Mining exomic sequencing data to identify mutated antigens recognized by adoptively transferred tumor-reactive T cells," Nat Med 19(6):747-752, Nature Publishing Group, United Kingdom (Jun. 2013).

Rodenko, B., et al., "Generation of peptide-MHC class I complexes through UV-mediated ligand exchange," Nature Protocols 1(3):1120-1132, Nature Publishing Group, United Kingdom (Aug. 2006).

Rossjohn, J., et al., "T cell antigen receptor recognition of antigen-presenting molecules," Annu Rev Immunol 33:169-200, Annual Reviews Inc., United States (Dec. 2014).

Saini, S., et al., "Dipeptides catalyze rapid peptide exchange on MHC class molecules," Proc Natl Acad Sci 112(1):202-207, National Academy of Sciences, United States (Jan. 2015).

Stevens, J., et al., "Efficient Generation of Major Histocompatibility Complex Class I—Peptide Complexes Using Synthetic Peptide Libraries," Journal of Biological Chemistry 273(5):2874-2884, Elsevier Inc. on behalf of American Society for Biochemistry and Molecular Biology, Netherlands (Jan. 1998).

Tanaka, M., et al., "Induction of HLA-DP4-restricted anti-survivin Th1 and Th2 responses using an artificial antigen-presenting cell," Clin Cancer Res 17(16):5392-5401, American Association for Cancer Research Inc., United States (Aug. 2011).

Truscott, S., et al., "Human Major Histocompatibility Complex (MHC) Class I Molecules with Disulfide Traps Secure Disease-related Antigenic Peptides and Exclude Competitor Peptides," Journal of Biological Chemistry 283(12):7480-7490, American Society for Biochemistry and Molecular Biology Inc., United States (Mar. 2008).

UniProt, "UniProtKB—Q16655 (MAR1_Human)" Nov. 1, 1997, URL <https://www.uniprot.org/uniprot/Q16655>.

Vitiello, A., et al., "Analysis of the HLA-restricted influenza-specific cytotoxic T lymphocyte response in transgenic mice carrying a chimeric human-mouse class I major histocompatibility complex," Journal of Experimental Medicine 173(4): 1007-1015, Rockefeller University Press, United States (Apr. 1991).

Wooldridge, L., et al., "Enhanced immunogenicity of CTL antigens through mutation of the CD8 binding MHC class I invariant region," Eur J Immunol 37(5): 1323-1333, Wiley-VCH Verlag, Germany (May 2007).

Wooldridge, L., et al., "MHC class I molecules with Superenhanced CD8 binding properties bypass the requirement for cognate TCR recognition and nonspecifically activate CTLs," J Immunol 184(7):3357-3366, American Association of Immunologists, United States (Apr. 2010).

Wooldridge, L., et al., "Tricks with tetramers: how to get the most from multimeric peptide-MHC," Immunology 126(2):147-164, Wiley-Blackwell Publishing Ltd., United Kingdom (Feb. 2009).

Non-Final Office Action mailed Aug. 30, 2021, in U.S. Appl. No. 16/095,913, Hirano, N., et al., filed Oct. 23, 2018, 9 pages.

NCBI, "Chain A, MHC Class I Histocompatibility Antigen (HLA-A*0201) (Alpha Chain)," PDB: 1AKJ_A, accessed at https://www.ncbi.nlm.nih.gov/protein/1AKJ_A/, 2 pages (May 1997).

| No. | Specimen Code. | HLA-A | HLA-B | HLA-C |
|---|---|---|---|---|
| 1 | M25 | 01:01/02:01 | 07:02/08:01 | 07:01/07:02 |
| 2 | M29 | 02:01/11:01 | 07:02/27:02 | 02:02/07:02 |
| 3 | M31 | 02:01/24:02 | 40:01/44:02 | 03:04/05:01 |
| 4 | M37 | 02:01/24:02 | 14:02/48:01 | 08:02/08:03 |
| 5 | M38 | 02:01/- | 15:01/44:02 | 03:03/05:01 |
| 6 | M40 | 02:01/30:02 | 18:01/45:01 | 05:01/06:02 |
| 7 | M66 | 02:01/32:01 | 07:02/27:05 | 02:02/07:02 |
| 8 | M69 | 02:01/03:01 | 08:01/14:02 | 07:01/08:02 |
| 9 | M96 | 01:01/02:01 | 08:01/51:01 | 07:01/15:02 |

Figure 15

| No. | Specimen Code | HLA-A | HLA-B | HLA-C | Positive A2 dimer Staining (>0.3%) | ELISPOT |
|---|---|---|---|---|---|---|
| 1 | M25 | 01:01/02:01 | 07:02/08:01 | 07:01/07:02 | Wild type MART-1<br>Heteroclitic MART-1 | +<br>+ |
| 2 | M29 | 02:01/11:01 | 07:02/27:02 | 02:02/07:02 | None | NT |
| 3 | M31 | 02:01/24:02 | 40:01/44:02 | 03:04/05:01 | Wild type NY-ESO-1<br>Heteroclitic NY-ESO-1 | +<br>+ |
| 4 | M37 | 02:01/24:02 | 14:02/48:01 | 08:02/08:03 | SSX-2 (41-) | + |
| 5 | M38 | 02:01/- | 15:01/44:02 | 03:03/05:01 | None | NT |
| 6 | M40 | 02:01/30:02 | 18:01/45:01 | 05:01/06:02 | SSX-2 (41-) | + |
| 7 | M66 | 02:01/32:01 | 07:02/27:05 | 02:02/07:02 | gp-100 (154-)<br>gp-100 (209-)<br>gp-100 (280-)<br>Wild type MART-1<br>Heteroclitic MART-1 | +<br>+<br>+<br>+<br>+ |
| 8 | M69 | 02:01/03:01 | 08:01/14:02 | 07:01/08:02 | None | NT |
| 9 | M96 | 01:01/02:01 | 08:01/51:01 | 07:01/15:02 | Wild type MART-1<br>Heteroclitic MART-1 | +<br>+ |

Figure 28

PEPTIDE-HLA COMPLEXES AND METHODS OF PRODUCING SAME

CROSS-REFERENCE TO RELATED APPLICATIONS

This application is a division of U.S. Nonprovisional application Ser. No. 16/095,913 filed 23 Oct. 2018, which is a national phase application under 35 U.S.C. § 371 of International Application No. PCT/CA2017/000102 filed 27 Apr. 2017, which claims priority to U.S. Provisional Application No. 62/328,325 filed 27 Apr. 2016. The entire contents of each of the above-referenced disclosures is specifically incorporated by reference herein without disclaimer.

REFERENCE TO SEQUENCE LISTING SUBMITTED ELECTRONICALLY VIA EFS-WEB

The content of the electronically submitted sequence listing in ASCII text file (Name: 4706_0160002_Seq-listing_ST26; Size: 142,568 bytes; and Date of Creation: Jan. 17, 2023), filed with the application, is incorporated herein by reference in its entirety.

FIELD OF THE INVENTION

The invention relates to the field of human leukocyte antigen (HLA) class I molecules and, more specifically, to methods of producing HLA class I molecules complexed with a peptide.

BACKGROUND OF THE INVENTION

Analysis of antigen-specific T-cells using flow cytometry with peptide-MHC (pMHC) multimers has been established as a standard technique in immunology[1,2]. These reagents enable the tracking and phenotypic analysis of antigen-specific T cells during immune responses associated with infection, autoimmunity, GVHD, and cancer.

αβ T-cell antigen receptors (TCRs) in T cells recognize peptide antigens presented by MHC class I or II molecules on the cell surface[3,4]. The interaction between TCR and pMHC is so weak that monomeric soluble pMHC in general cannot stably associate with the cell surface of T cells bearing a cognate TCR. pMHC multimers in the form of avidin-biotin-based pMHC tetramers were first introduced by Mark Davis' group in 1996 and immediately transformed the analysis of antigen-specific T cells[5]. pMHC multimers have been used in numerous studies and several commercial vendors, such as BD BioSciences™, ProImmune™, Immudex™, and TC Matrix™, sell pMHC multimers in various forms. pMHC multimers can be used in association with a combination of antibodies specific for other cell surface molecules[6]. Accordingly, simultaneous staining of TCR and immunoaccessory molecules allows the classification of antigen-specific T cells into various phenotypically distinct subsets. Such phenotyping can be used to characterize antigen-specific T cells in terms of their antigen exposure, effector function, and status.

*Escherichia coli* expression is the preferred method for production of MHC class I proteins and can provide large quantities of highly purified protein (tetramer.yerkes.emory.edu/support/protocols). Unlike class II molecules, most class I molecules are unstable as empty without peptide in the groove[7]. Therefore, in virtually all cases, MHC class I molecules are loaded with synthetic peptide of interest, where the class I expression process is coupled to a peptide-loading process to produce complete pMHC complex. There are some known issues with the bacterial system. For some HLA class I genes, such as HLA-B alleles, pHLA production using bacteria is difficult partly because of poor refolding[8,9]. Although glycosylation on class I protein is not necessary for the interaction between pMHC and cognate TCR, lack of sugar moieties on bacterially expressed MHC class I proteins may have a negative impact on their stability. Furthermore, bacterially expressed and in vitro refolded pMHC proteins may not have exactly the same higher structure as those produced in mammalians and refolded in vivo. Although in vitro peptide exchange of generated complete pMHC proteins is possible, it requires multiple complicated steps[10-12]. Therefore, high-throughput production of pMHC proteins is labor-intensive, cumbersome, and not widely available. Finally, it has been shown that the pMHC-TCR affinity required for pMHC multimer binding exceeds that required for T cell activation[13]. The observed difference in affinity threshold means that current pMHC tetramer staining cannot detect all antigen-specific T cells, especially with those with low affinity. Failure to stain all cognate T cells expressing TCR with a broad range of affinity is likely to be a serious issue when pMHC multimers are used to stain self antigen-specific T associated with immune responses in autoimmunity and cancer, which tend to express lower affinity TCRs.

SUMMARY OF INVENTION

According to one aspect, there is provided a method of producing an HLA class I molecule complexed to a pre-selected peptide by providing a mammalian derived HLA class I molecule complexed first to an existing peptide. The HLA class I molecule complexed to the existing peptide is then incubated, in vitro, with the pre-selected peptide at a concentration sufficient to replace the existing peptide, thereby producing the HLA class I molecule complexed to the pre-selected peptide. The HLA class I molecule comprises $\alpha 1$, $\alpha 2$, $\alpha 3$ and $\beta 2m$ domains.

According to a further aspect, there is provided a kit for producing an HLA class I molecule complexed to a pre-selected peptide, comprising a mammalian derived HLA class I molecule complexed to an existing peptide and instructions corresponding to the method described above. In some embodiments, the kit further comprises the pre-selected peptide.

According to a further aspect, there is provided a polypeptide comprising the $\alpha 1$, $\alpha 2$ and $\alpha 3$ domain of an HLA class I molecule, a signal peptide at the N terminus and a 6×His tag joined by a GS linker at the C terminus.

According to a further aspect, there is provided a nucleic acid encoding the polypeptide described above.

According to a further aspect, there is provided a vector comprising the nucleic acid described above.

According to a further aspect, there is provided a mammalian cell transfected with the vector described above.

According to a further aspect, there is provided a compound comprising the polypeptide described above complexed with a $\beta 2m$ domain.

According to a further aspect, there is provided a multimer of at least two of the compounds described above.

In an aspect, the method of screening/selecting in a population of T-cells for antigen specific T-cells that recognize pre-selected peptide antigens, the method comprising: providing a mammalian-derived HLA class I molecule complexed to the pre-selected peptides; screening the population of T-cells for antigen specific T-cells that bind the mammalian-derived HLA class I molecule complexed to the pre-selected peptides.

BRIEF DESCRIPTION OF FIGURES

Embodiments of the invention may best be understood by referring to the following description and accompanying drawings. In the drawings:

FIG. 15 shows A2$^+$ melanoma TILs.

FIG. 28 shows an A2 dimer staining summary.

DETAILED DESCRIPTION

We have developed a novel technology which enables high throughput production of mammalian-derived peptide/HLA class I (pHLA) multimers that can stain low affinity TCRs. One example application of this technology is the generation of personalized pHLA reagents which enables high-throughput measurement of antitumor T cell responses in cancer patients.

According to one aspect, there is provided a method of producing an HLA class I molecule complexed to a pre-selected peptide by providing a mammalian derived HLA class I molecule complexed first to an existing peptide. The HLA class I molecule complexed to the existing peptide is then incubated, in vitro, with the pre-selected peptide at a concentration sufficient to replace the existing peptide, thereby producing the HLA class I molecule complexed to the pre-selected peptide. The HLA class I molecule comprises α1, α2, α3 and β2m domains. In some embodiments, the HLA class I molecule is soluble.

Human Leukocyte Antigen

The HLA system is a gene complex encoding the major histocompatibility complex (MHC) proteins in humans. These cell-surface proteins are responsible for the regulation of the immune system in humans. HLA genes are highly polymorphic, and different classes have different functions. HLA class I genes encoding MHC class I molecules function to display or present peptide fragments of non-self or self proteins from within the cell to cytotoxic T cells.

Figure 1:
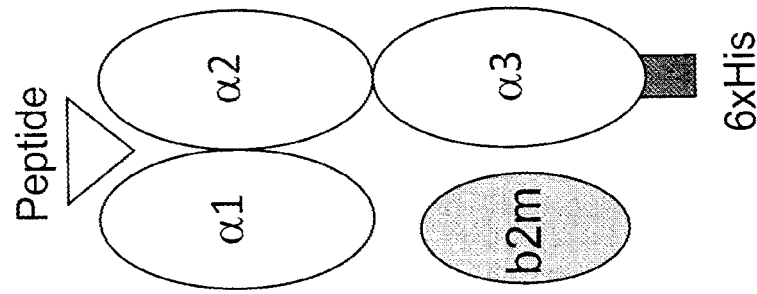
FIG. 1 shows a schematic representation of the general structure of an HLA class I molecule complexed with a peptide.

As used herein, the expression "HLA class I molecule" refers to a protein molecule derived from the expression of wild type or variant HLA class I genes encoding MHC class I molecules. A schematic representation of the general structure of an HLA class I molecule, including its α1, α2, α3 and β2m domains, is depicted in FIG. 1.

The schematic representation also illustrates a peptide complexed to the HLA class I molecule. As used herein, the expression "peptide" refers to peptide fragments that are capable of complexing with the HLA class I molecule and are displayed or presented by the HLA class I molecule. Such peptides have been well described in the art. In general, these particular peptides are about 8-15 amino acids in length but can also vary from between 8-10, 7-11, or 6-12 amino acids in length.

For some HLA class I genes, pHLA production using bacteria is difficult partly because of poor refolding. Furthermore, bacterially expressed and in vitro refolded pMHC proteins may not have exactly the same higher structure as those produced in mammalians and refolded in vivo. As used herein, the expression "mammalian derived" refers to production of molecules utilizing mammalian cell systems which are well known in the art, such as human cell lines (for example, Hela, HEK293, HEK293T and their derivatives), monkey cell lines (for example, CV-1, COS and their derivatives), mouse cell line (for example, NIH3T3 and their derivatives, NS-1 and their derivatives), hamster cell lines (for example, BHK, CHO and their derivatives). In one embodiment, human cell lines are used. In one example, HEK 293T cell lines can be used. The HLA class I molecule complexed to the existing peptide is produced by a mammalian cell transfected with a soluble HLA class I molecule, wherein the β2m domain may be endogenous or exogenous.

In preferred embodiments, the β2m domain is exogenous and encoded on a second vector.

In some embodiments, the soluble HLA class I molecule comprises a signal peptide directing secretion of the HLA class I molecule outside of the mammalian cell. In other embodiments, the soluble HLA class I molecule complexed to the existing peptide is provided in the supernatant of a culture of the mammalian cells.

HLA Class I Genes

The HLA class I genes is a family of genes. The HLA class I molecule can be HLA-A, HLA-B, HLA-C, HLA-E, HLA-F, or HLA-G.

As used herein, "HLA-A" refers to a protein molecule derived from the expression of an HLA-A gene. "HLA-B" refers to a protein molecule derived from the expression of an HLA-B gene. "HLA-C" refers to a protein molecule derived from the expression of an HLA-C gene. "HLA-D" refers to a protein molecule derived from the expression of an HLA-D gene. "HLA-E" refers to a protein molecule derived from the expression of an HLA-E gene. "HLA-F" refers to a protein molecule derived from the expression of an HLA-F gene. "HLA-G" refers to a protein molecule derived from the expression of an HLA-G gene. All of the genes HLA-A to HLA-G are part of the HLA class I family of genes.

Amino Acid Sequences of the HLA Class I Molecule

The HLA class I molecule may have a number of amino acid sequence variants.

In some embodiments, the α3 domain of the HLA class I molecule is the mouse Kb α3 domain (designated Kb)). In other embodiments, in the α2 domain of the HLA class I molecule, Gln has been replaced with Glu at position 115 (designated Q115E).

Exemplary HLA class I molecules include but are not limited to the following.

The HLA class I molecule may be HLA-A and comprises the α1, α2 and α3 domains of any of SEQ ID NOs. 6 or 12. In other embodiments, the HLA-A α1, α2 and α3 domains may be wildtype as in SEQ ID NOs. 2 or 14 respectively. Additionally, in yet other embodiments, the α1 and α2 domains are wildtype and the α3 domain of the HLA class I molecule is the mouse Kb α3 domain as in SEQ ID NOs. 4 or 10 respectively. Any combination of the foregoing is also possible.

The HLA class I molecule can be HLA-B and comprises the α1, α2 and α3 domains of any of SEQ ID NOs. 14, 16, 18, 20, or 22. As with exemplary HLA-A molecules, the α1, α2 and α3 domains may be wildtype, or be select variants, such as Kb and Q115E, or any combinations thereof.

The HLA class I molecule can be HLA-C and comprises the α1, α2 and α3 domains of any of SEQ ID NOs. 24, 26, 28, or 30. As with exemplary HLA-A molecules, the α1, α2 and α3 domains may be wildtype, or be select variants, such as Kb and Q115E, or any combinations thereof.

In yet other embodiments, the HLA class I molecule comprises the α1, α2 and α3 domains described herein with a β2m domain.

Multimers

The HLA class I molecule may also be multimerized. According to a further aspect, the method described above further comprises multimerizing the HLA class I molecules, preferably into one of dimers, trimers, tetramers and pentamers.

In some embodiments, the HLA class I molecules are dimerized using an antibody that recognizes a corresponding tag on HLA class I molecule. In further embodiments, the tag is a 6×His tag at the C' end of the α3 domain, preferably connected by a flexible linker, more preferably a GS linker. Other suitable tags for antibody binding are known in the art. Examples of acceptable tags are numerous and include AviTag, Calmodulin-tag, polyglutamate tag, His-tag, Myc-tag, and VSV-tag. Examples of acceptable flexible linkers are numerous; see for example Chen et al, *Adv Drug Deliv Rev.* 2013 Oct. 15; 65 (10): 1357-1369.

Kits and Reagents

According to a further aspect, there is provided a kit for producing an HLA class I molecule complexed to a pre-selected peptide, comprising a mammalian derived HLA class I molecule complexed to an existing peptide and instructions corresponding to the method described above. In some embodiments, the kit further comprises the pre-selected peptide.

According to a further aspect, there is provided a polypeptide comprising the α1, α2 and α3 domain of an HLA class I molecule, a signal peptide at the N terminus and a 6×His tag joined by a GS linker at the C terminus. In some embodiments, the polypeptide is SEQ ID NO. 2, 4, 6, 8, 10, 12, 14, 16, 18, 20, 22, 24, 26, 28, or 30.

According to a further aspect, there is provided a nucleic acid encoding the polypeptide described above.

According to a further aspect, there is provided a vector comprising the nucleic acid described above.

According to a further aspect, there is provided a mammalian cell transfected with the vector described above. In some embodiments, the mammalian cell further comprises a second vector encoding β2m.

According to a further aspect, there is provided a compound comprising the polypeptide described above complexed with a β2m domain.

According to a further aspect, there is provided a multimer of at least two of the compounds described above. In some embodiments, the at least two compounds are dimerized by an antibody recognizing the 6×His tag.

The following examples are illustrative of various aspects of the invention, and do not limit the broad aspects of the invention as disclosed herein.

T-Cell Screening and Selection, Including Tumor-Infiltrating Lymphocytes

It is known that HLA class I molecules complexed to a pre-selected peptide can be used to screen/select for T-cells that recognize said peptide antigen through its T-cell receptor. Advantageously, the mammalian derived HLA class I molecules described herein allow the skilled person to swap out an existing (or holder) peptide with a pre-selected peptide of interest. This was not possible with existing bacteria-derived HLA class I molecules. Rather, the existing bacteria-derived HLA class I molecules had to be produced, denatured and then re-folded with the peptide antigen of interest.

The present mammalian-derived HLA class I molecules therefore represent a streamlined and more flexible procedure to easily produce molecules that can present a peptide antigen. For example, the present mammalian-derived HLA class I molecules can be pre-made, the holder peptide being swapped before use. Further, the present mammalian-derived HLA class I molecules are likely more representative of a natural HLA class I molecules as they do not have to be refolded and are glycosylated.

Accordingly, in an aspect, the method of screening/selecting in a population of T-cells for antigen specific T-cells that recognize pre-selected peptide antigens, the method comprising: providing a mammalian-derived HLA class I molecule complexed to the pre-selected peptides; screening the population of T-cells for antigen specific T-cells that bind the mammalian-derived HLA class I molecule complexed to the pre-selected peptides.

In some embodiments, the method further comprises first providing a mammalian-derived HLA class I molecule complexed to a holder peptide; incubating, in vitro, the HLA class I molecule complexed to the holder peptide with the pre-selected peptide, wherein the pre-selected peptide is at a concentration sufficient to replace the existing peptide to produce the HLA class I molecule complexed to the pre-selected peptide.

In some embodiments, the mammalian-derived HLA class I molecule complexed to the pre-selected peptide is prepared using the method of described herein.

In some embodiments, the screening comprises flow cytometry.

In some embodiments, the HLA class I molecule complexed to the holder peptide comprises any one of SEQ ID NO. 2, 4, 6, 8, 10, 12, 14, 16, 18, 20, 22, 24, 26, 28, or 30, preferably with a β2m domain.

In some embodiments, the HLA class I molecule complexed to the holder peptide comprises the polypeptide described herein, preferably with a β2m domain.

In some embodiments, the method may be used to screen/select for T-Cell populations associated with a cancer. Cancer may include adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma-adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, or wilms tumor.

In some embodiments, the antigen specific T-cells that recognize pre-selected peptide antigens are tumor-infiltrating lymphocytes.

In some embodiments, the pre-selected peptide antigens are associated with cancer.

Examples

Materials and Methods

Peptides

Synthetic peptides were purchased from ProImmune, Genway Biotech, and GenScript. Peptides used were A2-restricted heteroclitic MART1$_{26-35}$ (ELAGIGILTV), heteroclitic NY-ESO-1$_{157-165}$ (SLLMWITQV), A24-restricted heteroclitic WT1$_{235-243}$ (CYTWNQMNL), B35-restricted wild-type EBNA-1$_{407-417}$ (HPVGEADYFEY) peptides, B44-restricted wild-type EBNA-6$_{281-290}$ (EENLLDFVRF), C7-restricted wild-type MAGE-A1$_{289-297}$ (RVRFFFPSL), and C7-restricted wild-type MAGE-A 12$_{170-178}$ (VRIGHLYIL) peptides. A2 peptides used to stain TILs are listed in Table 1 below.

TABLE 1

A2 peptides tested

|  | Name | Sequence | SEQ ID NO. |
|---|---|---|---|
| 1 | WT1 (37-) | VLDFAPPGA | 35 |
| 2 | WT1 (126-) | RMFPNAPYL | 36 |
| 3 | WT1 (87-) | SLGEQQYSV | 37 |
| 4 | WT1 (235-) | CMTWNQMNL | 38 |
| 5 | MIA (54-) | YMAPDCRFL | 39 |
| 6 | MIA (99-) | RLGYFPSSI | 40 |
| 7 | ALX1 (142-) | LQLEELEKV | 41 |
| 8 | ALX1 (170-) | ELTEARVQV | 42 |
| 9 | GAPDHS (358-) | FLGDTHSSI | 43 |
| 10 | GAPDH2 (345-) | ILAYTEDEV | 44 |
| 11 | S100B (44-) | FLEEIKEQEV | 45 |
| 12 | S100B (74-) | FMAFVAMVT | 46 |
| 13 | ABCB5 (1078-) | LLDEATSAL | 47 |
| 14 | ABCB5 (700-) | VLNGTVHPV | 48 |
| 15 | EXTL1 (249-) | VLLSPRWEL | 49 |
| 16 | EXTL1 (13-) | FLWDAYFSS | 50 |
| 17 | EXTL1 (330-) | WLALSASWL | 51 |
| 18 | CPN1 (379-) | LLLPGIYTV | 52 |
| 19 | CPN1 (249-) | KLFQKLAKV | 53 |
| 20 | CPN1 (297-) | YLHTNCFEI | 54 |
| 21 | TSPAN10 (81-) | FLSNFPFSL | 55 |
| 22 | TSPAN10 (94-) | ALAIGLWGL | 56 |
| 23 | TSPAN10 (142-) | ALCENTCLL | 57 |
| 24 | GJB1 (155-) | LLYPGYAMV | 58 |
| 25 | GJB1 (5-) | GLYTLLSGV | 59 |
| 26 | GJB1 (147-) | AVFMYVFYL | 60 |
| 27 | MITF (378-) | LMDDTLSPV | 61 |
| 28 | MITF (142-) | LQMANTLPV | 62 |
| 29 | MITF (392-) | LLSSVSPGA | 63 |
| 30 | DUSP4 (362-) | SQFVFSFPV | 64 |
| 31 | DUSP4 (326-) | QLLQFESQV | 65 |
| 32 | DUSP4 (53-) | FLAHSAGYI | 66 |
| 33 | cyclin-A1 (227-) | FLDRFLSCM | 67 |
| 34 | cyclin-A1 (341-) | SLIAAAAFCLA | 68 |
| 35 | HERV-K-MEL (1-) | MLAVISCAV | 69 |

TABLE 1-continued

A2 peptides tested

| | Name | Sequence | SEQ ID NO. |
|---|---|---|---|
| 36 | LAGE-1 (1-) | MLMAQEALAFL | 70 |
| 37 | MAGE-A1 (278-) | KVLEYVIKV | 71 |
| 38 | MAGE-A2 (157-) | YLQLVFGIEV | 72 |
| 39 | MAGE-A3 (271-) | FLWGPRALV | 73 |
| 40 | MAGE-A3 (112-) | KVAELVHFL | 74 |
| 41 | MAGE-A4 (230-) | GVYDGREHTV | 75 |
| 42 | MAGE-A9 (223-) | ALSVMGVYV | 76 |
| 43 | MAGE-A10 (254-) | GLYDGMEHL | 77 |
| 44 | MAGE-A12 (271-) | FLWGPRALV | 78 |
| 45 | MAGE-C1 (959-) | ILFGISLREV | 79 |
| 46 | MAGE-C1 (1083-) | KVVEFLAML | 80 |
| 47 | LAGE-2 (1-) | MLMAQEALAFL | 81 |
| 48 | SSX-2 (41-) | KASEKIFYV | 82 |
| 49 | XAGE-1b (21-) | RQKKIRIQL | 83 |
| 50 | CEA (691-) | IMIGVLVGV | 84 |
| 51 | gp100 (154-) | KTWGQYWQV | 85 |
| 52 | gp100 (177-) | AMLGTHTMEV | 86 |
| 53 | gp100 (178-) | MLGTHTMEV | 87 |
| 54 | gp100 (209-) | ITDQVPFSV | 88 |
| 55 | gp100 (280-) | YLEPGPVTA | 89 |
| 56 | gp100 (457-) | LLDGTATLRL | 90 |
| 57 | gp100 (476-) | VLYRYGSFSV | 91 |
| 58 | gp100 (570-) | SLADTNSLAV | 92 |
| 59 | gp100 (619-) | RLMKQDFSV | 93 |
| 60 | gp100 (639-) | RLPRIFCSC | 94 |
| 61 | NY-BR-1 (904-) | SLSKILDTV | 95 |
| 62 | TRP-2 (180-) | SVYDFFVWL | 96 |
| 63 | TRP-2 (360-) | TLDSQVMSL | 97 |
| 64 | tyrosinase (1-) | MLLAVLYCL | 98 |
| 65 | tyrosinase (8-) | CLLWSFQTSA | 99 |
| 66 | tyrosinase (369-) | YMDGTMSQV | 100 |
| 67 | CD274 (15-) | LLNAFTVTV | 101 |
| 68 | CPSF (250-) | KVHPVIWSL | 102 |
| 69 | CPSF (1360-) | LMLQNALTTM | 103 |
| 70 | cyclin D1 (101-) | LLGATCMFV | 104 |
| 71 | IDO1 (199-) | ALLEIASCL | 105 |
| 72 | mdm-2 (53-) | VLFYLGQY | 106 |
| 73 | p53 (264-) | LLGRNSFEV | 107 |
| 74 | p53 (65-) | RMPEAAPPV | 108 |
| 75 | PRAME (100-) | VLDGLDVLL | 109 |
| 76 | PRAME (142-) | SLYSFPEPEA | 110 |
| 77 | PRAME (300-) | ALYVDSLFFL | 111 |
| 78 | PRAME (425-) | SLLQHLIGL | 112 |
| 79 | SOX10 (332-) | AWISKPPGV | 113 |
| 80 | SOX10 (331-) | SAWISKPPGV | 114 |
| 81 | survivin (95-) | ELTLGEFLKL | 115 |
| 82 | Telomerase (865-) | RLVDDFLLV | 116 |
| 83 | Wild type MART1 (27-35) | AAGIGILTV | 117 |
| 84 | Heteroclitic MART1 (26-35) | ELAGIGILTV | 118 |
| 85 | Wild type NY-ESO-1 (157-165) | SLLMWITQC | 119 |
| 86 | Heteroclitic NY-ESO-1 (157-165) | SLLMWITQV | 120 |
| 87 | HIV pol (476-484) | ILKEPVHGV | 121 |
| 88 | HTLV-1 tax (11-19) | LLFGYPVYV | 122 |
| 89 | No peptide exchange | | |

Cells and cDNAs

HEK293T cells were obtained from American Type Culture Collection. TILs isolated from an HLA-A2+ patient with metastatic melanoma were grown in vitro as reported previously[14]. Appropriate informed consent and institutional review board approval were obtained. All clonotypic TCR genes were reconstituted in Jurkat 76/CD8 cells or primary T cells as previously described. cDNAs were fused with puromycin resistance gene via internal ribosome entry site[15,16]. Transduced cells were isolated by puromycin selection. All cDNAs were cloned into pMX vector and transduced using 293GPG cell-based retrovirus system[16-19].

Flow Cytometry Analysis mAbs recognizing the following surface antigens were used: β2m (551337, BD BioSciences), His (ab72467, Abcam). Mouse isotype controls were from BD BioSciences. Surface molecular staining was carried out as described elsewhere[16,20].

Immunoblotting

For immunoblotting, cells were extracted in ice-cold Nonidet P-40 (NP-40) extraction buffer (20 mM Tris-HCl, pH 7.5, containing 1 mM EDTA, 150 mM NaCl, 2.5 mM sodium pyrophosphate, 1 mM β-glycerophosphate, 1% NP-40, 1 mM PMSF, and 1 μg/ml Aprotinin). Cell extracts were centrifuged at 10,000 g for 10 min at 4° C. and separated by Tris-Glycine SDS-PAGE followed by electrophoretic transfer to Immobilon-P membrane (Millipore). After blocking with 5% nonfat dry milk in Tris-buffered saline containing 0.1% Tween 20, the membranes were incubated with the indicated mouse anti-His mAb (sc-53073, Santa Cruz Biotechnology) at 4° C. overnight, washed and incubated with HRP-conjugated goat anti-mouse IgG (H+L) secondary antibody (Promega) at room temperature for 1 hr. The signal was detected by enhanced chemiluminescence (GE Healthcare).

Results and Discussion

Structure of Soluble Monomeric Peptide/HLA Class I (pHLA) Complexes

HLA class I molecules are heterodimers consisting of two polypeptide chains, α and β2-microglobulin (β2m), which are non-covalently linked. While the α chain is highly polymorphic, the β2m subunit is monomorphic. The HLA class I α1 and α2 domains constitute a groove for peptides of 8-10 amino acids in length. The α3 domain, which contains a transmembrane domain, binds β2m. While TCR on the surface of cytotoxic T cells recognizes the peptides presented by the HLA class I α1 and α2 domains to check antigenicity, the CD8 co-receptor binds the α2 and α3 domains to stabilize the interaction between the TCR and pHLA. Therefore, enhancement of the CD8 and HLA class I interaction leads to the improvement in the strength of the interaction between pHLA and cognate TCR.

It has been demonstrated that replacement of HLA class I α3 domain with mouse $K^b$ α3 domain, named hereafter class I-$K^b$, enhances the interaction between the class I and CD8 by 10 times. Substitution of the Gln (Q) residue at position 115 of the α2 domain with a Glu (E) residue, named hereafter class $I^{Q115E}$, further improves the interaction by 1.5 times[21,22]. By fusing the extracellular domain of wild-type (wt) HLA class I with a Gly-Ser (GS) flexible linker followed by a 6×His tag, we have generated soluble class I-wt. Soluble class I-$K^b$ and class $I^{Q115E}$_$K^b$ were similarly produced. Nucleotide and amino acid sequences of soluble class I-wt, class I-$K^b$, and class $I^{Q115E}$-$K^b$ genes used in this study are listed below.

Production of Soluble Monomeric pHLA Complexes Using Mammalian Cells

HEK293T cells were initially transfected with β2m gene and subsequently with soluble HLA class I-$K^b$ or HLA class $I^{Q115E}$_$K^b$ gene using the pMX vector and 293GPG cell-based retrovirus system 16-19.

Enhanced β2m Expression by Gene Transduction

Flow cytometry analysis following β2m-specific mAb staining demonstrated enhanced β2m expression in HEK293T cells stably transfected with β2m gene along with a soluble form of HLA-A2-$K^b$ or A2$^{Q115E}$_$K^b$. HLA-A*02:01 (A2) gene, which is one of the most frequent HLA class I alleles, was used as a representative HLA class I gene. The same strategy was applied to generate HEK293T-derived cell lines stably expressing a soluble form of other class I genes.

Cellular Expression of Soluble Monomeric Peptide/HLA (pHLA) in HEK293T Transfectants Total cell lysates of HEK293T cells stably expressing soluble HLA-A2-$K^b$ or A2$^{Q115E}$_$K^b$ gene in conjunction with or without β2m gene were blotted with anti-His mAb as reported previously[23-25] Cellular expression of soluble HLA-A2-$K^b$ and A2$^{Q115E}$_$K^b$ was demonstrated at the protein level.

Secretion of Soluble Monomeric pHLA Complexes into the Supernatant.

Supernatant of HEK293T cells transfected with soluble HLA-A2-$K^b$ or A2$^{Q115E}$_$K^b$ gene along with or without β2m gene was harvested and blotted with His-specific mAb. Indicated amounts of bacterially-expressed and 6×His-tagged HLA-A2/heteroclitic MART1$_{26-35}$ monomer (NIH tetramer core facility) were loaded as controls. Ten μl of each supernatant was loaded per lane without any concentration. Secretion of monomeric HLA-A2-$K^b$ and A2$^{Q115E}$_$K^b$ into the medium was confirmed.

Monomeric pHLA Complexes were Secreted Only when β2m was Overexpressed.

When HEK293T cells were transduced with soluble HLA-A2-$K^b$ or A2$^{Q115E}$_$K^b$ gene alone without β2m gene, secretion of soluble A2-$K^b$ and A2$^{Q115E}$_$K^b$ into the medium was not detectable. This suggests that the endogenous β2m expression level was not sufficient to enable the secretion of ectopically expressed soluble A2-$K^b$ and A2$^{Q115E}$_$K^b$.

Production of Monomeric pHLA Loaded with Peptide of Interest by In Vitro Peptide Exchange.

Figure 2:
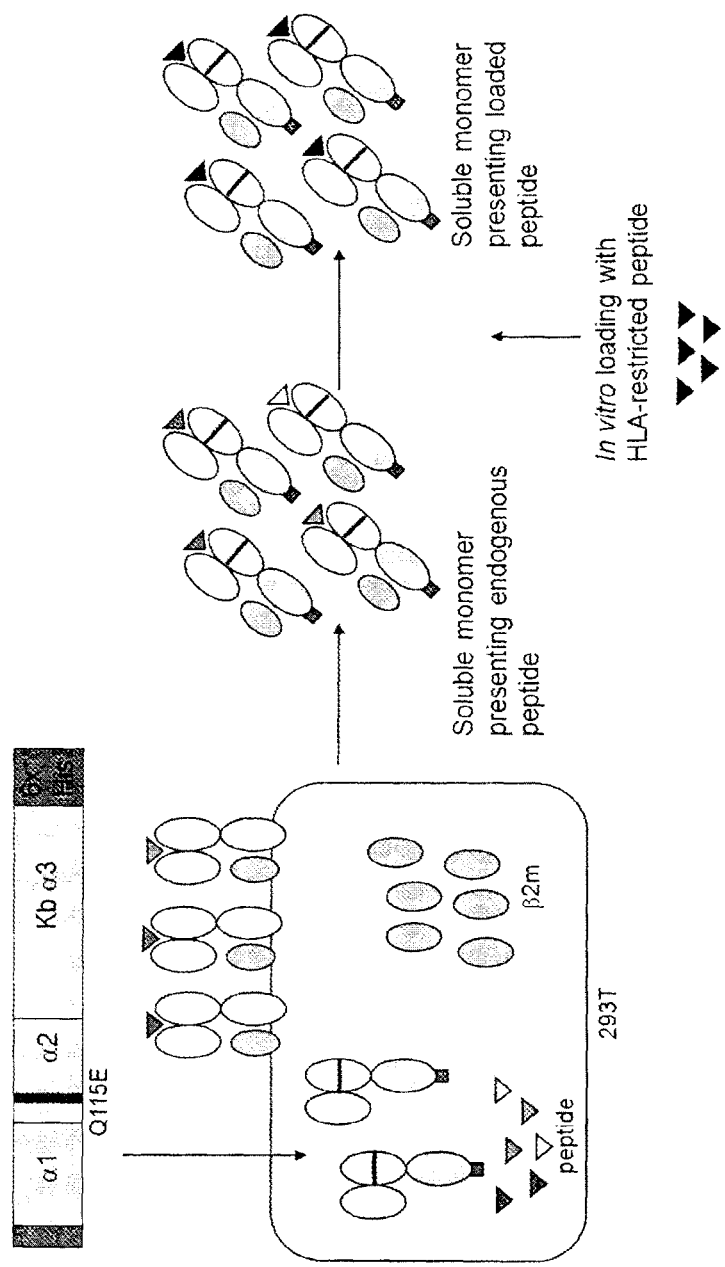
FIG. 2 shows production of monomeric pHLA presenting peptide of interest by in vitro peptide exchange.

Soluble HLA-A2-$K^b$ and A2$^{Q115E}$_$K^b$-containing supernatant produced by the HEK293T transfectants were simply mixed with the indicated concentration of A2-restricted peptide of interest at room temperature for in vitro peptide exchange (see FIG. 2).

Dimerization of Monomeric pHLA Complexes.

Soluble HLA classI$^{Q115E}$_$K^b$ monomer in the HEK293T conditioned medium was dimerized using anti-His mAb conjugated with fluorochrome such as phycoerythrin (PE) at at 2:1 molar ratio. Note that the soluble proteins were fused with a 6×His tag at the C-terminus.

Overall Protocol for Production of Dimeric pHLA Complexes to Stain Antigen-Specific T Cells.

Figure 3:
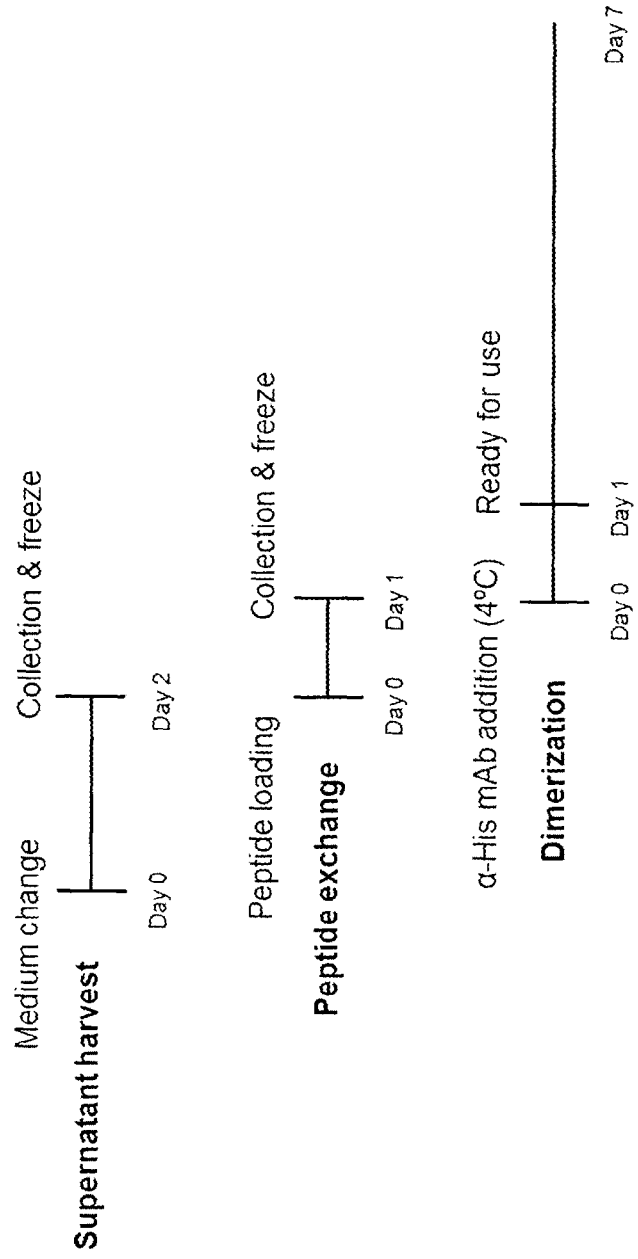
FIG. 3 shows a timeline chart of harvest, peptide loading, and dimerization of pHLA to stain antigen-specific T cells.

Stable HEK293T cell lines ectopically expressing soluble monomeric class $I^{Q115E}$-$K^b$ and β2m were established as described above. The stable cell lines were grown until confluent and medium was changed. After 48 hrs, the conditioned medium was harvested and immediately used or frozen until use. The supernatant was loaded with class I-restricted peptide of interest for 24 hrs at 37° C. for in vitro peptide exchange. The soluble monomeric class $I^{Q115E}$_$K^b$ loaded with the peptide was dimerized using fluorochrome-conjugated anti-His mAb for 24 hrs at 4° C. (see FIG. 3).

Peptide Exchange Occurs in the Supernatant by Simple Mixing.

Figure 4:
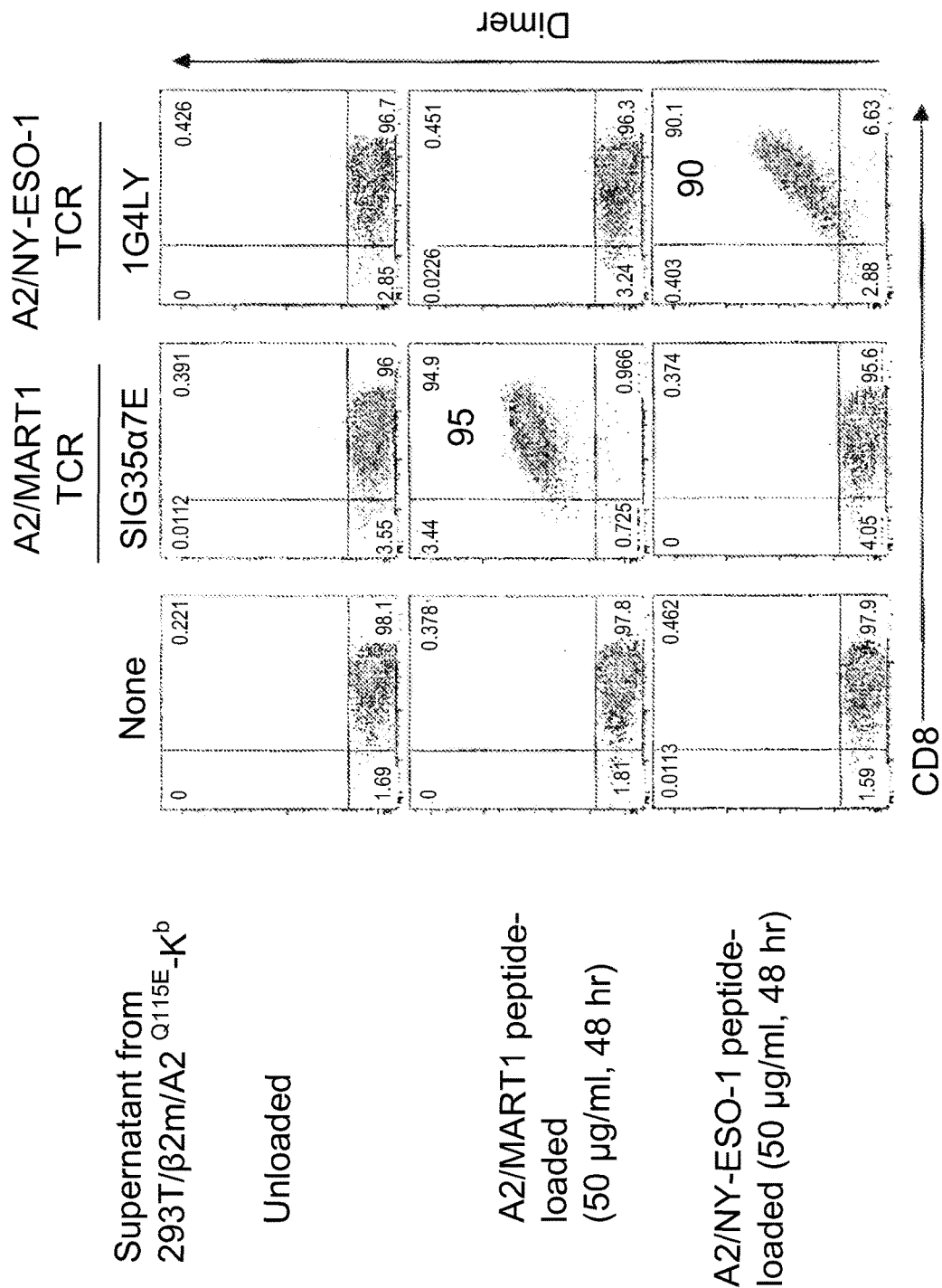
FIG. 4 shows staining data showing peptide exchange occurring in a supernatant sample.

Soluble A2$^{Q115E}$_$K^b$ monomer was loaded with A2/MART1$_{26-35}$ (ELAGIGILTV) or A2/NY-ESO-1$_{157-165}$ (SLLMWITQV) peptide by simple mixing, dimerized with PE-conjugated anti-His mAb, and used to stain human Jurkat 76/CD8 T cells expressing clonotypic cognate TCR (see FIG. 4). Jurkat 76/CD8 cells, lacking the endogenous TCR expression, stably express CD8α/β genes[26,27].

Soluble Monomeric A2$^{Q115E}$_$K^b$ Stains High Avidity Antigen-Specific T Cells.

Figure 5A:
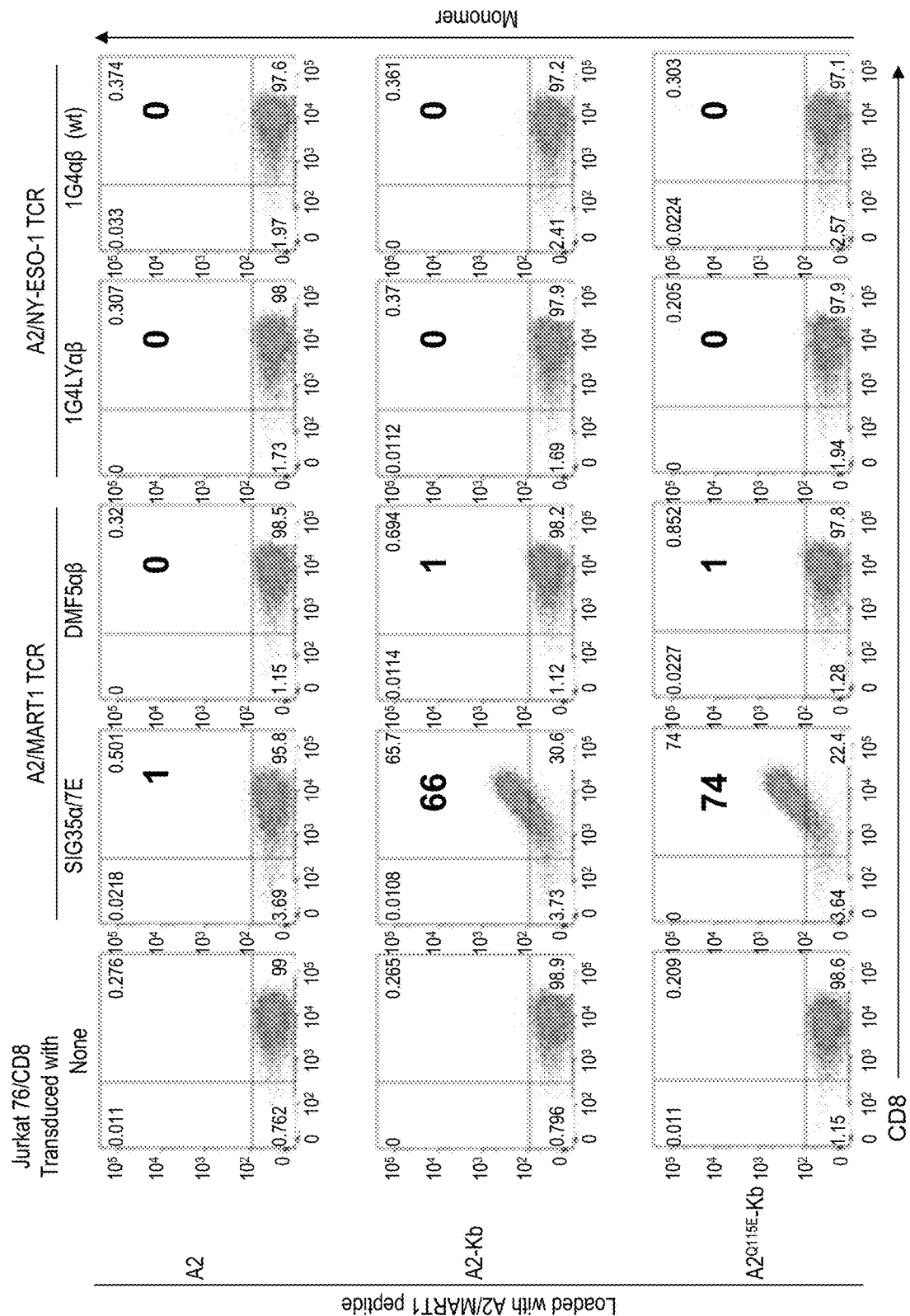
FIGS. 5A and 5B show staining data showing A2/MART1 monomer staining high avidity A2/MART1 T cells but not A2/NY-ESO-1 T cells.
Figure 5B:
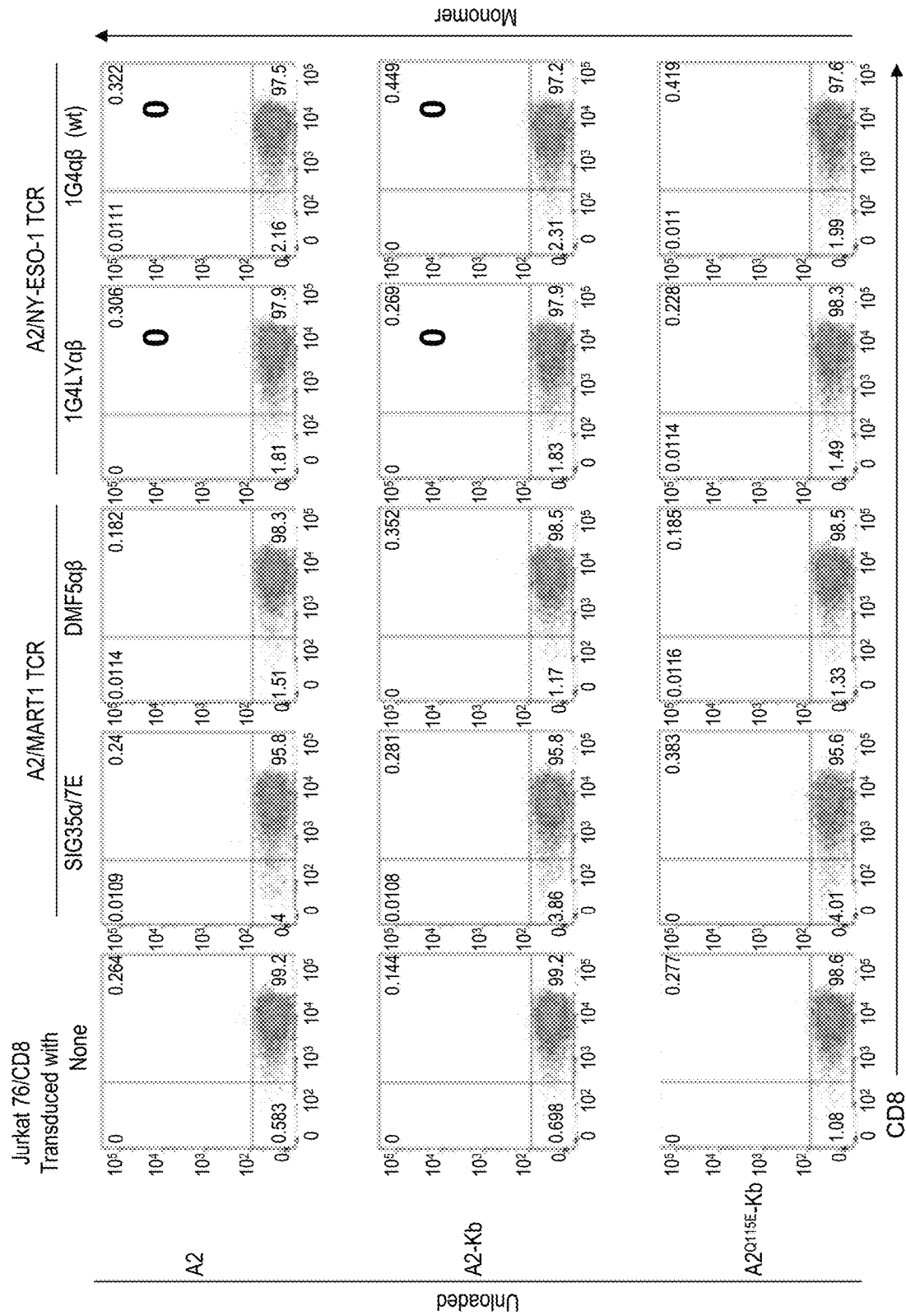
Figure 6A:
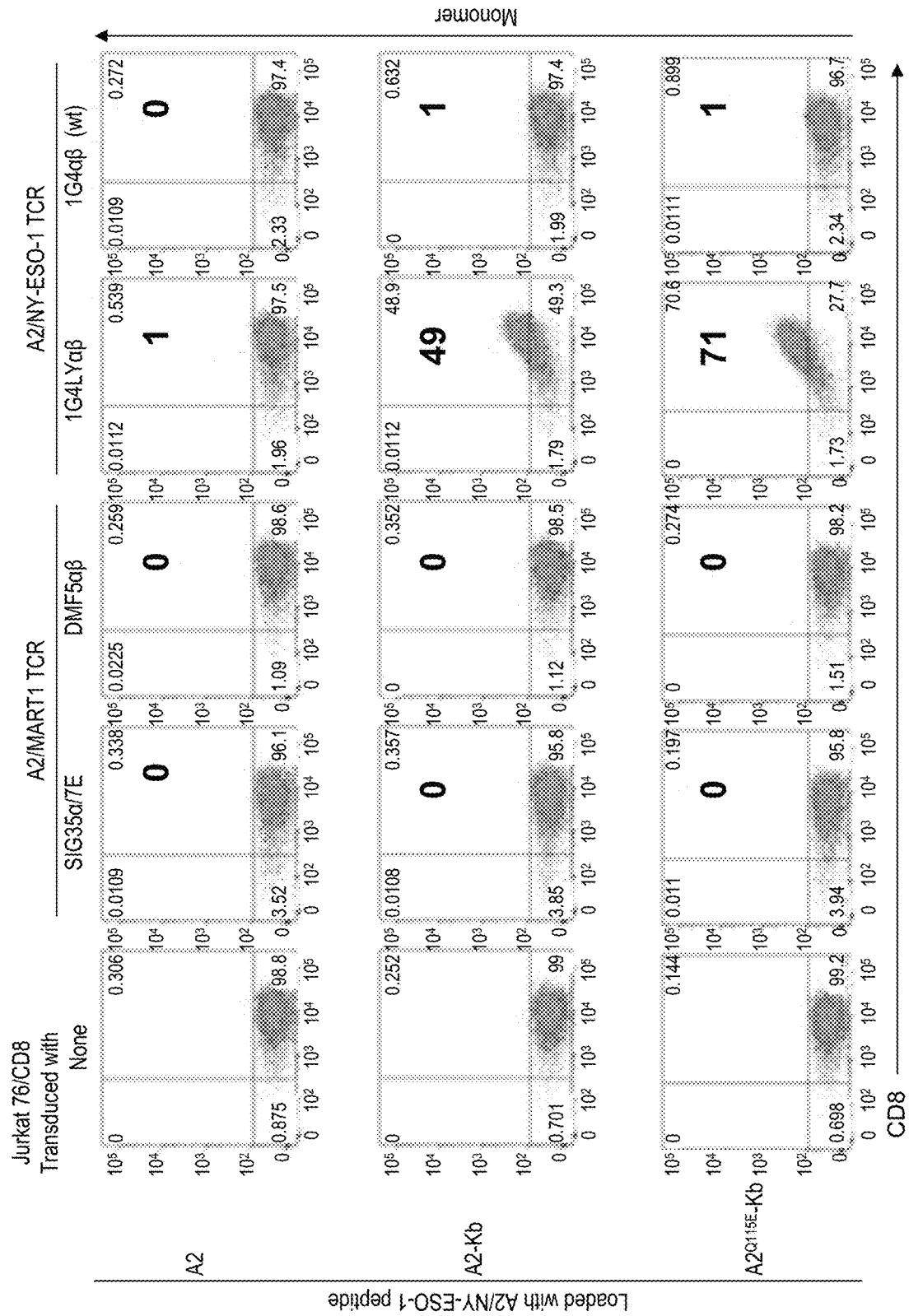
FIGS. 6A and 6B show staining data showing A2/NY-ESO-1 monomer staining high avidity A2/NY-ESO-1 T cells but not A2/MART1 T cells.
Figure 6B:
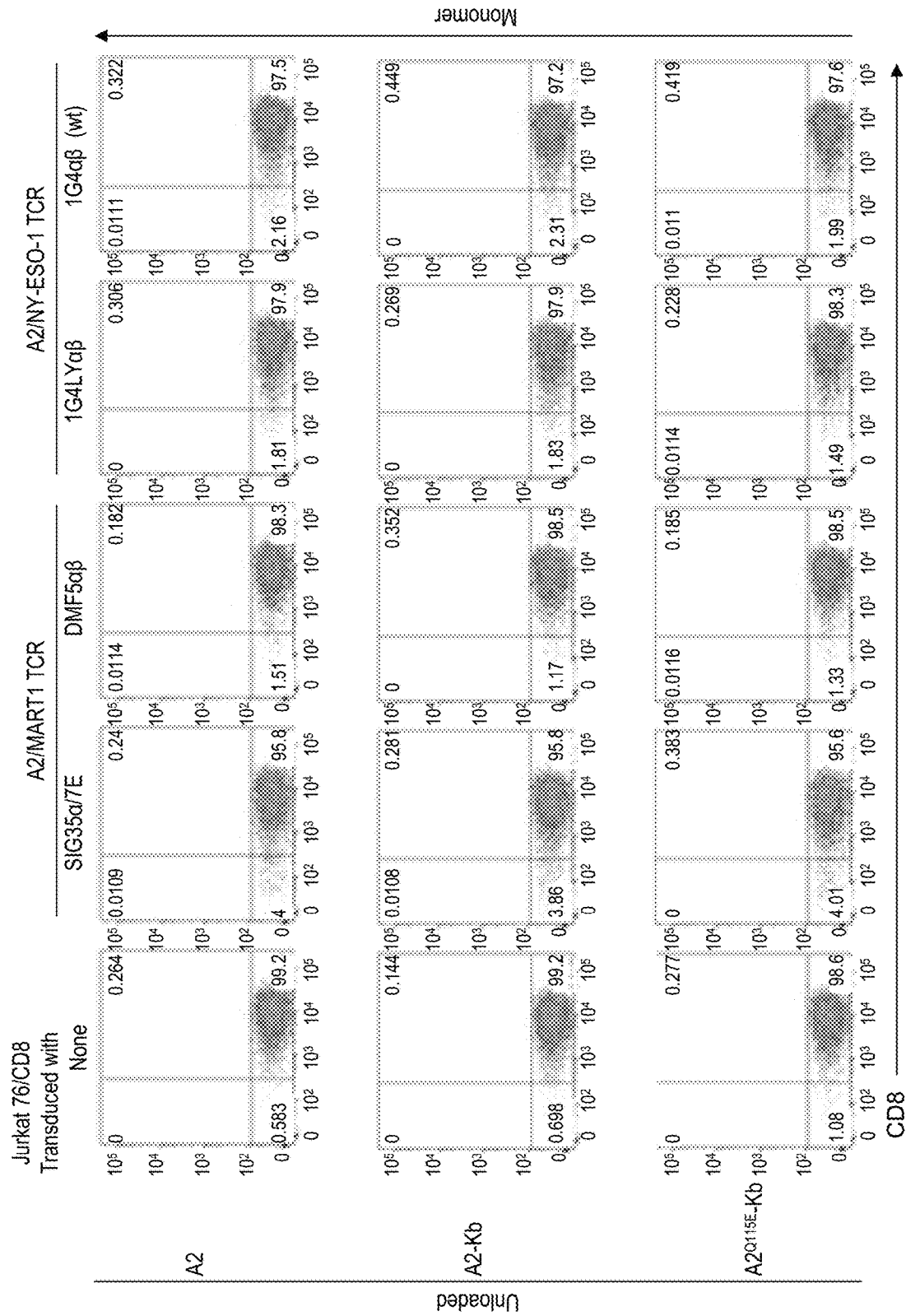

Soluble A2$^{Q115E}$_$K^b$ monomer was loaded with A2/MART1$_{26-35}$ or A2/NY-ESO-1$_{157-165}$ peptide by simple mixing and, without dimerization, directly used to stain Jurkat 76/CD8 T cells expressing clonotypic cognate TCR. Jurkat 76/CD8 cells expressing high but not low affinity TCRs were stained by monomeric soluble A2$^{Q115E}$-$K^b$ loaded with cognate peptide (see FIGS. 5 and 6)[27].

Soluble Dimeric A2$^{Q115E}$-$K^b$ Stains Both High and Low Avidity Antigen-Specific T Cells.

Figure 7A:
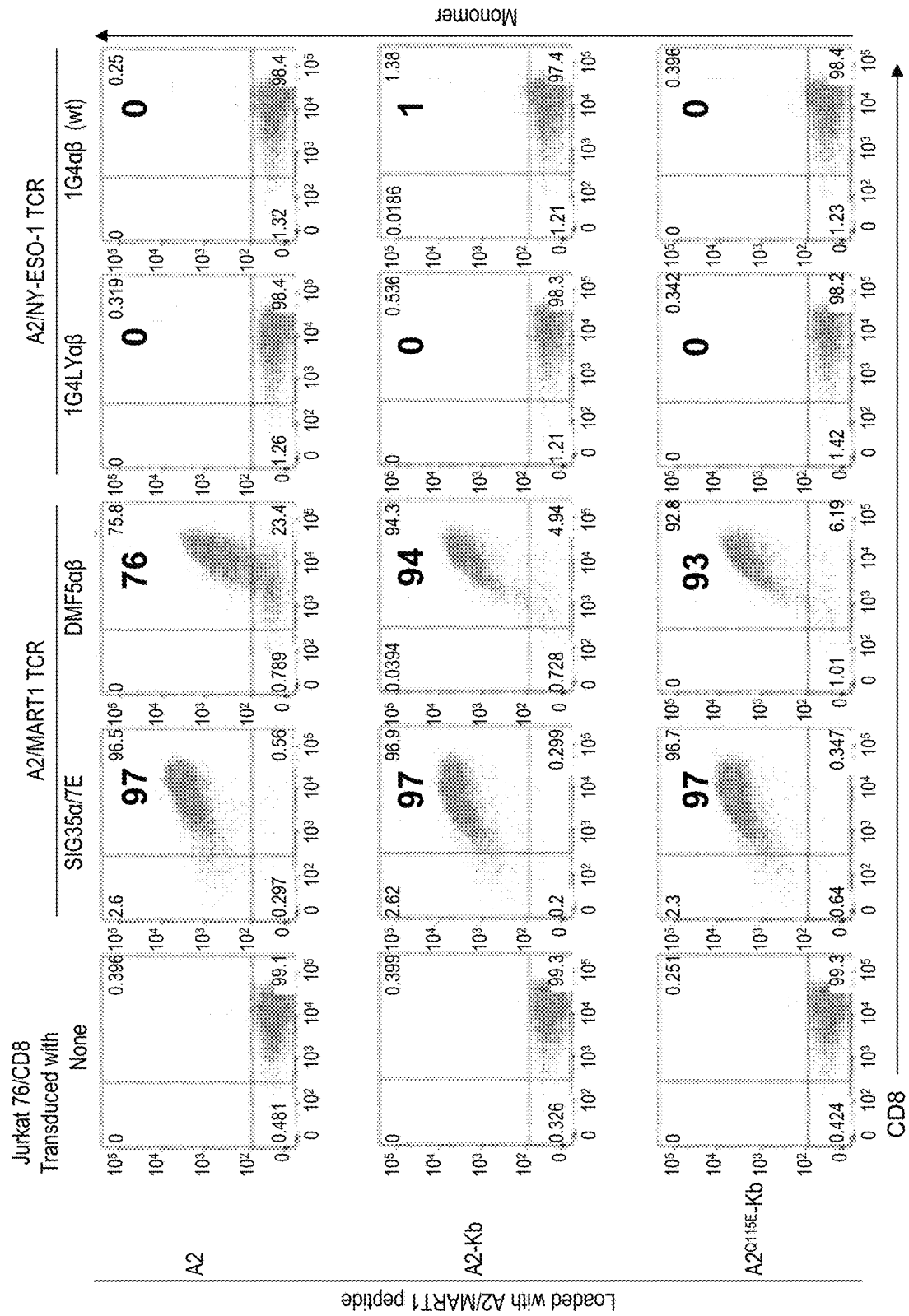
FIGS. 7A and 7B show staining data showing A2/MART1 dimer staining A2/MART1 T cells but not A2/NY-ESO-1 T cells.
Figure 7B:
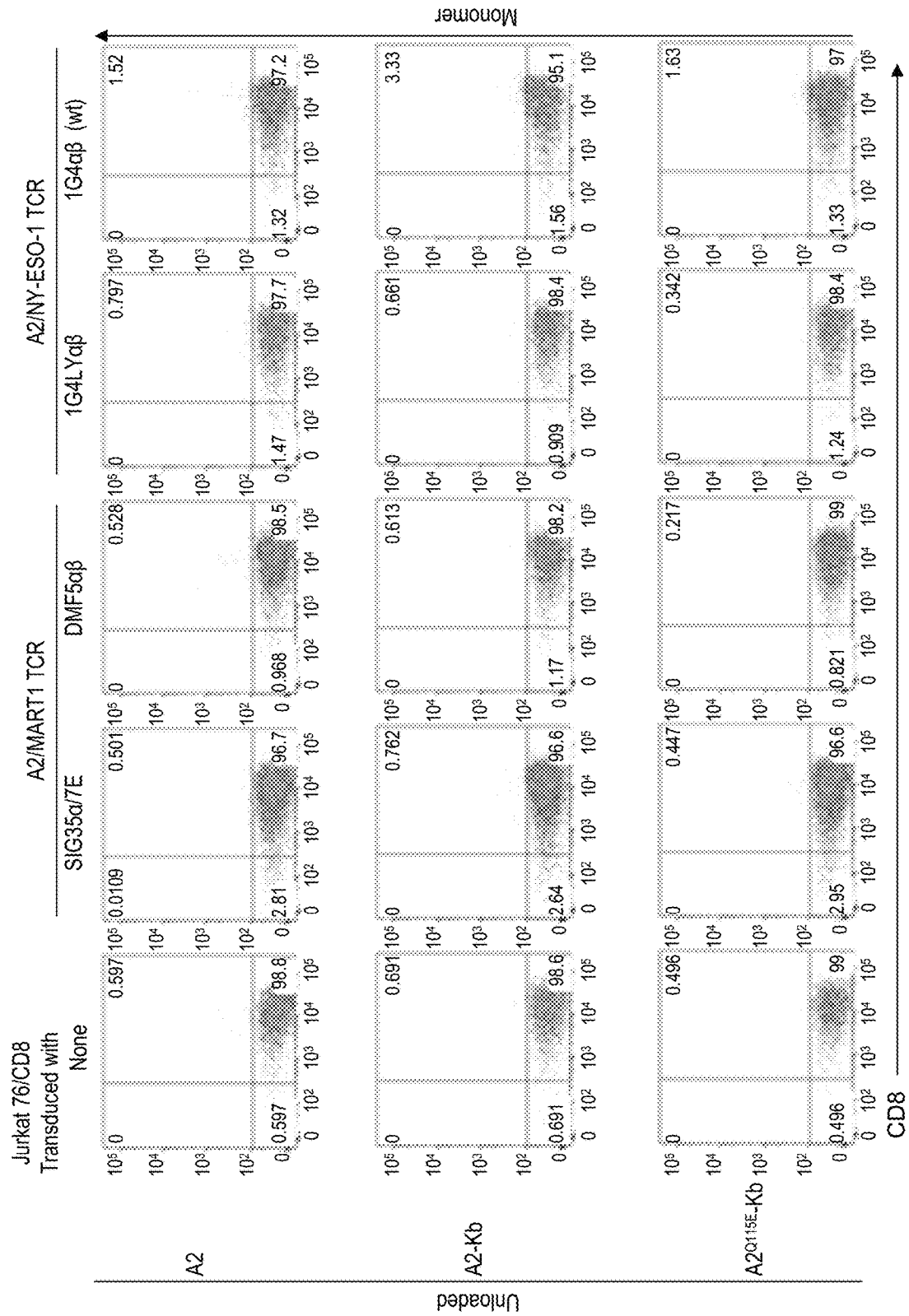
Figure 8A:
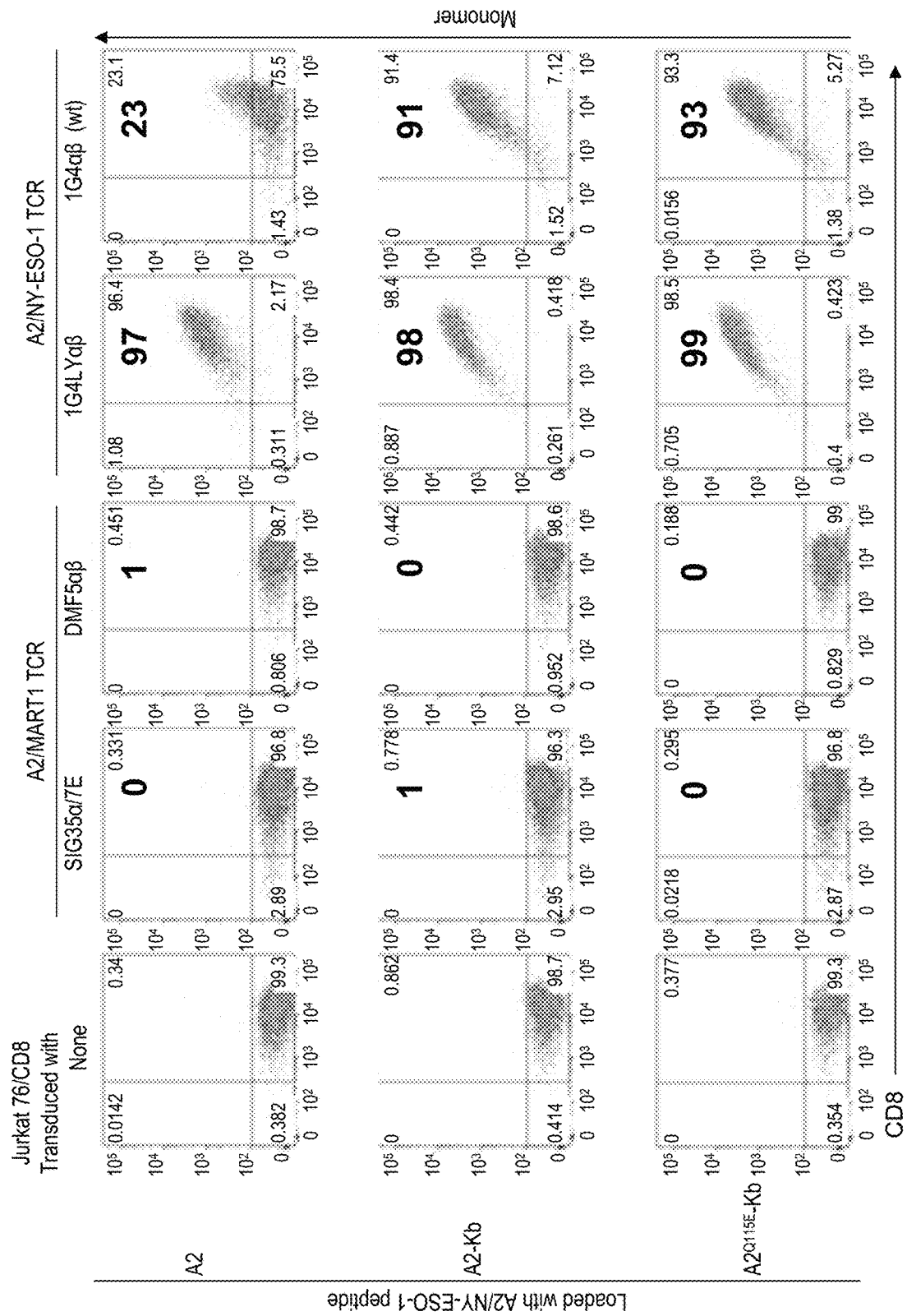
FIGS. 8A and 8B show staining data showing A2/NY-ESO-1 dimer staining A2/NY-ESO-1 T cells but not A2/MART1 T cells.
Figure 8B:
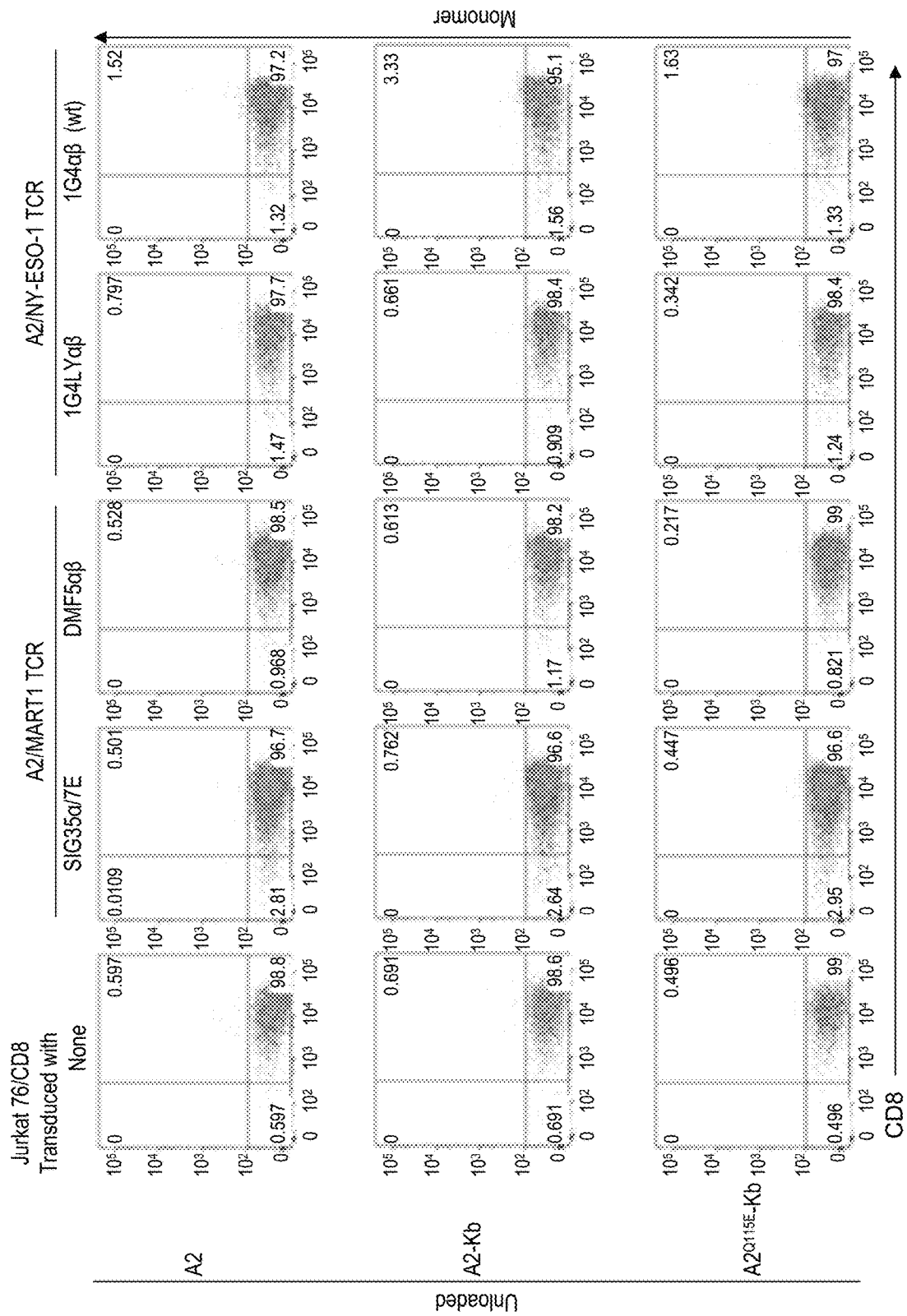

Soluble monomeric A2$^{Q115E}$-$K^b$ containing supernatant was loaded with A2/MART1$_{26-35}$ or A2/NY-ESO-1$_{157-165}$ peptide by simple mixing, dimerized with PE-conjugated anti-His mAb, and utilized to stain Jurkat 76/CD8 T cells expressing clonotypic cognate TCR (see FIGS. 7 and 8). Both high and low affinity TCRs expressed in Jurkat 76/CD8 cells were stained by soluble dimeric A2$^{Q115E}$_$K^b$ loaded with respective peptide[27].

Soluble Dimeric Class I$^{Q115E}$-K$^b$ Stains Low Affinity TCRs Better than Pentamer (ProImmune) or Tetramer (NIH)

Figure 9:
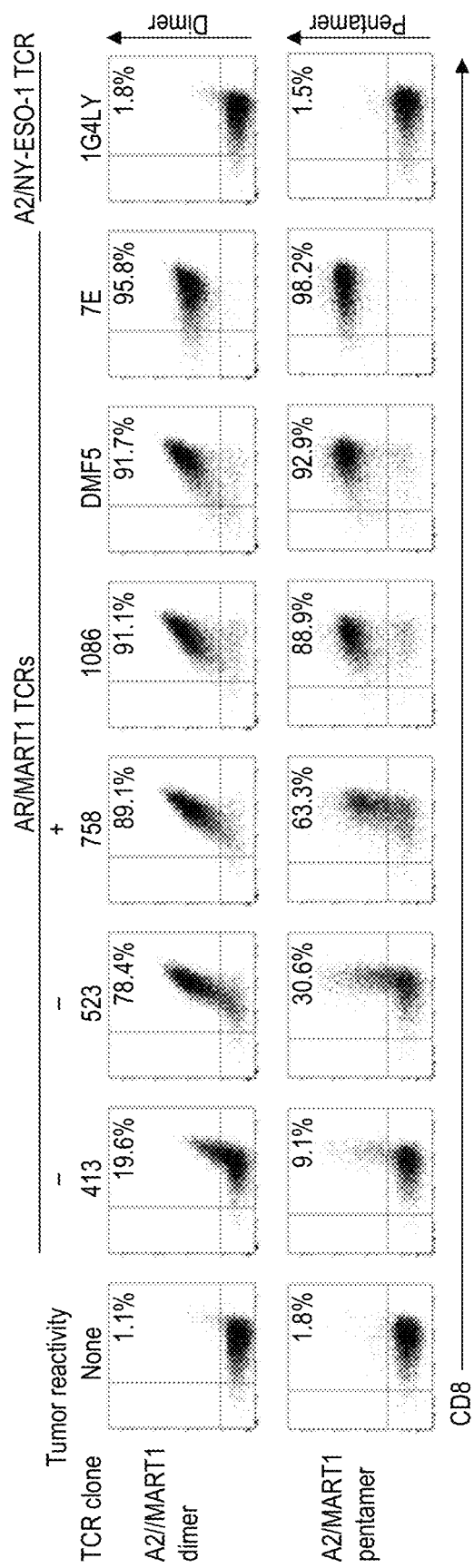
FIG. 9 shows staining data showing a dimer embodiment staining low affinity A2/MART1 TCRs better than a known Pentamer.
Figure 10:
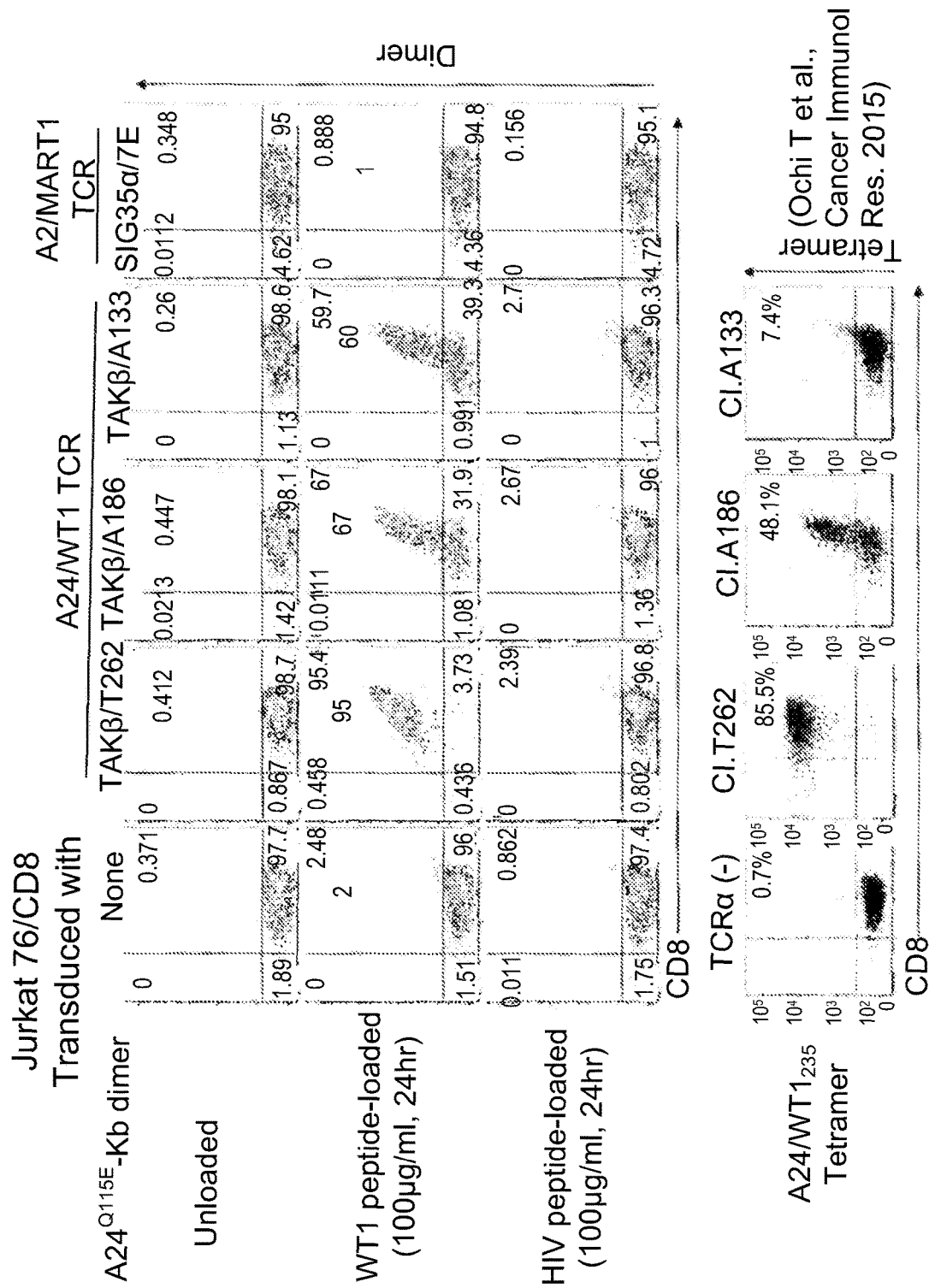
FIG. 10 shows staining data showing A24Q115E-Kb dimer staining low affinity A24/WT1 TCRs better than a prior art A24/WT1 tetramer.

PE-conjugated soluble dimeric A2$^{Q115E}$_K$^b$ and A24$^{Q115E}$_K$^b$ were loaded with A2/MART1$_{26-35}$ and A24/WT1$_{235-243}$ (CYTWNQMNL) peptides, respectively. The loaded dimers were employed to stain Jurkat 76/CD8 T cells expressing clonotypic cognate TCRs with various affinities[26,27]. Our dimer stained low affinity TCRs better than Pentamer (ProImmune) and NIH's tetramer (see FIGS. 9 and 10). Pentamer was used according to the protocol provided by the vendor (www.proimmune.com/ecommerce/page.php?page=protocols). Tetramer staining was performed according to the standard protocol as published elsewhere[26,27].

Soluble Dimeric HLA-B$^{Q115E}$_K$^b$ Works as Well.

Figure 11:
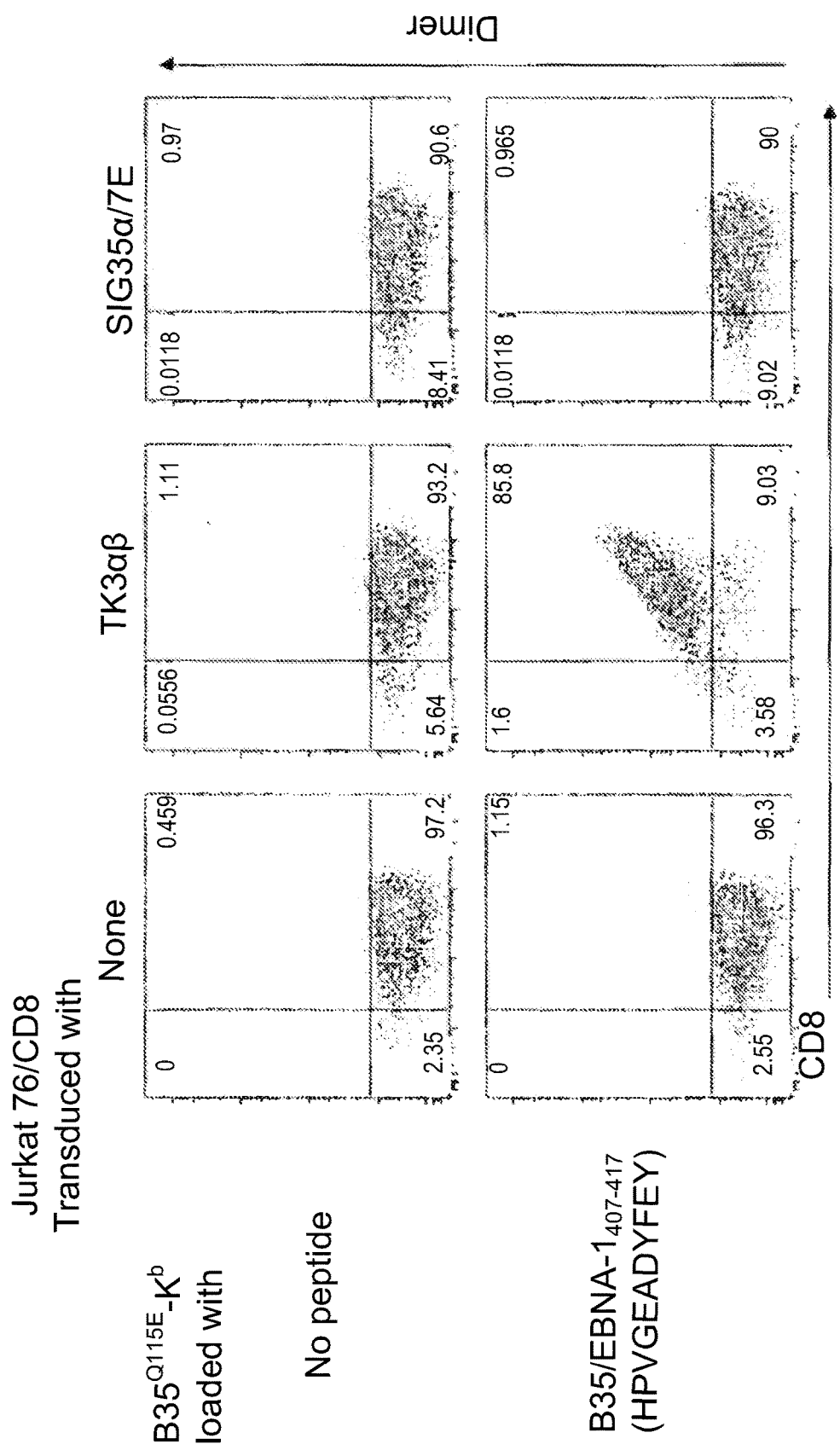
FIG. 11 shows staining data showing B35Q115E-Kb dimer stains B*35:01/EBNA-$1_{407-417}$ TCR (Clone TK3).
Figure 12:
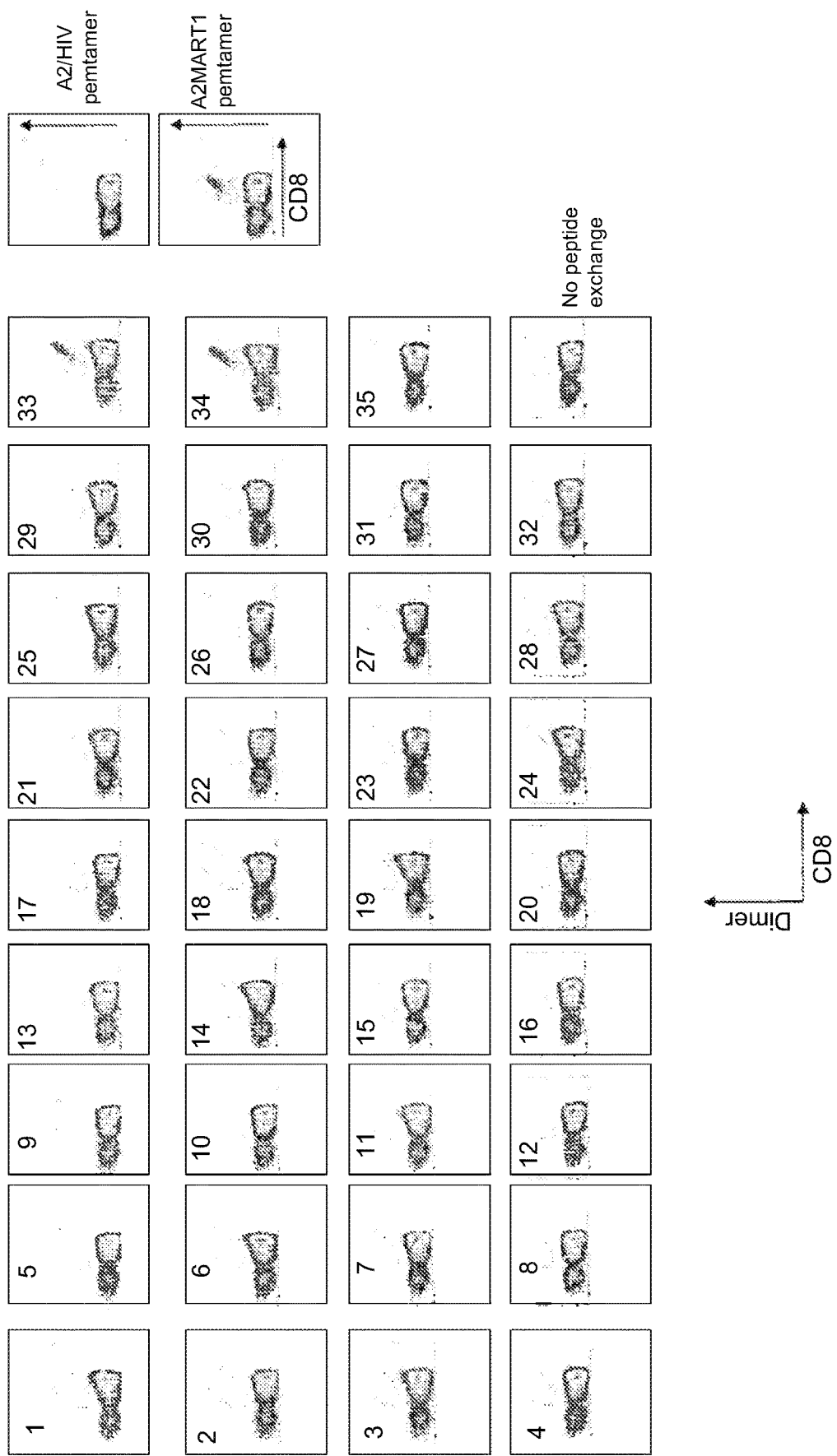
FIG. 12 shows staining data showing high throughput A2 dimer staining of TILs.

Soluble monomeric HLA-B35$^{Q115E}$-K$^b$ was loaded with B35/EBNA-1$_{407-417}$ (HPVGEADYFEY) peptide, dimerized with PE-conjugated anti-His mAb, and used to stain Jurkat 76/CD8 T cells expressing clonotypic cognate TCR (see FIG. 11).

Figure 13:
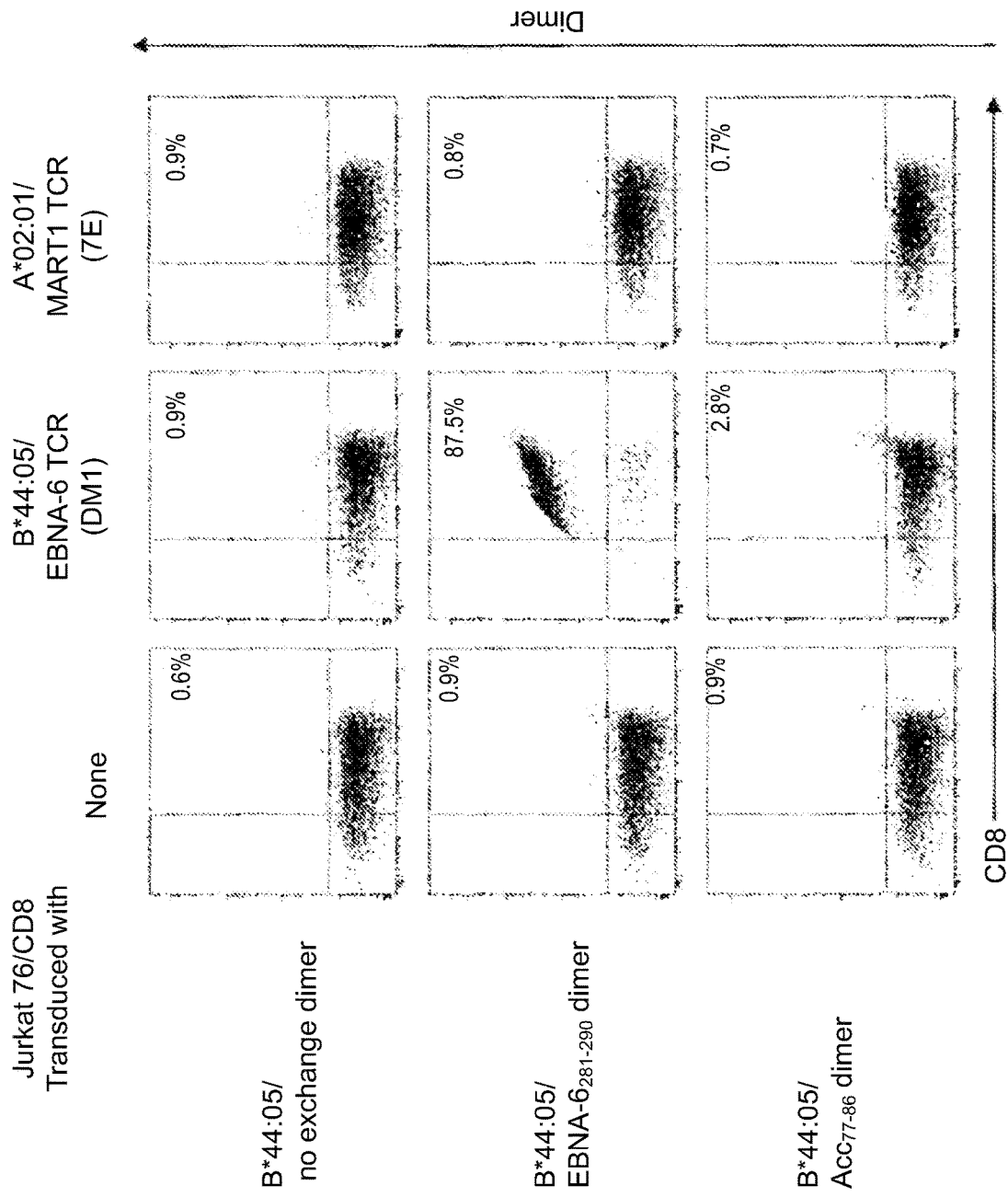
FIG. 13 shows B*44:05 dimer stains B*44:05/EBNA-$6_{281-290}$ TCR.

Soluble monomeric HLA-B44$^{Q115E}$_K$^b$ was loaded with B44/EBNA-6$_{281-290}$ (EENLLDFVRF), dimerized with PE-conjugated anti-His mAb, and used to stain Jurkat 76/CD8 T cells expressing clonotypic cognate TCR (FIG. 13).

Soluble Dimeric HLA-C$^{Q115E}$_K$^b$ Works as Well.

Figure 14:
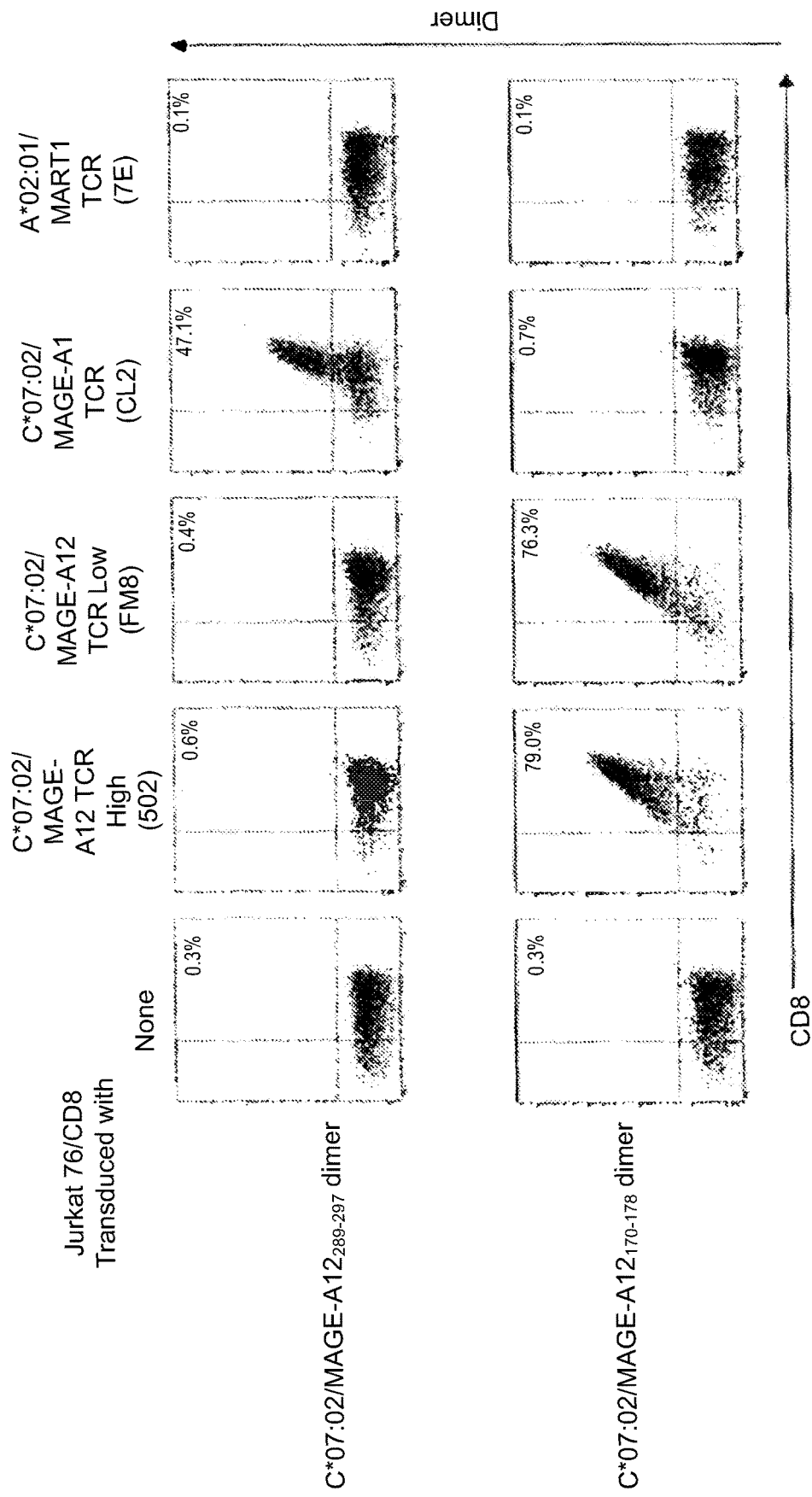
FIG. 14 shows C*07:02/MAGE-A$1_{289-297}$ and C*07:02/MAGE-A$12_{170-178}$ dimers stain respective TCRs.
Figure 16:
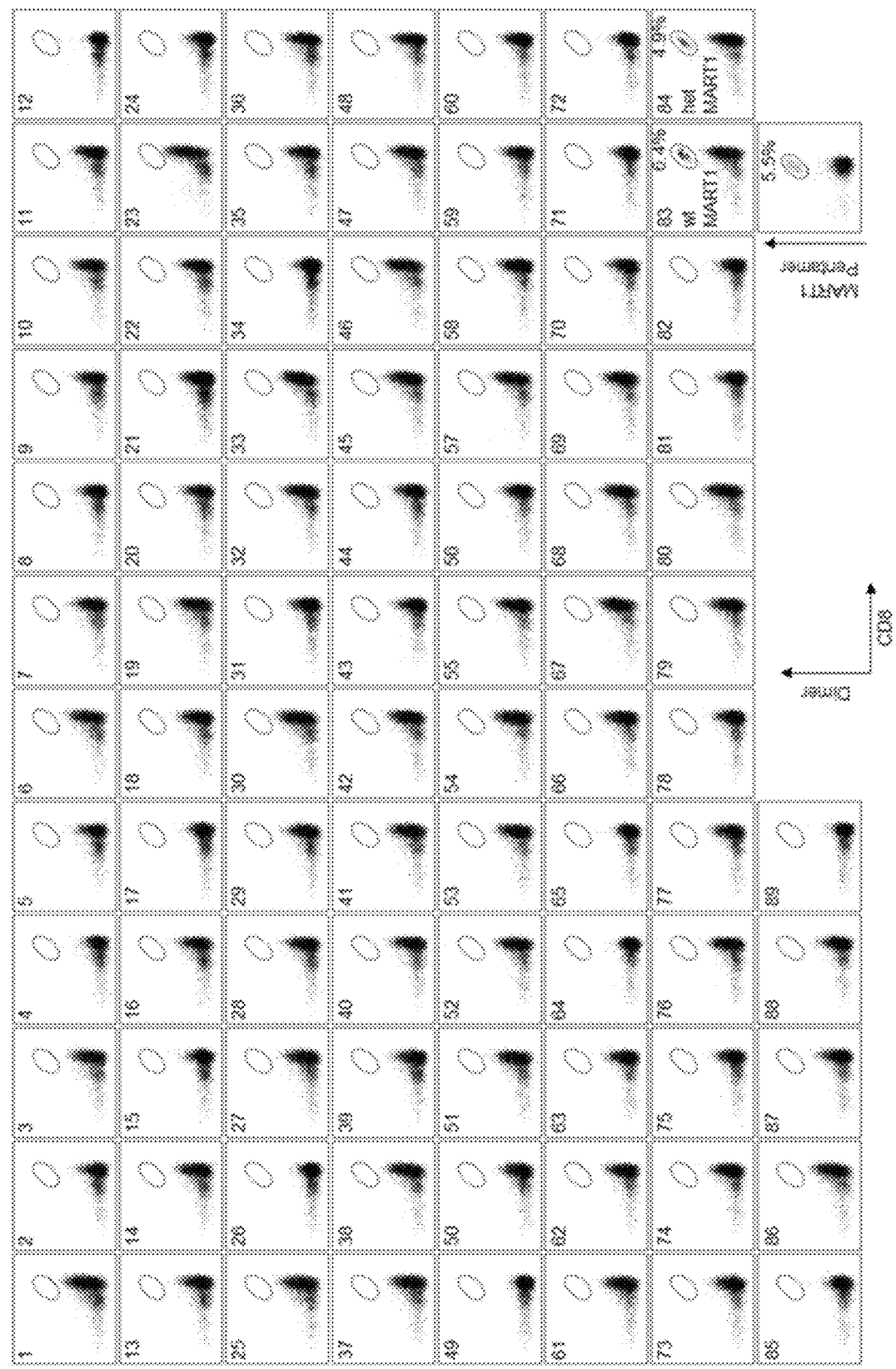
FIG. 16 shows high throughput A2 dimer staining of TILs (TIL:M25 TIL16 REP1 2E7 2016 Sep. 15).
Figure 17:
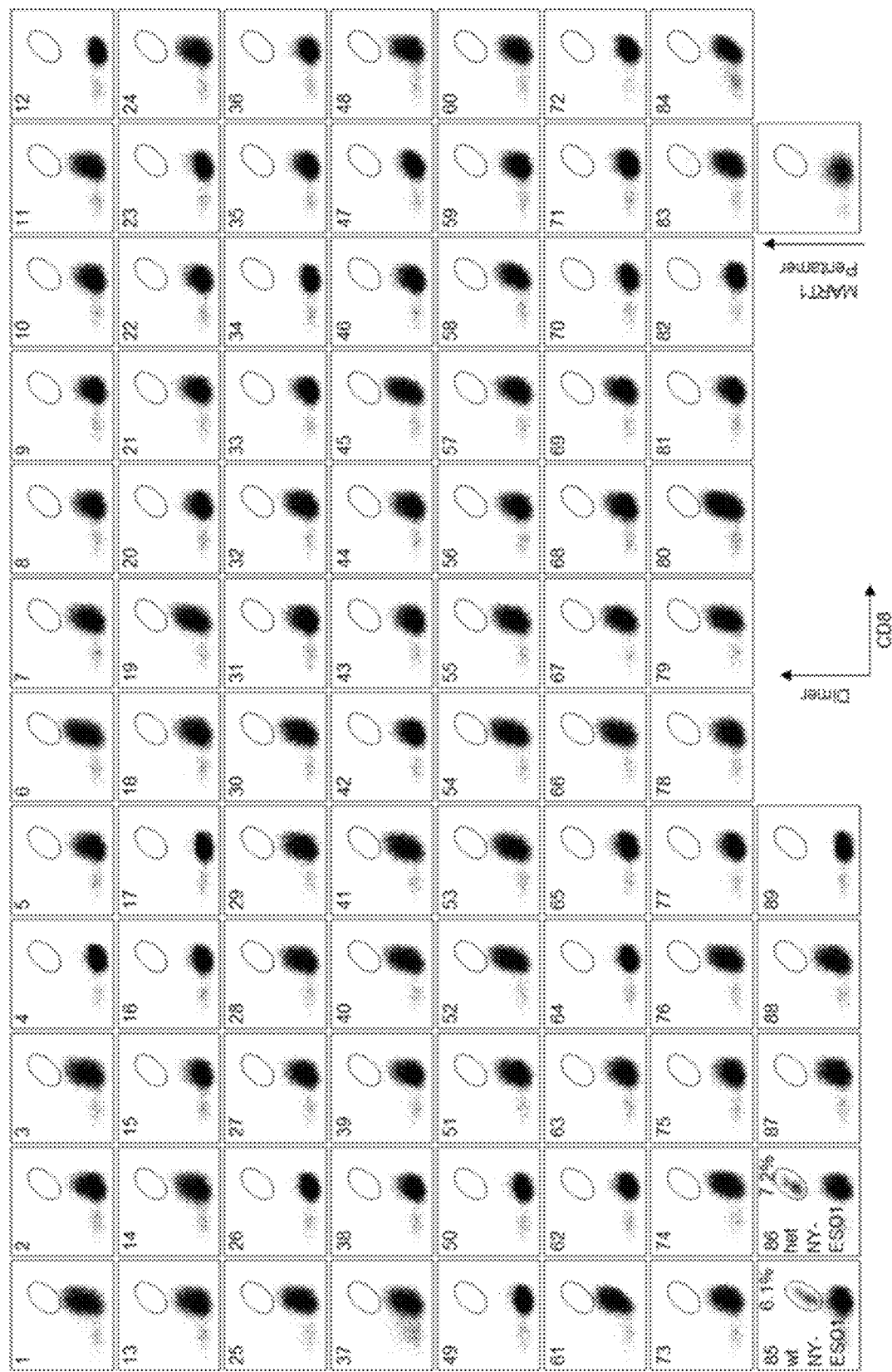
FIG. 17 shows high throughput A2 dimer staining of TILs (TIL:M31 TIL3 REP1A 2E7 2015 Jun. 3).
Figure 18:
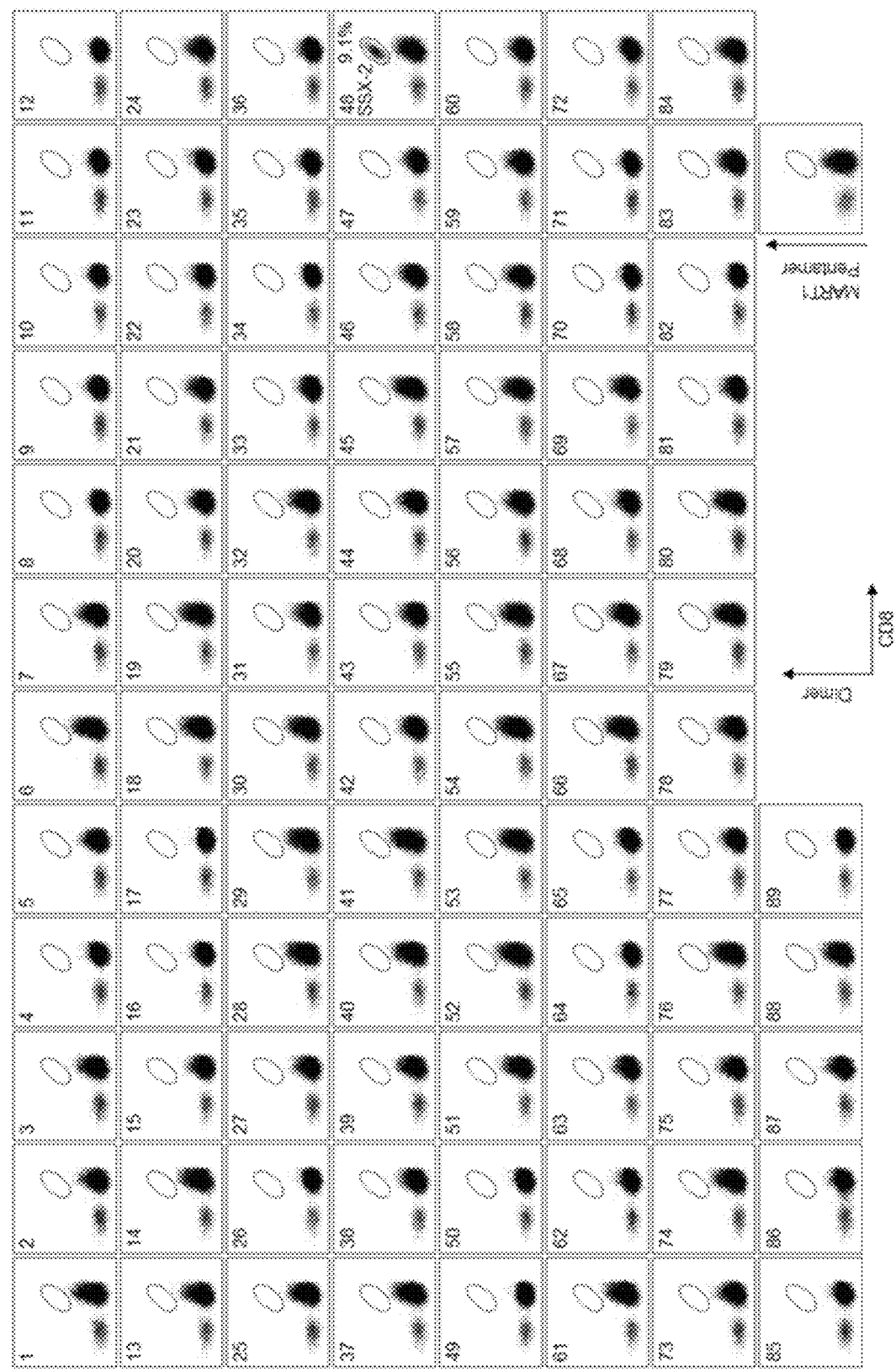
FIG. 18 shows high throughput A2 dimer staining of TILs (TIL:M37 TIL3 REP1B 2E7 2015 Jun. 3).
Figure 19:
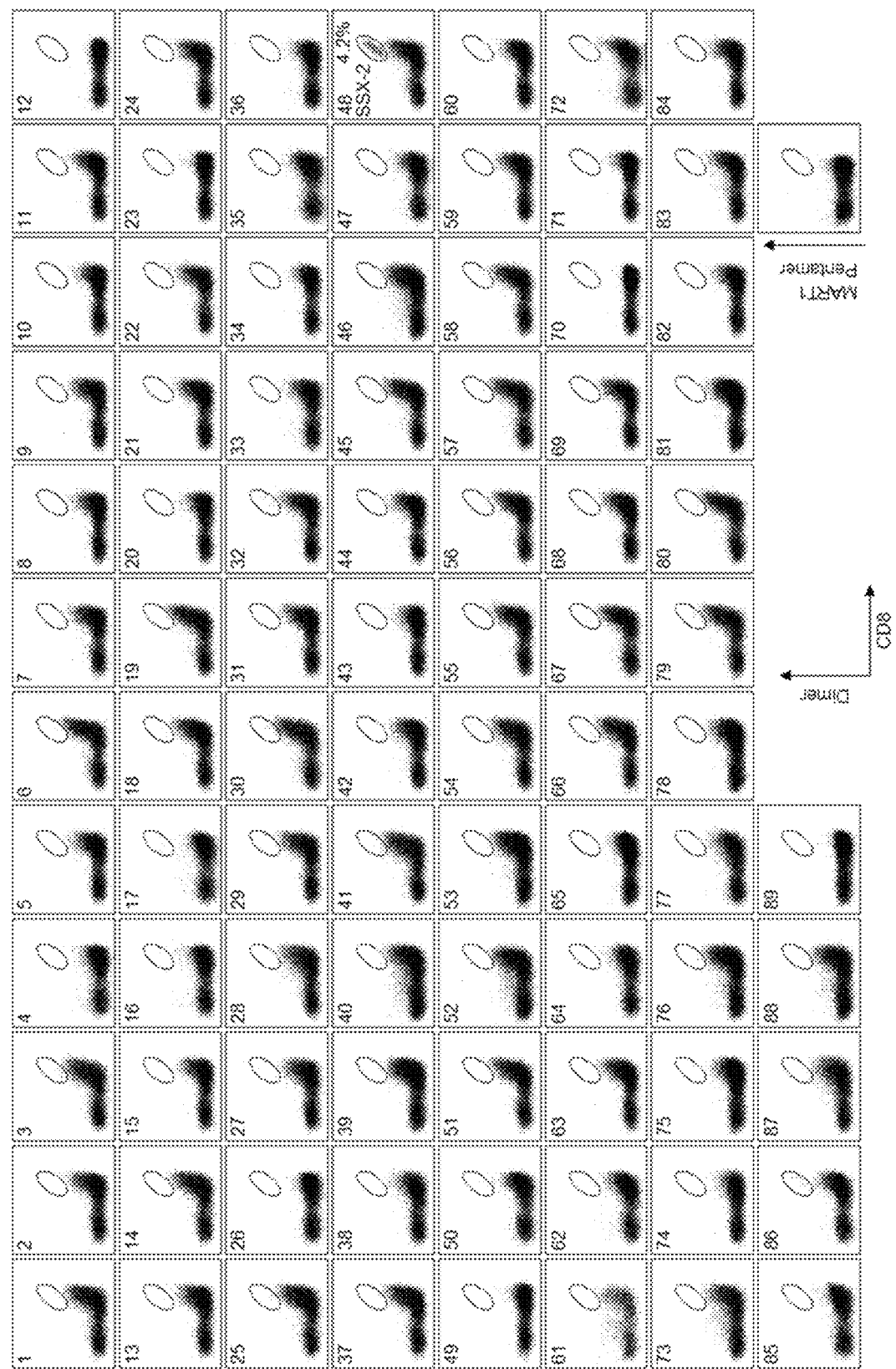
FIG. 19 shows high throughput A2 dimer staining of TILs (TIL:M40 TIL3 REP1A 2E7 2015 Jun. 4).
Figure 20:
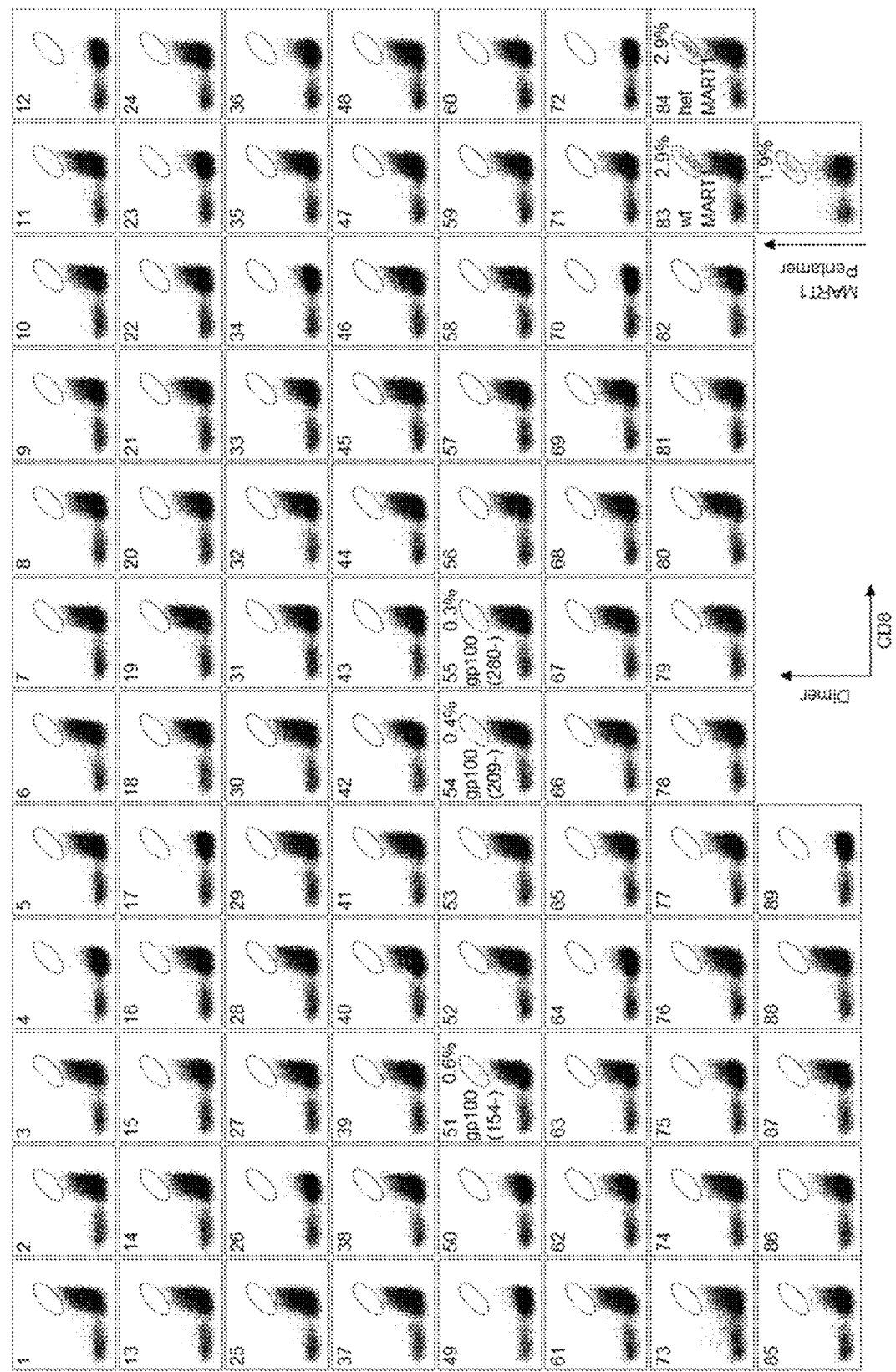
FIG. 20 shows high throughput A2 dimer staining of TILs (TIL:M66 YT REP1A D14 2E7 2012 Feb. 1).
Figure 21:
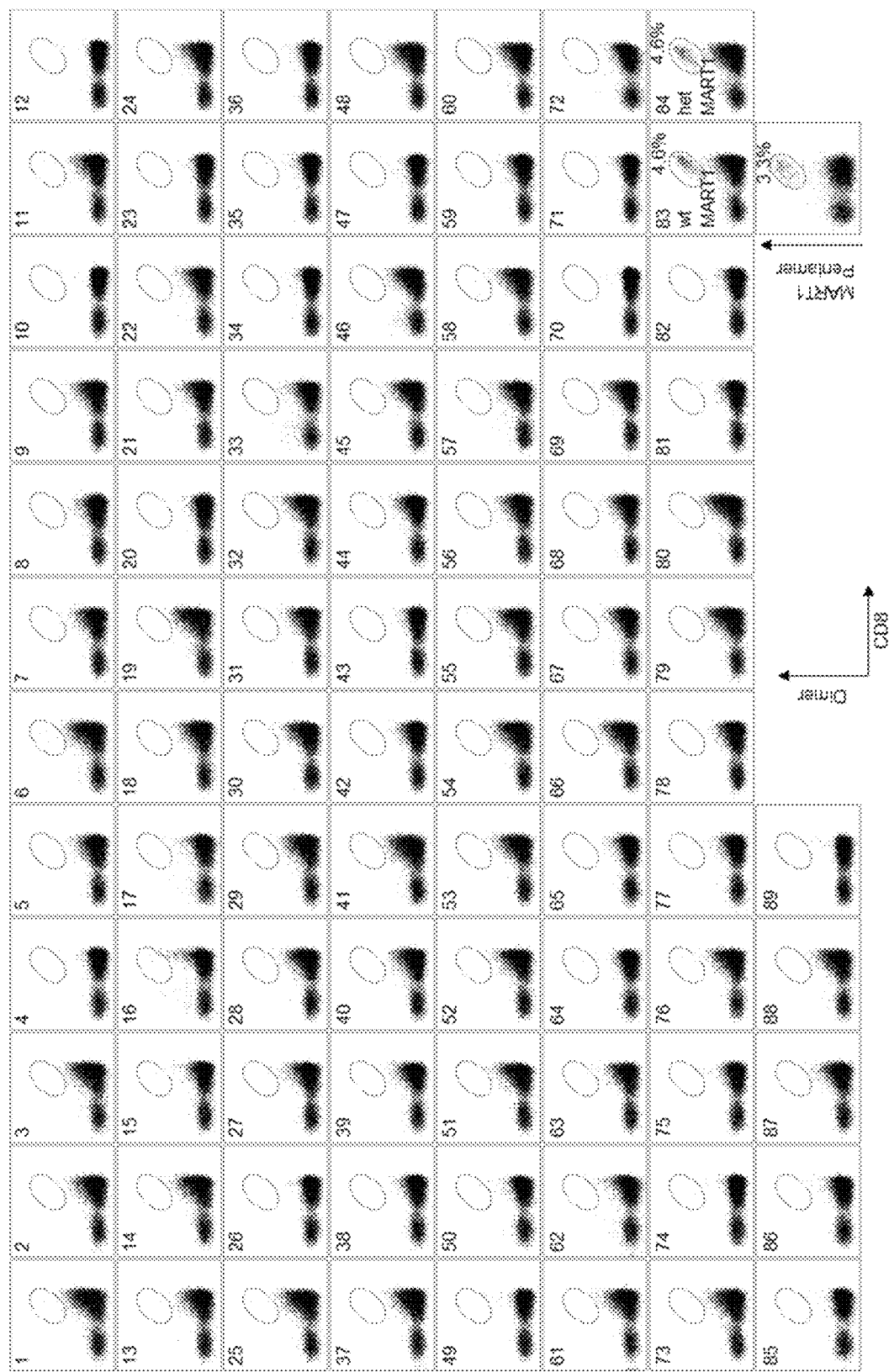
FIG. 21 shows high throughput A2 dimer staining of TILs (TIL:M96 YT REP1A 2E7 2015 Jun. 4).
Figure 22:
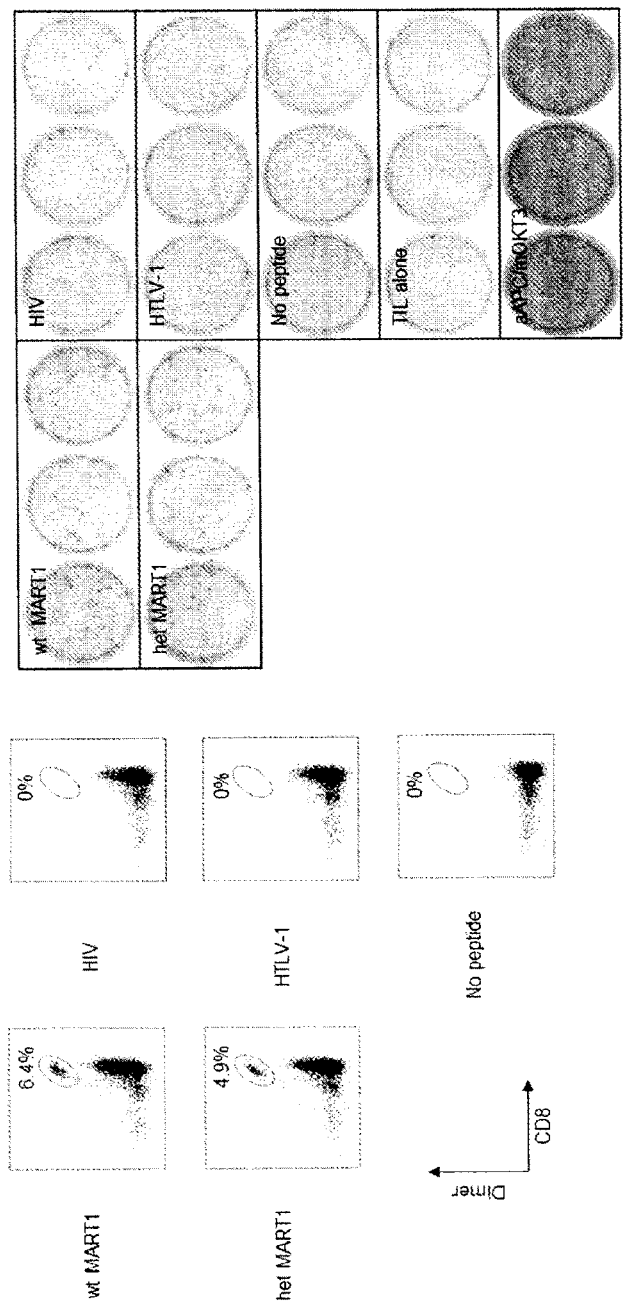
FIG. 22 shows IFN-γ ELISPOT assay (TIL:M25 TIL16 REP1 2E7 2016 Sep. 15).
Figure 23:
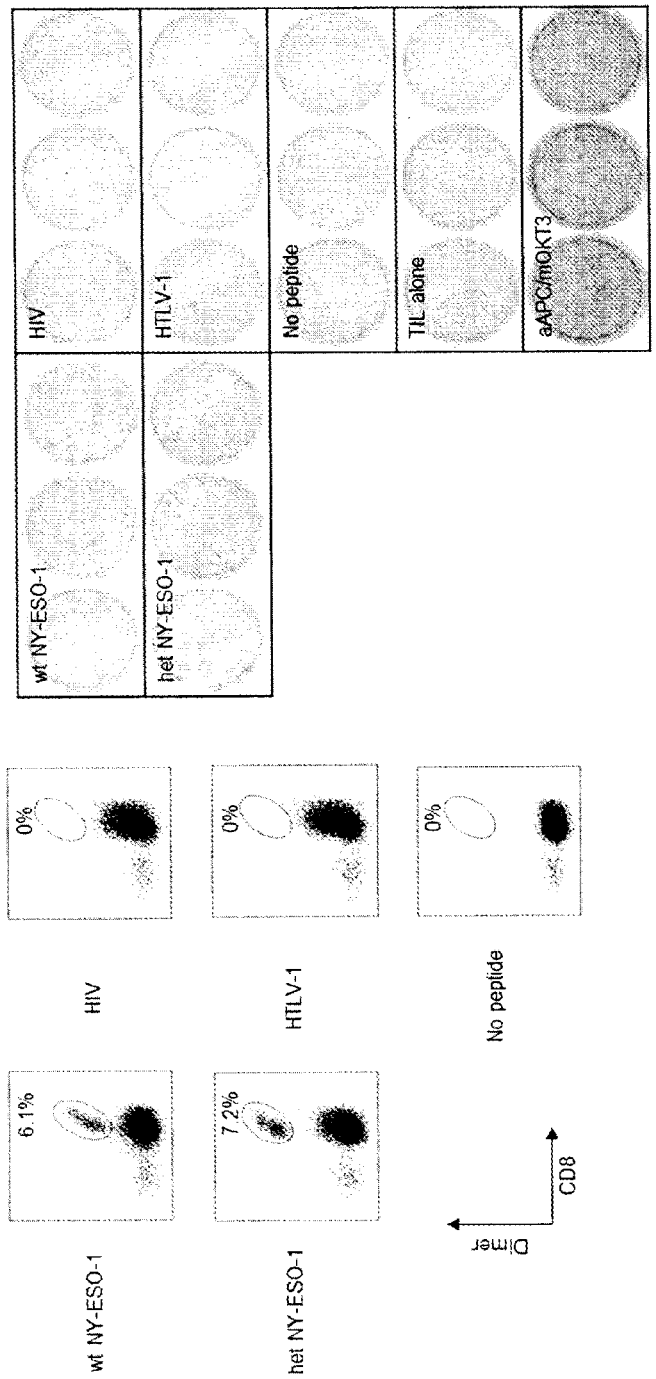
FIG. 23 shows IFN-γ ELISPOT assay (TIL:M31 TIL3 REP1A 2E7 2015 Jun. 3).
Figure 24:
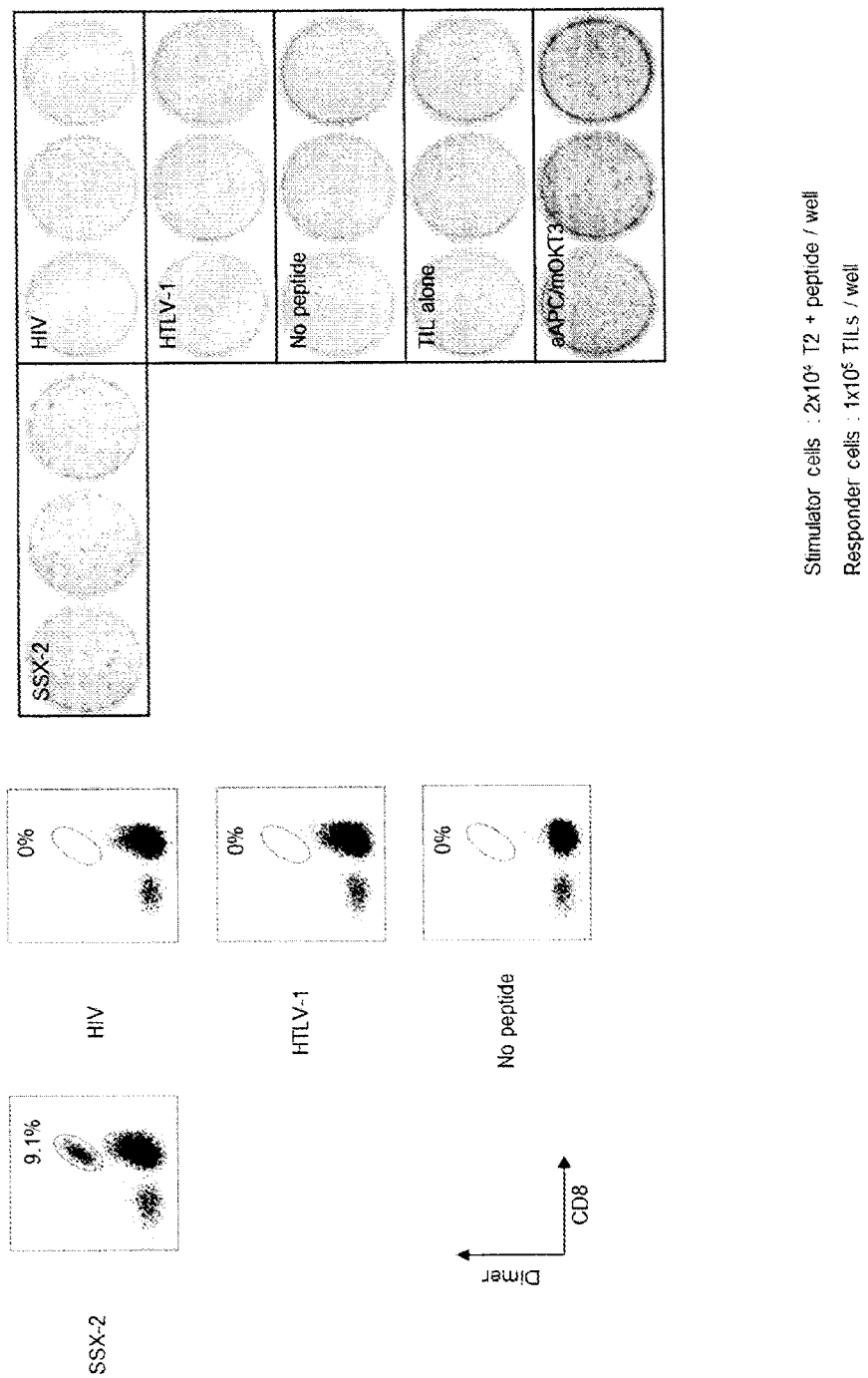
FIG. 24 shows IFN-γ ELISPOT assay (TIL:M37 TIL3 REP1B 2E7 2015 Jun. 3).
Figure 25:
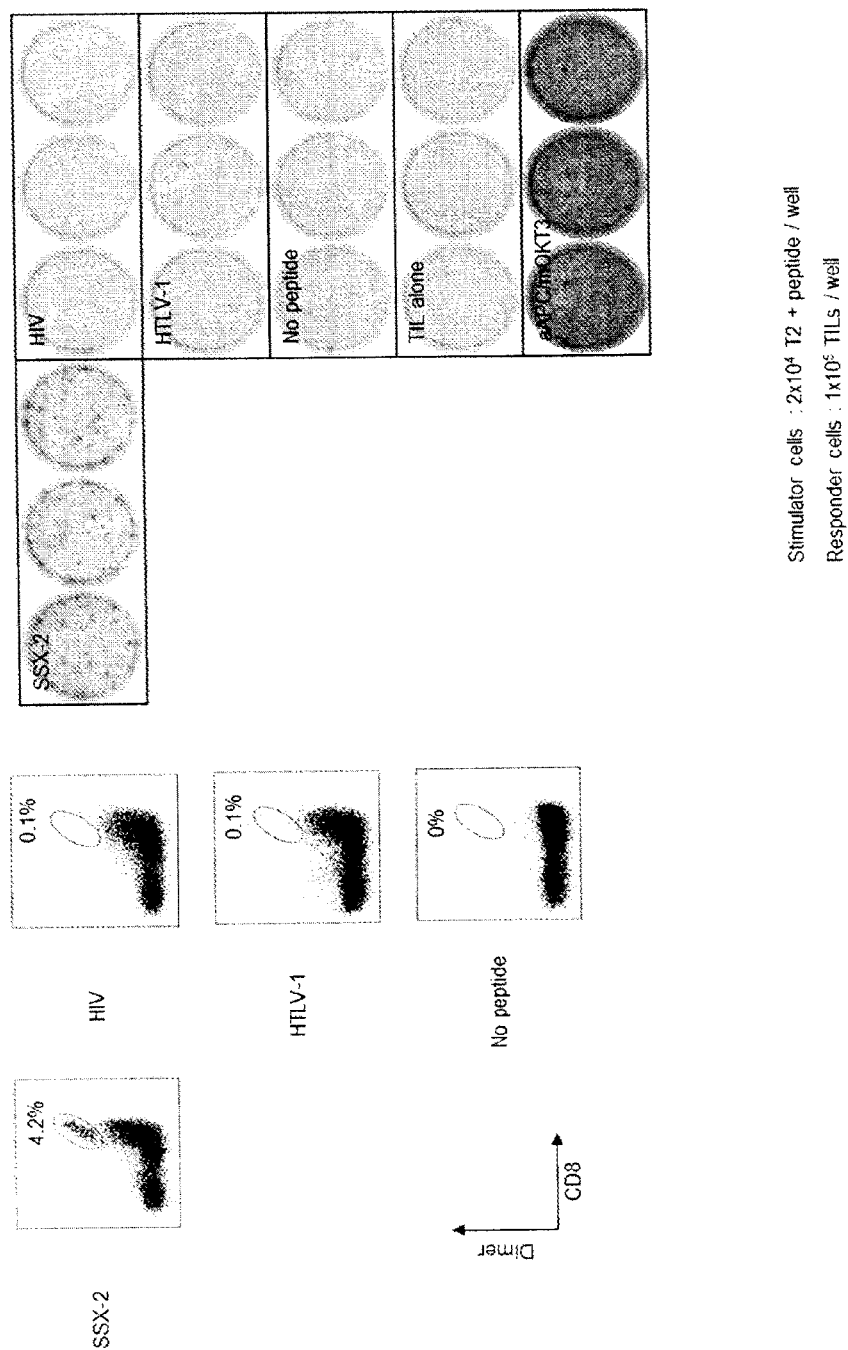
FIG. 25 shows IFN-γ ELISPOT assay (TIL:M40 TIL3 REP1A 2E7 2015 Jun. 4).
Figure 26:
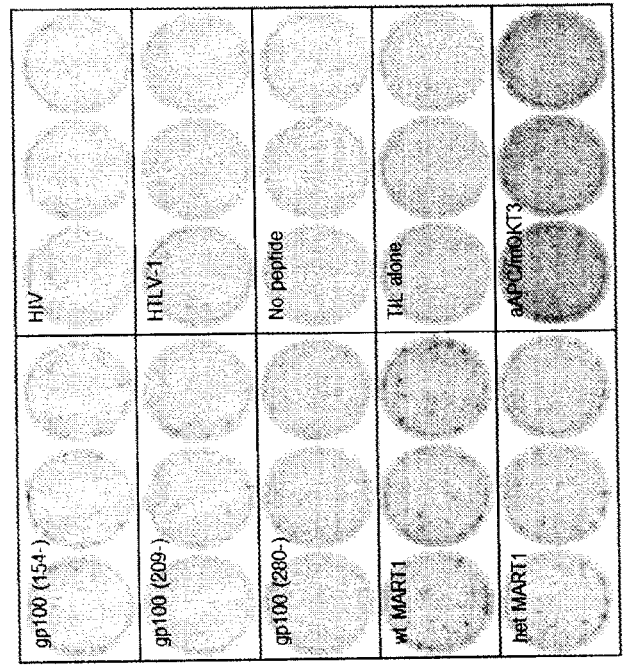
FIG. 26 shows IFN-γ ELISPOT assay (TIL:M66 YT REP1A D14 2E7 2012 Feb. 1).
Figure 26:
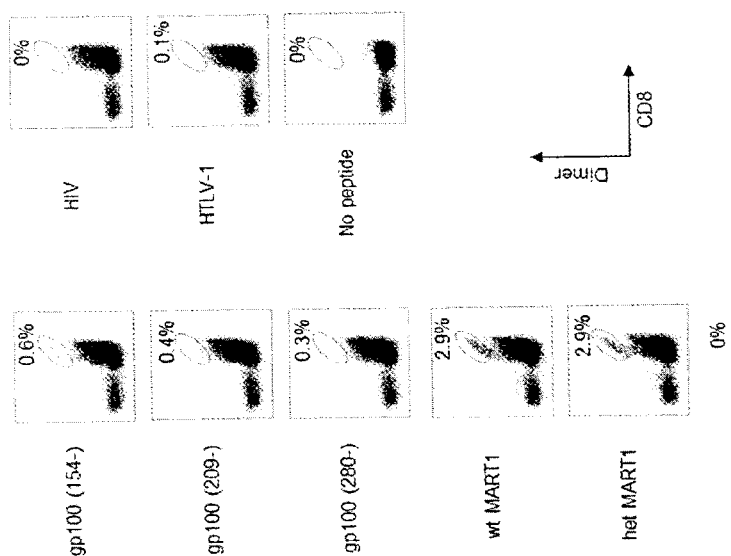
Figure 27:
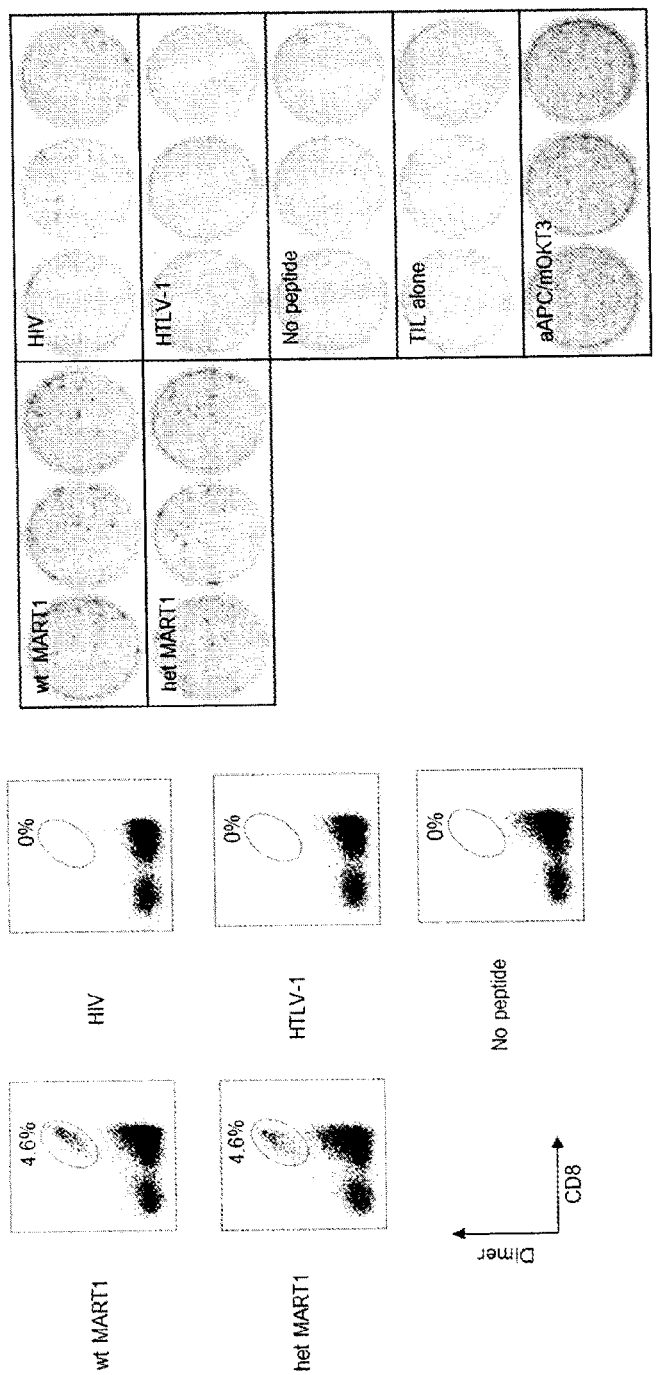
FIG. 27 shows IFN-γ ELISPOT assay (TIL:M96 YT REP1A 2E7 2015 Jun. 4).

Soluble monomeric HLA-C7$^{Q115E}$_K$^b$ was loaded with C7/MAGE-A1$_{289-297}$ (RVRFFFPSL) peptide and C7/MAGE-A12$_{170-178}$ (VRIGHLYIL) peptide, dimerized with PE-conjugated anti-His mAb, and used to stain Jurkat 76/CD8 T cells expressing clonotypic cognate TCR (FIG. 14).

Staining of In Vitro Expanded Tumor-Infiltrating Lymphocytes with a Panel of Soluble A2 Dimers.

Peripheral T cells do not always reflect the immune response to the tumor taking place in cancer patients and antitumor cellular immunity in the periphery does not often correlate with prognosis. In contrast, tumor infiltrating lymphocytes (TILs) interact more closely with the tumor cells and are likely to reflect the tumor host interaction with higher fidelity. The use of TILs as a graft for adoptive cell transfer therapy to treat cancer has been pioneered by Rosenberg's group at the National Cancer Institute in the US[28].

It is believed that TILs are a polyclonal population of T cells with various antigen specificities[29]. To investigate the tumor specificity of TILs using our soluble dimer pHLA technology, TILs were isolated from nine HLA-A2$^+$ patients with metastatic melanoma and grown in vitro as reported previously[14]. A large panel of 8-11 mer peptides derived from proteins highly expressed by autologous tumor cells were predicted using publicly available algorithms as reported previously (see Table 1)[18,23,30]. A library of soluble dimeric A2$^{Q115E}$_K$^b$ loaded with the predicted A2 peptides were produced as described above and used to stain the TILs (see FIG. 12 and FIG. 15-21). A2/HIV pol$_{476-484}$ and A2/MART1$_{26-35}$ Pentamers from ProImmune were utilized as a negative and positive control, respectively. The result showed that the in vitro grown TILs possessed reactivity to MART1, which is one of the well-established melanoma-associated antigen (www.uniprot.org/uniprot/Q16655).

Functional Assays of Dimer$^+$ T Cells

Using ELISPOT assays, A2-restricted peptide-specific IFN-γ secretion was confirmed for all the 6 TIL samples for which dimer staining was positive. PVDF plates (Millipore, Bedford, MA) were coated with capture mAb (1D1K; MABTECH, Mariemont, OH). TILs were incubated with 2×10$^4$ per well of T2 cells in the presence of each peptide for 20-24 hours at 37° C. The plates were washed and incubated with biotin-conjugated detection mAb (7-B6-1; MABTECH). HRP-conjugated SA (Jackson ImmunoResearch) was then added, and IFN-γ spots were developed. The reaction was stopped by rinsing thoroughly with cold tap water. ELISPOT plates were scanned and counted using an ImmunoSpot plate reader and ImmunoSpot version 5.0 software (Cellular Technology Limited, Shaker Heights, OH) (FIG. 22-27).

A Summary of Dimer Staining and ELISPOT Assays of TILs is Shown in FIG. 28.

Figure 29:
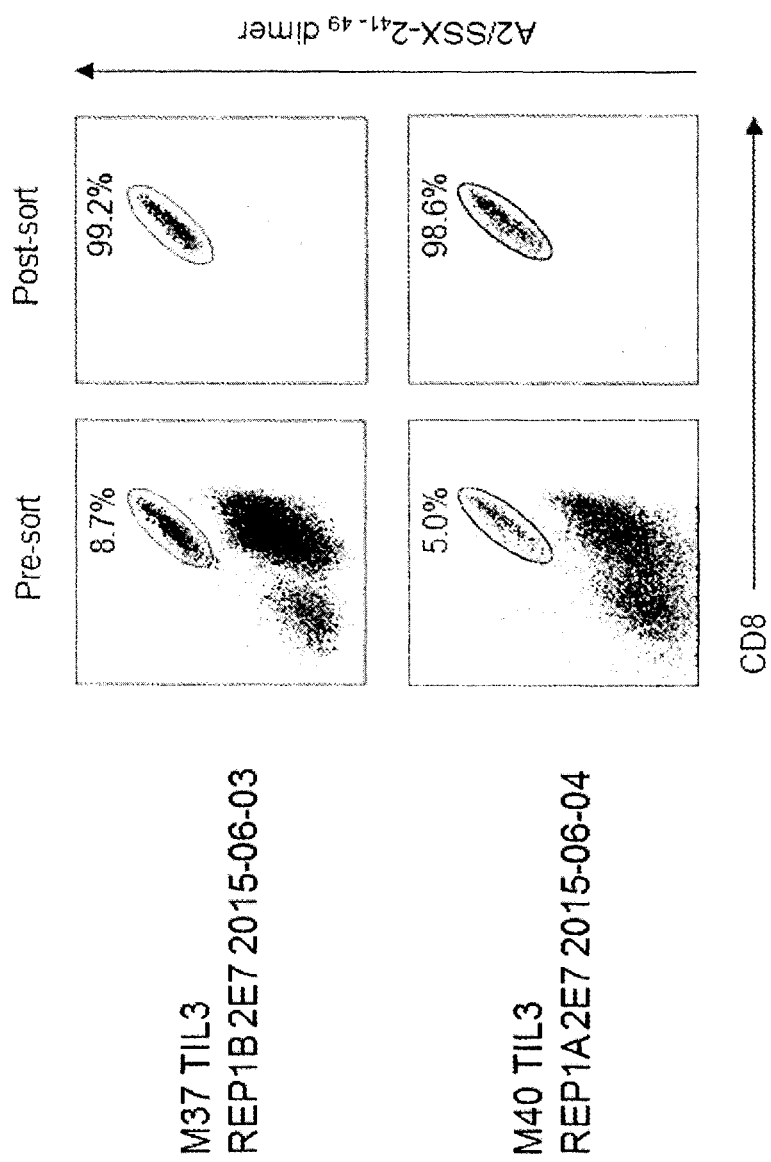
FIG. 29 shows Enrichment of dimer positive TILs.

Two TIL samples (M37 TIL3 REP1B 2E7 2015 Jun. 3 and M40 TIL3 REP1A 2E7 2015 Jun. 4) were stained with A2/SSX-2$_{41-49}$ dimer and A2/SSX-2$_{41-49}$ T cells were purified using flow-cytometry-guided sorting (FIG. 29).

Possible Advantages.

There are a number of possible advantages of the present methods. The present HLA class I molecules may represent a more natural folding and/or glycosylation of the protein. The present HLA molecules might be produced in relatively quick fashion (~ 2 days vs. 4-10 days using conventional methods). Peptides might be exchanged relatively simply in vitro. A simpler protocol resulting in a more natural product might also result in significant cost savings.

Sequences

Soluble A*02:01-Wt. Nucleotide Sequence (SEQ ID NO. 1) and Amino Acid Sequence (SEQ ID NO. 2)

Sequences are listed in the following order:

Signal peptide derived from Fibroin-L (in regular Arial font below)
HLA-A*02:01 α1 domain (underlined below)
**HLA-A*02:01 α2 domain (in bold below)**
*HLA-A*02:01 α3 domain (in italics below)*
<u>Flexible GS linker (in bold and underlined below)</u>
*6×His tag (in bold and italics below)*

```
SEQ ID NO. 1:
ATGATGCGGCCCATCGTGCTGGTGCTGCTGTTTGCCACATCTGCCCTGG

CCGGAAGCCACAGCATGCGGTACTTTTTCACCAGCGTGTCCAGACCCGG

CAGAGGCGAGCCCAGATTCATTGCCGTGGGCTACGTGGACGACACCCAG

TTCGTCAGATTCGACAGCGACGCCGCCAGCCAGCGGATGGAACCTAGAG

CCCCTTGGATCGAGCAGGAAGGCCCCGAGTACTGGGACGGCGAGACACG

GAAAGTGAAGGCCCACAGCCAGACCCACAGAGTGGATCTGGGCACCCTG

CGGGGCTACTACAATCAGTCTGAGGCCGGCTCCCACACCGTGCAGAGGA

TGTACGGCTGTGACGTGGGCAGCGACTGGCGGTTCCTGAGAGGCTACCA

CCAGTACGCCTACGACGGCAAGGACTATATCGCCCTGAAAGAGGACCTG

CGGAGCTGGACAGCCGCCGATATGGCCGCCCAGACCACCAAGCACAAAT

GGGAAGCCGCCCACGTGGCCGAGCAGCTGAGAGCTTATCTGGAAGGCAC

CTGTGTGGAATGGCTGCGGAGATACCTGGAAAACGGCAAAGAGACACTG

CAGCGCACGGACGCCCCCAAAACGCATATGACTCACCACGCTGTCTCTG

ACCATGAAGCCACCCTGAGGTGCTGGGCCCTGAGCTTCTACCCTGCGGA

GATCACACTGACCTGGCAGCGGGATGGGGAGGACCAGACCCAGGACACG

GAGCTCGTGGAGACCAGGCCTGCAGGGGATGGAACCTTCCAGAAGTGGG

CGGCTGTGGTGGTGCCTTCTGGACAGGAGCAGAGATACACCTGCCATGT
```

-continued
GCAGCATGAGGGTTTGCCCAAGCCCCTCACCCTGAGATGGGAGCCGGGC

AGCCACCACCACCATCACCATTGA

SEQ ID NO. 2:
MMRPIVLVLLFATSALAGSHSMRYFFTSVSRPGRGEPRFIAVGYVDDTQ

FVRFDSDAASQRMEPRAPWIEQEGPEYWDGETRKVKAHSQTHRVDLGTL

RGYYNQSEAGSHTVQRMYGCDVGSDWRFLRGYHQYAYDGKDYIALKEDL

RSWTAADMAAQTTKHKWEAAHVAEQLRAYLEGTCVEWLRRYLENGKETL

QRTDAPKTHMTHHAVSDHEATLRCWALSFYPAEFTLTWQRDGEDQTQDT

ELVETRPAGDGTFQKWAAVVVPSGQEQRYTCHVQHEGLPKPLTLRWEFG

GHHHHHHZ

Soluble A*02:01-K$^b$, Nucleotide Sequence (SEQ ID NO. 3) and Amino Acid Sequence (SEQ ID NO. 4)
  Sequences are listed in the following order:
  Signal peptide derived from Fibroin-L (in regular Arial font below)
  HLA-A*02:01 α1 domain (underlined below)
  HLA-A*02:01 α2 domain (in bold below)
  Mouse K$^b$ α3 domain (in italics below)
  Flexible GS linker (in bold and underlined below)
  6×His tag (in bold and italics below)

SEQ ID NO. 3
ATGATGCGGCCCATCGTGCTGGTGCTGCTGTTTGCCACATCTGCCCTGG

CCGGAAGCCACAGCATGCGGTACTTTTTCACCAGCGTGTCCAGACCCGG

CAGAGGCGAGCCCAGATTCATTGCCGTGGGCTACGTGGACGACACCCAG

TTCGTCAGATTCGACAGCGACGCCGCCAGCCAGCGGATGGAACCTAGAG

CCCCTTGGATCGAGCAGGAAGGCCCCGAGTACTGGGACGGCGAGACACG

GAAAGTGAAGGCCCACAGCCAGACCCACAGAGTGGATCTGGGCACCCTG

CGGGGCTACTACAATCAGTCTGAGGCCGGCTCCCACACCGTGCAGAGGA

TGTACGGCTGTGACGTGGGCAGCGACTGGCGGTTCCTGAGAGGCTACCA

CCAGTACGCCTACGACGGCAAGGACTATATCGCCCTGAAAGAGGACCTG

CGGAGCTGGACAGCCGCCGATATGGCCGCCCAGACCACCAAGCACAAAT

GGGAAGCCGCCCACGTGGCCGAGCAGCTGAGAGCTTATCTGGAAGGCAC

CTGTGTGGAATGGCTGCGGAGATACCTGGAAAACGGCAAAGAGACACTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGGC

AGCCACCACCACCATCACCATTGA

SEQ ID NO. 4
MMRPIVLVLLFATSALAGSHSMRYFFTSVSRPGRGEPRFIAVGYVDDTQ

FVRFDSDAASQRMEPRAPWIEQEGPEYWDGETRKVKAHSQTHRVDLGTL

RGYYNQSEAGSHTVQRMYGCDVGSDWRFLRGYHQYAYDGKDYIALKEDL

RSWTAADMAAQTTKHKWEAAHVAEQLRAYLEGTCVEWLRRYLENGKETL

QRTDSPKAHVTHHSRPEDKVTLRCWALGFYPADITLTWQLNGEELIQDM

ELVETRPAGDGTFQKWASVVVPLGKEQYYTCHVYHQGLPEPLTLRWEPG

GHHHHHHZ

Soluble A*02:01$^{Q115E}$-K$^b$. Nucleotide Sequence (SEQ ID NO. 5) and Amino Acid Sequence (SEQ ID NO. 6)
  Sequences are listed in the following order:
  Signal peptide derived from Fibroin-L (in regular Arial font below)
  HLA-A*02:01 α1 domain (underlined below)
  HLA-A*02:01 α2 domain with Q115E mutation (in bold below)
  Mouse K$^b$ α3 domain (in italics below)
  Flexible GS linker (in bold and underlined below)
  6×His tag (in bold and italics below)

SEQ ID NO. 5
ATGATGCGGCCCATCGTGCTGGTGCTGCTGTTTGCCACATCTGCCCTGG

CCGGAAGCCACAGCATGCGGTACTTTTTCACCAGCGTGTCCAGACCCGG

CAGAGGCGAGCCCAGATTCATTGCCGTGGGCTACGTGGACGACACCCAG

TTCGTCAGATTCGACAGCGACGCCGCCAGCCAGCGGATGGAACCTAGAG

CCCCTTGGATCGAGCAGGAAGGCCCCGAGTACTGGGACGGCGAGACACG

GAAAGTGAAGGCCCACAGCCAGACCCACAGAGTGGATCTGGGCACCCTG

CGGGGCTACTACAATCAGTCTGAGGCCGGCTCCCACACCGTGCAGAGGA

TGTACGGCTGTGACGTGGGCAGCGACTGGCGGTTCCTGAGAGGCTACCA

CGAGTACGCCTACGACGGCAAGGACTATATCGCCCTGAAAGAGGACCTG

CGGAGCTGGACAGCCGCCGATATGGCCGCCCAGACCACCAAGCACAAAT

GGGAAGCCGCCCACGTGGCCGAGCAGCTGAGAGCTTATCTGGAAGGCAC

CTGTGTGGAATGGCTGCGGAGATACCTGGAAAACGGCAAAGAGACACTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGGC

AGCCACCACCACCATCACCATTGA

SEQ ID NO. 6
MMRPIVLVLLFATSALAGSHSMRYFFTSVSRPGRGEPRFIAVGYVDDTQ

FVRFDSDAASQRMEPRAPWIEQEGPEYWDGETRKVKAHSQTHRVDLGTL

RGYYNQSEAGSHTVQRMYGCDVGSDWRFLRGYHEYAYDGKDYIALKEDL

RSWTAADMAAQTTKHKWEAAHVAEQLRAYLEGTCVEWLRRYLENGKETL

QRTDSPKAHVTHHSRPEDKVTLRCWALGFYPADITLTWQLNGEELIQDM

ELVETRPAGDGTFQKWASVVVPLGKEQYYTCHVYHQGLPEPLTLRWEPG

GHHHHHHZ

Soluble A*24:02-Wt. Nucleotide Sequence (SEQ ID NO. 7) and Amino Acid Sequence (SEQ ID NO. 8)

Sequences are listed in the following order:
Signal peptide derived from Fibroin-L (in regular Arial font below)
HLA-A*24:02 α1 domain (underlined below)
HLA-A*24:02 α2 domain (in bold below)
HLA-A*24:02 α3 domain (in italics below)
Flexible GS linker (in bold and underlined below)
6×His tag (in bold and italics below)

SEQ ID NO. 7
ATGATGCGGCCCATCGTGCTGGTGCTGCTGTTTGCCACATCTGCCCTGG

CCGGCTCCCACTCCATGAGGTATTTCTCCACATCCGTGTCCCGGCCCGG

CCGCGGGGAGCCCCGCTTCATCGCCGTGGGCTACGTGGACGACACGCAG

TTCGTGCGGTTCGACAGCGACGCCGCGAGCCAGAGGATGGAGCCGCGGG

CGCCGTGGATAGAGCAGGAGGGGCCGGAGTATTGGGACGAGGAGACAGG

GAAAGTGAAGGCCCACTCACAGACTGACCGAGAGAACCTGCGGATCGCG

CTCCGCTACTACAACCAGAGCGAGGCCGGTTCTCACACCCTCCAGATGA

TGTTTGGCTGCGACGTGGGGTCGGACGGGCGCTTCCTCCGCGGGTACCA

CCAGTACGCCTACGACGGCAAGGATTACATCGCCCTGAAAGAGGACCTG

CGCTCTTGGACCGCGGCGGACATGGCGGCTCAGATCACCAAGCGCAAGT

GGGAGGCGGCCCATGTGGCGGAGCAGCAGAGAGCCTACCTGGAGGGCAC

GTGCGTGGACGGGCTCCGCAGATACCTGGAGAACGGGAAGGAGACGCTG

CAG_CGCACGGACCCCCCCAAGACACATATGACCCACCACCCCATCTCTG_

_ACCATGAGGCCACTCTGAGATGCTGGGCCCTGGGCTTCTACCCTGCGGA_

_GATCACACTGACCTGGCAGCGGGATGGGGAGGACCAGACCCAGGACACG_

_GAGCTTGTGGAGACCAGGCCTGCAGGGGATGGAACCTTCCAGAAGTGGG_

_CAGCTGTGGTGGTACCTTCTGGAGAGGAGCAGAGATACACCTGCCATGT_

_GCAGCATGAGGGTCTGCCCAAGCCCCTCACCCTGAGATGGGAGCCG_GGC

AGC_ACCACCACCATCACCAT_TGA

SEQ ID NO. 8
MMRPIVLVLLFATSALAGSHSMRYFSTSVSRPGRGEPRFIAVGYVDDTQ

FVRFDSDAASQRMEPRAPWIEQEGPEYWDEETGKVKAHSQTDRENLRIA

LRYYNQSEAGSHTLQMMFGCDVGSDGRFLRGYHQYAYDGKDYIALKEDL

RSWTAADMAAQITKRKWEAAHVAEQQRAYLEGTCVDGLRRYLENGKETL

Q_RTDPPKTHMTHHPISDHEATLRCWALGFYPAEITLTWQRDGEDQTQDT_

_ELVETRPAGDGTFQKWAAVVVPSGEEQRYTCHVQHEGLPKPLTLRWEP_G

S_HHHHHH_Z

Soluble A*24:02-K^b, Nucleotide Sequence (SEQ ID NO. 9) and Amino Acid Sequence (SEQ ID NO. 10)
Sequences are listed in the following order:
Signal peptide derived from Fibroin-L (in regular Arial font below)
HLA-A*24:02 α1 domain (underlined below)
HLA-A*24:02 α2 domain (in bold below)
Mouse K^b α3 domain (in italics below)
Flexible GS linker (in bold and underlined below)
6×His tag (in bold and italics below)

SEQ ID NO. 9
ATGATGCGGCCCATCGTGCTGGTGCTGCTGTTTGCCACATCTGCCCTGG

CCGGCTCCCACTCCATGAGGTATTTCTCCACATCCGTGTCCCGGCCCGG

CCGCGGGGAGCCCCGCTTCATCGCCGTGGGCTACGTGGACGACACGCAG

TTCGTGCGGTTCGACAGCGACGCCGCGAGCCAGAGGATGGAGCCGCGGG

CGCCGTGGATAGAGCAGGAGGGGCCGGAGTATTGGGACGAGGAGACAGG

GAAAGTGAAGGCCCACTCACAGACTGACCGAGAGAACCTGCGGATCGCG

CTCCGCTACTACAACCAGAGCGAGGCCGGTTCTCACACCCTCCAGATGA

TGTTTGGCTGCGACGTGGGGTCGGACGGGCGCTTCCTCCGCGGGTACCA

CCAGTACGCCTACGACGGCAAGGATTACATCGCCCTGAAAGAGGACCTG

CGCTCTTGGACCGCGGCGGACATGGCGGCTCAGATCACCAAGCGCAAGT

GGGAGGCGGCCCATGTGGCGGAGCAGCAGAGAGCCTACCTGGAGGGCAC

GTGCGTGGACGGGCTCCGCAGATACCTGGAGAACGGGAAGGAGACGCTG

CAG_CGCACAGATTCCCCAAAGGCCCATGTGACCCATCACAGCAGACCTG_

_AAGATAAAGTCACCCTGAGGTGCTGGGCCCTGGGCTTCTACCCTGCTGA_

_CATCACCCTGACCTGGCAGTTGAATGGGGAGGAGCTGATCCAGGACATG_

_GAGCTTGTGGAGACCAGGCCTGCAGGGGATGGAACCTTCCAGAAGTGGG_

_CATCTGTGGTGGTGCCTCTTGGGAAGGAGCAGTATTACACATGCCATGT_

_GTACCATCAGGGGCTGCCTGAGCCCCTCACCCTGAGATGGGAGCCG_GGC

AGC_ACCACCACCATCACCAT_TGA

SEQ ID NO. 10
MMRPIVLVLLFATSALAGSHSMRYFSTSVSRPGRGEPRFIAVGYVDDTQ

FVRFDSDAASQRMEPRAPWIEQEGPEYWDEETGKVKAHSQTDRENLRIA

LRYYNQSEAGSHTLQMMFGCDVGSDGRFLRGYHQYAYDGKDYIALKEDL

RSWTAADMAAQITKRKWEAAHVAEQQRAYLEGTCVDGLRRYLENGKETL

Q_RTDSPKAHVTHHSRPEDKVTLRCWALGFYPADITLTWQLNGEELIQDM_

_ELVETRPAGDGTFQKWASVVVPLGKEQYYTCHVYHQGLPEPLTLRWEP_G

S_HHHHHH_Z

Soluble A*24:029115E_K^b Nucleotide Sequence (SEQ ID NO. 11) and Amino Acid Sequence (SEQ ID NO. 12)
Sequences are listed in the following order:
Signal peptide derived from Fibroin-L (in regular Arial font below)
HLA-A*24:02 α1 domain (underlined below)
HLA-A*24:02 α2 domain with Q115E mutation (in bold below)
Mouse K^b α3 domain (in italics below)
Flexible GS linker (in bold and underlined below)
6×His tag (in bold and italics below)

SEQ ID NO. 11
ATGATGCGGCCCATCGTGCTGGTGCTGCTGTTTGCCACATCTGCCCTGG

CCGGCTCCCACTCCATGAGGTATTTCTCCACATCCGTGTCCCGGCCCGG

CCGCGGGGAGCCCCGCTTCATCGCCGTGGGCTACGTGGACGACACGCAG

TTCGTGCGGTTCGACAGCGACGCCGCGAGCCAGAGGATGGAGCCGCGGG

CGCCGTGGATAGAGCAGGAGGGGCCGGAGTATTGGGACGAGGAGACAGG

-continued
GAAAGTGAAGGCCCACTCACAGACTGACCGAGAGAACCTGCGGATCGCG

CTCCGCTACTACAACCAGAGCGAGGCCGGTTCTCACACCCTCCAGATGA

TGTTTGGCTGCGACGTGGGGTCGGACGGGCGCTTCCTCCGCGGGTACCA

CGAGTACGCCTACGACGGCAAGGATTACATCGCCCTGAAAGAGGACCTG

CGCTCTTGGACCGCGGCGGACATGGCGGCTCAGATCACCAAGCGCAAGT

GGGAGGCGGCCCATGTGGCGGAGCAGCAGAGAGCCTACCTGGAGGGCAC

*GTGCGTGGACGGGCTCCGCAGATACCTGGAGAACGGGAAGGAGACGCTG*

*CAGCGCACAGATTCCCCAAAGGCCCATGTGACCCATCACAGCAGACCTG*

*AAGATAAAGTCACCCTGAGGTGCTGGGCCCTGGGCTTCTACCCTGCTGA*

*CATCACCCTGACCTGGCAGTTGAATGGGGAGGAGCTGATCCAGGACATG*

*GAGCTTGTGGAGACCAGGCCTGCAGGGGATGGAACCTTCCAGAAGTGGG*

*CATCTGTGGTGGTGCCTCTTGGGAAGGAGCAGTATTACACATGCCATGT*

*GTACCATCAGGGGCTGCCTGAGCCCCTCACCCTGAGATGGGAGCC*GGC

AG*C*CACCACCACCATCACCATTGA

SEQ ID NO. 12
MMRPIVLVLLFATSALAGSHSMRYFSTSVSRPGRGEPRFIAVGYVDDTQ

FVRFDSDAASQRMEPRAPWIEQEGPEYWDEETGKVKAHSQTDRENLRIA

LRYYNQSEAGSHTLQMMFGCDVGSDGRFLRGYHEYAYDGKDYIALKEDL

RSWTAADMAAQITKRKWEAAHVAEQQRAYLEGTCVDGLRRYLENGKETL

Q*RTDSPKAHVTHHSRPEDKVTLRCWALGFYPADSTLTWQLNGEELSQDM*

*ELVETRPAGDGTFQKWASVVVPLGKEQYYTCHVYHQGLPEPLTLRWEP*G

S*HHHHHH*Z

Soluble B*35:019115E-K$^b$, Nucleotide Sequence (SEQ ID NO. 13) and Amino Acid Sequence (SEQ ID NO. 14)
  Sequences are listed in the following order:
  Signal peptide derived from Fibroin-L (in regular Arial font below)
  HLA-B*35:01 α1 domain (underlined below)
  HLA-B*35:01 α2 domain with Q115E mutation (in bold below)
  Mouse K$^b$ α3 domain (in italics below)
  Flexible GS linker (in bold and underlined below)
  6×His tag (in bold and italics below)

SEQ ID NO. 13
ATGATGCGGCCCATCGTGCTGGTGCTGCTGTTTGCCACATCTGCCCTGG

CCGGCTCCCACTCCATGAGGTATTTCTACACCGCCATGTCCCGGCCCGG

CCGCGGGGAGCCCCGCTTCATCGCAGTGGGCTACGTGGACGACACCCAG

TTCGTGAGGTTCGACAGCGACGCCGCGAGTCCGAGGACGGAGCCCCGGG

CGCCATGGATAGAGCAGGAGGGGCCGGAGTATTGGGACCGGAACACACA

GATCTTCAAGACCAACACACAGACTTACCGAGAGAGCCTGCGGAACCTG

CGCGGCTACTACAACCAGAGCGAGGCCGGGTCTCACATCATCCAGAGGA

TGTATGGCTGCGACCTGGGGCCCGACGGGCGCCTCCTCCGCGGGCATGA

CGAGTCCGCCTACGACGGCAAGGATTACATCGCCCTGAACGAGGACCTG

AGCTCCTGGACCGCGGCGGACACCGCGGCTCAGATCACCCAGCGCAAGT

GGGAGGCGGCCCGTGTGGCGGAGCAGCTGAGAGCCTACCTGGAGGGCCT

GTGCGTGGAGTGGCTCCGCAGATACCTGGAGAACGGGAAGGAGACGCTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGC

AG*C*ACCACCACCATCACCATTGA

SEQ ID NO. 14
MMRPIVLVLLFATSALAGSHSMRYFYTAMSRPGRGEPRFIAVGYVDDTQ

FVRFDSDAASPRTEPRAPWIEQEGPEYWDRNTQIFKTNTQTYRESLRNL

RGYYNQSEAGSHIIQRMYGCDLGPDGRLLRGHDESAYDGKDYIALNEDL

SSWTAADTAAQITQRKWEAARVAEQLRAYLEGLCVEWLRRYLENGKETL

Q*RTDSPKAHVTHHSRPEDKVTLRCWALGFYPADITLTWQLNGEELIQDM*

*ELVETRPAGDGTFQKWASVVVPLGKEQYYTCHVYHQGLPEPLTLRWEP*G

S*HHHHHH*Z

Soluble B*40:029115E-K$^b$. Nucleotide Sequence (SEQ ID NO. 15) and Amino Acid Sequence (SEQ ID NO. 16)
  Sequences are listed in the following order:
  Signal peptide derived from Fibroin-L (in regular Arial font below)
  HLA-B*40:02 α1 domain (underlined below)
  HLA-B*40:02 α2 domain with Q115E mutation (in bold below)
  Mouse K$^b$ α3 domain (in italics below)
  Flexible GS linker (in bold and underlined below)
  6×His tag (in bold and italics below)

SEQ ID NO. 15
ATGATGCGGCCCATCGTGCTGGTGCTGCTGTTTGCCACATCTGCCCTGG

CCGGCAGCCACAGCATGCGGTACTTCCACACCAGCGTGTCCAGACCCGG

AAGAGGCGAGCCCAGATTCATCACCGTGGGCTACGTGGACGACACCCTG

TTCGTCAGATTCGACAGCGACGCCACCAGCCCCCGGAAAGAACCTAGAG

CCCCTTGGATCGAGCAGGAAGGCCCCGAGTACTGGGACAGAGAGACACA

GATCAGCAAGACCAACACCCAGACCTACAGAGAGAGCCTGCGGAACCTG

CGGGGCTACTACAATCAGAGCGAGGCCGGCTCTCACACCCTGCAGTCTA

TGTACGGCTGCGACGTGGGCCCCGATGGCAGACTGCTGAGAGGCCACAA

CGAGTACGCCTACGACGGCAAGGACTATATCGCCCTGAACGAGGACCTG

CGGAGCTGGACAGCCGCCGATACAGCCGCCCAGATCACCCAGAGAAAGT

GGGAGGCCGCCAGAGTGGCCGAACAGCTGAGAGCCTATCTGGAAGGCGA

GTGCGTGGAATGGCTGCGGAGATACCTGGAAAACGGCAAAGAGACACTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

-continued
CATCTGTGGTGGTGCCTCTTGGGAAGGAGCAGTATTACACATGCCATGT

GTACCATCAGGGGCTGCCTGAGCCCCTCACCCTGAGATGGGAGCCGGGC

AGCCACCACCACCATCACCATTGA

SEQ ID NO. 16
MMRPIVLVLLFATSALAGSHSMRYFHTSVSRPGRGEPRFITVGYVDDTL

FVRFDSDATSPRKEPRAPWIEQEGPEYWDRETQISKTNTQTYRESLRNL

RGYYNQSEAGSHTLQSMYGCDVGPDGRLLRGHNEYAYDGKDYIALNEDL

RSWTAADTAAQITQRKWEAARVAEQLRAYLEGECVEWLRRYLENGKETL

QRTDSPKAHVTHHSRPEDKVTLRCWALGFYPADITLTWQLNGEELIQDM

ELVETRPAGDGTFQKWASVVVPLGKEQYYTCHVYHQGLPEPLTLRWEPG

SHHHHHHZ

Soluble B*44:059115E-K$^b$, Nucleotide Sequence (SEQ ID NO. 17) and Amino Acid Sequence (SEQ ID NO. 18)
Sequences are listed in the following order:
Signal peptide derived from Fibroin-L (in regular Arial font below)
HLA-B*44:05 α1 domain (underlined below)
HLA-B*44:05 α2 domain with Q115E mutation (in bold below)
Mouse K$^b$ α3 domain (in italics below)
Flexible GS linker (in bold and underlined below)
6×His tag (in bold and italics below)

SEQ ID NO. 17
ATGATGAGGCCCATCGTGCTGGTGCTGCTGTTCGCCACATCTGCCCTGG

CCGGCAGCCACAGCATGCGGTACTTTTACACCGCCATGAGCAGACCCGG

CAGAGGCGAGCCCAGATTCATCACCGTGGGCTACGTGGACGACACCCTG

TTCGTCAGATTCGACAGCGACGCCACCAGCCCCCGGAAAGAACCTAGAG

CCCCTTGGATCGAGCAGGAAGGCCCCGAGTACTGGGACAGAGAGACACA

GATCAGCAAGACCAACACCCAGACCTACAGAGAGAACCTGCGGACCGCC

CTGCGGTACTACAATCAGTCTGAGGCCGGCTCCCACATCATCCAGCGGA

TGTACGGCTGTGACGTGGGCCCCGATGGCAGACTGCTGAGAGGCTACGA

CGAGTACGCCTACGACGGCAAGGACTATATCGCCCTGAACGAGGACCTG

AGCAGCTGGACAGCCGCCGATACAGCCGCCCAGATCACCCAGAGAAAGT

GGGAGGCCGCCAGAGTGGCCGAGCAGGATAGAGCCTATCTGGAAGGCCT

GTGCGTGGAAAGCCTGCGGAGATACCTGGAAAACGGCAAAGAGACACTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGGC

AGCCACCACCACCATCACCATTGA

SEQ ID NO. 18
MMRPIVLVLLFATSALAGSHSMRYFYTAMSRPGRGEPRFITVGYVDDTL

FVRFDSDATSPRKEPRAPWIEQEGPEYWDRETQISKTNTQTYRENLRTA

-continued
LRYYNQSEAGSHIIQRMYGCDVGPDGRLLRGYDEYAYDGKDYIALNEDL

SSWTAADTAAQITQRKWEAARVAEQDRAYLEGLCVESLRRYLENGKETL

QRTDSPKAHVTHHSRPEDKVTLRCWALGFYPADFTLTWQLNGEELIQDM

ELVETRPAGDGTFQKWASVVVPLGKEQYYTCHVYHQGLPEPLTLRWEPG

SHHHHHHZ

Soluble B*07:029115E-K$^b$, Nucleotide Sequence (SEQ ID NO. 19) and Amino Acid Sequence (SEQ ID NO. 20)
Sequences are listed in the following order:
Signal peptide derived from Fibroin-L (in regular Arial font below)
HLA-B*07:02 α1 domain (underlined below)
HLA-B*07:02 α2 domain with Q115E mutation (in bold below)
Mouse K$^b$ α3 domain (in italics below)
Flexible GS linker (in bold and underlined below)
6×His tag (in bold and italics below)

SEQ ID NO. 19
ATGATGCGGCCCATCGTGCTGGTGCTGCTGTTTGCCACATCTGCCCTGG

CCGGCAGCCACAGCATGCGGTACTTTTACACCAGCGTGTCCAGACCCGG

CAGAGGCGAGCCCAGATTCATCAGCGTGGGCTACGTGGACGACACCCAG

TTCGTCAGATTCGACAGCGACGCCGCCAGCCCCAGAGAGGAACCTAGAG

CCCCTTGGATCGAGCAGGAAGGCCCCGAGTACTGGGACCGGAACACCCA

GATCTACAAGGCCCAGGCCCAGACCGACAGAGAGAGCCTGAGAAACCTG

CGGGGCTACTACAACCAGAGCGAGGCCGGCTCTCACACCCTGCAGTCTA

TGTACGGCTGCGACGTGGGCCCCGATGGCAGACTGCTGAGAGGCCACGA

TGAGTACGCCTACGACGGCAAGGACTATATCGCCCTGAACGAGGACCTG

CGGAGCTGGACAGCCGCCGATACAGCCGCCCAGATCACCCAGAGAAAGT

GGGAGGCCGCCAGAGAGGCCGAACAGAGAAGGGCCTATCTGGAAGGCGA

GTGCGTGGAATGGCTGCGGAGATACCTGGAAAATGGCAAGGACAAGCTG

GAACGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGGC

AGCCACCACCACCATCACCATTGA

SEQ ID NO. 20
MMRPIVLVLLFATSALAGSHSMRYFYTSVSRPGRGEPRFISVGYVDDTQ

FVRFDSDAASPREEPRAPWIEQEGPEYWDRNTQIYKAQAQTDRESLRNL

RGYYNQSEAGSHTLQSMYGCDVGPDGRLLRGHDEYAYDGKDYIALNEDL

RSWTAADTAAQITQRKWEAAREAEQRRAYLEGECVEWLRRYLENGKDKL

ERTDSPKAHVTHHSRPEDKVTLRCWALGFYPADFFLTWQLNGEELIQDM

ELVETRPAGDGTFQKWASVVVPLGKEQYYTCHVYHQGLPEPLTLPWEPG

SHHHHHHZ

Soluble B*08:019115E-K$^b$, Nucleotide Sequence (SEQ ID NO. 21) and Amino Acid Sequence (SEQ ID NO. 22)

Sequences are listed in the following order:
Signal peptide derived from Fibroin-L (in regular Arial font below)
HLA-B*08:01 α1 domain (underlined below)
HLA-B*08:01 α2 domain with Q115E mutation (in bold below)
Mouse K$^b$ α3 domain (in italics below)
Flexible GS linker (in bold and underlined below)
6×His tag (in bold and italics below)

SEQ ID NO. 21
ATGATGCGGCCCATCGTGCTGGTGCTGCTGTTTGCCACATCTGCCCTGG

CCGGCAGCCACAGCATGCGGTACTTTGACACCGCCATGAGCAGACCCGG

CAGAGGCGAGCCCAGATTCATCAGCGTGGGCTACGTGGACGACACCCAG

TTCGTCAGATTCGACAGCGACGCCGCCAGCCCCAGAGAGGAACCTAGAG

CCCCTTGGATCGAGCAGGAAGGCCCCGAGTACTGGGACCGGAACACCCA

GATCTTCAAGACCAATACCCAGACCGACAGAGAGAGCCTGCGGAACCTG

CGGGGCTACTACAATCAGAGCGAGGCCGGCTCTCACACCCTGCAGTCTA

TGTACGGCTGCGACGTGGGCCCCGATGGCAGACTGCTGAGAGGCCACAA

CGAGTACGCCTACGACGGCAAGGACTATATCGCCCTGAACGAGGACCTG

CGGAGCTGGACAGCCGCCGATACAGCCGCCCAGATCACCCAGAGAAAGT

GGGAGGCCGCCAGAGTGGCCGAGCAGGATAGAGCCTACCTGGAAGGCAC

CTGTGTGGAATGGCTGCGGAGATACCTGGAAAATGGCAAGGACACCCTG

GAACGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGGC

AGC*CACCACCACCATCACCAT*TGA

SEQ ID NO. 22
MMRPIVLVLLFATSALAGSHSMRYFDTAMSRPGRGEPRFISVGYVDDTQ

FVRFDSDAASPREEPRAPWIEQEGPEYWDRNTQIFKTNTQTDRESLRNL

RGYYNQSEAGSHTLQSMYGCDVGPDGRLLRGHNEYAYDGKDYIALNEDL

RSWTAADTAAQITQRKWEAARVAEQDRAYLEGTCVEWLRRYLENGKDTL

ERTDSPKAHVTHHSRPEDKVTLRCWALGFYPADFFLTWQLNGEELIQDM

ELVETRPAGDGTFQKWASVVVPLGKEQYYTCHVYHQGLPEPLTLPWEPG

SHHHHHZ

Soluble C*05:019115E-K$^b$, Nucleotide Sequence (SEQ ID NO. 23) and Amino Acid Sequence (SEQ ID NO. 24)
Sequences are listed in the following order:
Signal peptide derived from Fibroin-L (in regular Arial font below)
HLA-C*05:01 α1 domain (underlined below)
HLA-C*05:01 α2 domain with Q115E mutation (in bold below)
Mouse K$^b$ α3 domain (in italics below)
Flexible GS linker (in bold and underlined below)
6×His tag (in bold and italics below)

SEQ ID NO. 23
ATGATGCGGCCCATCGTGCTGGTGCTGCTGTTTGCCACAAGCGCCCTGG

CCTGCTCTCACAGCATGCGCTATTTTTACACGGCAGTTAGTCGGCCTGG

GAGGGGTGAGCCGAGATTCATTGCTGTAGGCTACGTAGACGACACTCAA

TTTGTACAGTTCGACTCAGACGCTGCTTCACCGCGAGGAGAGCCCAGGG

CACCCTGGGTAGAACAAGAAGGGCCCGAATACTGGGATCGAGAAAGCCA

GAAGTATAAGAGGCAAGCACAAACTGATCGGGTCAACTTGAGAAAACTG

CGAGGCTACTATAATCAAAGTGAGGCAGGATCCCATACACTTCAGAGGA

TGTATGGCTGCGACCTTGGTCCAGATGGCCGGCTCCTCAGAGGGTATAA

CGAATTTGCATACGACGGGAAGGATTACATAGCTCTCAATGAGGACCTT

AGATCATGGACGGCAGCGGATAAGGCAGCCCAAATTACTCAAAGGAAAT

GGGAGGCGGCCCGAGAAGCAGAGCAGAGAAGAGCCTACCTGGAAGGTAC

ATGCGTGGAGTGGCTTCGCGCTATCTCGAAAACGGTAAAAAGACATTG

CAA*CGCACAGATTCCCCAAAGGCCCATGTGACCCATCACAGCAGACCTG*

*AAGATAAAGTCACCCTGAGGTGCTGGGCCCTGGGCTTCTACCCTGCTGA*

*CATCACCCTGACCTGGCAGTTGAATGGGGAGGAGCTGATCCAGGACATG*

*GAGCTTGTGGAGACCAGGCCTGCAGGGGATGGAACCTTCCAGAAGTGGG*

*CATCTGTGGTGGTGCCTCTTGGGAAGGAGCAGTATTACACATGCCATGT*

*GTACCATCAGGGGCTGCCTGAGCCCCTCACCCTGAGATGGGAGCC*GGGC

AGC*CACCACCACCATCACCAT*TGA

SEQ ID NO. 24
MMRPIVLVLLFATSALACSHSMRYFYTAVSRPGRGEPRFIAVGYVDDTQ

FVQFDSDAASPRGEPRAPWVEQEGPEYWDRETQKYKRQAQTDRVNLRKL

RGYYNQSEAGSHTLQRMYGCDLGPDGRLLRGYNEFAYDGKDYIALNEDL

RSWTAADKAAQITQRKWEAAREAEQRRAYLEGTCVEWLRRYLENGKKTL

QRTDSPKAHVTHHSRPEDKVTLRCWALGFYPADITLTWQLNGEELIQDM

ELVETRPAGDGTFQKWASVVVPLGKEQYYTCHVYHQGLPEPLTLRWEPG

SHHHHHZ

Soluble C*07:019115E-K$^b$. Nucleotide Sequence (SEQ ID NO. 25) and Amino Acid Sequence (SEQ ID NO. 26)
Sequences are listed in the following order:
Signal peptide derived from Fibroin-L (in regular Arial font below)
HLA-C*07:01 α1 domain (underlined below)
HLA-C*07:01 α2 domain with Q115E mutation (in bold below)
Mouse K$^b$ α3 domain (in italics below)
Flexible GS linker (in bold and underlined below)
6×His tag (in bold and italics below)

SEQ ID NO. 25
ATGATGCGGCCCATCGTGCTGGTGCTGCTGTTTGCCACAAGCGCCCTGG

CCTGCAGCCACAGCATGCGGTACTTTGACACCGCCGTGTCCAGACCCGG

AAGAGGCGAGCCCAGATTCATCAGCGTGGGCTACGTGGACGACACCCAG

TTCGTCAGATTCGACAGCGACGCCGCCAGCCCCAGAGGCGAACCTAGAG

CACCTTGGGTGGAACAGGAAGGCCCCGAGTACTGGGACAGAGAGACACA

```
                                           -continued
GAACTACAAGCGGCAGGCCCAGGCCGACAGAGTGTCCCTGAGAAACCTG

CGGGGCTACTACAACCAGAGCGAGGACGGCAGCCACACCCTGCAGAGAA

TGTACGGCTGTGACCTGGGCCCCGATGGCAGACTGCTGAGAGGCTACGA

TGAGAGCGCCTACGACGGCAAGGACTATATCGCCCTGAACGAGGACCTG

CGGAGCTGGACAGCCGCCGATACAGCCGCCCAGATCACCCAGAGAAAAC

TGGAAGCCGCCAGAGCCGCCGAGCAGCTGAGAGCTTATCTGGAAGGCAC

CTGTGTGGAATGGCTGCGGAGATACCTGGAAAACGGCAAAGAGAGACTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGC

AGCCACCACCACCATCACCATTGA
```

SEQ ID NO. 26
MMRPIVLVLLFATSALAC<u>SHSMRYFDTAVSRPGREPRFISVGYVDDTQ</u>

<u>FVRFDSDAASPRGEPRAPWVEQEGPEYWDRETQNYKRQAQADRVSLRNL</u>

<u>RGYYNQSED</u>GSHTLQRMYGCDLGPDGRLLRGYDESAYDGKDYIALNEDL

RSWTAADTAAQITQRKLEAARAAEQLRAYLEGTCVEWLRRYLENGKETL

Q*RTDSPKAHVTHHSRPEDKVTLRCWALGFYPADITLTWQLNGEELIQDM*

*ELVETRPAGDGTFQKWASVVVPLGKEQYYTCHVYHQGLPEPLTLRWEP*G

S_HHHHHH_Z

Soluble C*07:02<sub>9115E</sub>-K<sup>b</sup>. Nucleotide Sequence (SEQ ID NO. 27) and Amino Acid Sequence (SEQ ID NO. 28)
  Sequences are listed in the following order:
    Signal peptide derived from Fibroin-L (in regular Arial font below)
    HLA-C*07:02 α1 domain (underlined below)
    HLA-C*07:02 α2 domain with Q115E mutation (in bold below)
    Mouse K<sup>b</sup> α3 domain (in italics below)
    Flexible GS linker (in bold and underlined below)
    6×His tag (in bold and italics below)

```
                                                SEQ ID NO. 27
ATGATGCGGCCCATCGTGCTGGTGCTGCTGTTTGCCACATCTGCCCTGG

CCTGCAGCCACAGCATGCGGTACTTTGACACCGCCGTGTCCAGACCCGG

AAGAGGCGAGCCCAGATTCATCAGCGTGGGCTACGTGGACGACACCCAG

TTCGTCAGATTCGACAGCGACGCCGCCAGCCCCAGAGGCGAACCTAGAG

CACCTTGGGTGGAACAGGAAGGCCCCGAGTACTGGGACAGAGAGACACA

GAAGTACAAGCGGCAGGCCCAGGCCGACAGAGTGTCCCTGAGAAACCTG

CGGGGCTACTACAACCAGAGCGAGGACGGCAGCCACACCCTGCAGAGAA

TGAGCGGCTGTGACCTGGGCCCCGATGGCAGACTGCTGAGAGGCTACGA

TGAGAGCGCCTACGACGGCAAGGACTATATCGCCCTGAACGAGGACCTG

CGGAGCTGGACAGCCGCCGATACAGCCGCCCAGATCACCCAGAGAAAAC

TGGAAGCCGCCAGAGCCGCCGAGCAGCTGAGAGCTTATCTGGAAGGCAC
```

```
                                           -continued
CTGTGTGGAATGGCTGCGGAGATACCTGGAAAACGGCAAAGAGAGACTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG

CATCTGTGGTGGTGCCTCTTGGGAAGGAGCAGTATTACACATGCCATGT

GTACCATCAGGGGCTGCCTGAGCCCCTCACCCTGAGATGGGAGCCGGC

AGCCACCACCACCATCACCATTGA
```

SEQ ID NO. 28
MMRPIVLVLLFATSALAC<u>SHSMRYFDTAVSRPGREPRFISVGYVDDTQ</u>

<u>FVRFDSDAASPRGEPRAPWVEQEGPEYWDRETQKYKRQAQADRVSLRNL</u>

<u>RGYYNQSED</u>GSHTLQRMSGCDLGPDGRLLRGYDESAYDGKDYIALNEDL

RSWTAADTAAQITQRKLEAARAAEQLRAYLEGTCVEWLRRYLENGKETL

Q*RTDSPKAHVTHHSRPEDKVTLRCWALGFYPADITLTWQLNGEELIQDM*

*ELVETRPAGDGTFQKWASVVVPLGKEQYYTCHVYHQGLPEPLTLRWEF*G

S_HHHHHH_Z

Soluble C*16:01<sub>9115E</sub>-K<sup>b</sup>, Nucleotide Sequence (SEQ ID NO. 29) and Amino Acid Sequence (SEQ ID NO. 30)
  Sequences are listed in the following order:
    Signal peptide derived from Fibroin-L (in regular Arial font below)
    HLA-C*16:01 α1 domain (underlined below)
    HLA-C*16:01 α2 domain with Q115E mutation (in bold below)
    Mouse K<sup>b</sup> α3 domain (in italics below)
    Flexible GS linker (in bold and underlined below)
    6×His tag (in bold and italics below)

```
                                                SEQ ID NO. 29
ATGATGAGGCCCATCGTGCTGGTGCTGCTGTTCGCCACATCTGCCCTGG

CCTGCAGCCACAGCATGCGGTACTTTTACACCGCCGTGTCCAGACCCGG

CAGAGGCGAGCCTAGATTCATTGCCGTGGGCTACGTGGACGACACCCAG

TTCGTCAGATTCGACAGCGACGCCGCCAGCCCCAGAGGGGAACCTAGAG

CACCTTGGGTGGAACAGGAAGGCCCCGAGTACTGGGACAGAGAGACACA

GAAGTACAAGCGGCAGGCCCAGACCGACCGGGTGTCCCTGAGAAACCTG

CGGGGCTACTACAACCAGAGCGAGGCCGGCTCTCACACCCTGCAGTGGA

TGTACGGCTGCGACCTGGGCCCTGATGGCAGACTGCTGAGAGGCTACGA

CGAGTCCGCCTACGACGGCAAGGACTATATCGCCCTGAACGAGGACCTG

CGGAGCTGGACAGCCGCCGATACAGCCGCCCAGATCACCCAGAGAAAGT

GGGAAGCCGCCAGAGCCGCCGAGCAGCAGAGAGCTTATCTGGAAGGCAC

CTGTGTGGAATGGCTGCGGAGATACCTGGAAAACGGCAAAGAGACACTG

CAGCGCACAGATTCCCCAAAGGCCCATGTGACCCATCACAGCAGACCTG

AAGATAAAGTCACCCTGAGGTGCTGGGCCCTGGGCTTCTACCCTGCTGA

CATCACCCTGACCTGGCAGTTGAATGGGGAGGAGCTGATCCAGGACATG

GAGCTTGTGGAGACCAGGCCTGCAGGGGATGGAACCTTCCAGAAGTGGG
```

-continued

```
CATCTGTGGTGGTGCCTCTTGGGAAGGAGCAGTATTACACATGCCATGT
GTACCATCAGGGGCTGCCTGAGCCCCTCACCCTGAGATGGGAGCCGGC
AGCCACCACCACCATCACCATTGA
```

SEQ ID NO. 30
```
MMRPIVLVLLFATSALACSHSMRYFYTAVSRPGRGEPRFIAVGYVDDTQ
FVRFDSDAASPRGEPRAPWVEQEGPEYWDRETQKYKRQAQTDRVSLRNL
RGYYNQSEAGSHTLQWMYGCDLGPDGRLLRGYDESAYDGKDYIALNEDL
RSWTAADTAAQITQRKWEAARAAEQQRAYLEGTCVEWLRRYLENGKETL
QRTDSPKAHVTHHSRPEDKVTLRCWALGFYPADITLTWQLNGEELIQDM
ELVETRPAGDGTFQKWASVVVPLGKEQYYTCHVYHQGLPEPLTLRWEPG
SHHHHHHZ
```

As with the sequences noted above, the present application may similarly be directed to the following sequences:
Soluble B*35:01-Wt, Nucleotide Sequence (SEQ ID NO. 31) and Amino Acid Sequence (SEQ ID NO. 32)
Sequences are listed in the following order:
Signal peptide derived from Fibroin-L (in regular Arial font below)
HLA-B*35:01 α1 domain (underlined below)
HLA-B*35:01 α2 domain (in bold below)
HLA-B*35:01 α3 domain (in italics below)
Flexible GS linker (in bold and underlined below)
6×His tag (in bold and italics below)

SEQ ID NO. 31
```
ATGATGCGGCCCATCGTGCTGGTGCTGCTGTTTGCCACATCTGCCCTGG
CCGGCTCCCACTCCATGAGGTATTTCTACACCGCCATGTCCCGGCCCGG
CCGCGGGGAGCCCCGCTTCATCGCAGTGGGCTACGTGGACGACACCCAG
TTCGTGAGGTTCGACAGCGACGCCGCGAGTCCGAGGACGGAGCCCCGGG
CGCCATGGATAGAGCAGGAGGGGCCGGAGTATTGGGACCGGAACACACA
GATCTTCAAGACCAACACACAGACTTACCGAGAGAGCCTGCGGAACCTG
CGCGGCTACTACAACCAGAGCGAGGCCGGGTCTCACATCATCCAGAGGA
TGTATGGCTGCGACCTGGGGCCCGACGGGCGCCTCCTCCGCGGGCATGA
CCAGTCCGCCTACGACGGCAAGGATTACATCGCCCTGAACGAGGACCTG
AGCTCCTGGACCGCGGCGGACACCGCGGCTCAGATCACCCAGCGCAAGT
GGGAGGCGGCCCGTGTGGCGGAGCAGCTGAGAGCCTACCTGGAGGGCCT
GTGCGTGGAGTGGCTCCGCAGATACCTGGAGAACGGGAAGGAGACGCTG
CAGCGCGCGGACCCCCCAAAGACACACGTGACCCACCACCCCGTCTCTG
ACCATGAGGCCACCCTGAGGTGCTGGGCCCTGGGCTTCTACCCTGCGGA
GATCACACTGACCTGGCAGCGGGATGGCGAGGACCAAACTCAGGACACT
GAGCTTGTGGAGACCAGACCAGCAGGAGATAGAACCTTCCAGAAGTGGG
CAGCTGTGGTGGTGCCTTCTGGAGAAGAGCAGAGATACACATGCCATGT
ACAGCATGAGGGGCTGCCCAAGCCCCTCACCCTGAGATGGGAGCCGGC
AGCCACCACCACCATCACCATTGA
```

SEQ ID NO. 32
```
MMRPIVLVLLFATSALAGSHSMRYFYTAMSRPGRGEPRFIAVGYVDDTQ
FVRFDSDAASPRTEPRAPWIEQEGPEYWDRNTQIFKTNTQTYRESLRNL
RGYYNQSEAGSHIIQRMYGCDLGPDGRLLRGHDQSAYDGKDYIALNEDL
SSWTAADTAAQITQRKWEAARVAEQLRAYLEGLCVEWLRRYLENGKETL
QRADPPKTHVTHHPVSDHEATLRCWALGFYPAEITLTWQRDGEDQTQDT
ELVETRPAGDRTFQKWAAVVVPSGEEQRYTCHVQHEGLPKPLTLRWEPG
SHHHHHHZ
```

Soluble B*35:01-K$^b$. Nucleotide Sequence (SEQ ID NO. 33) and Amino Acid Sequence (SEQ ID NO. 34)
Sequences are listed in the following order:
Signal peptide derived from Fibroin-L (in regular Arial font below)
HLA-B*35:01 α1 domain (underlined below)
HLA-B*35:01 α2 domain (in bold below)
Mouse K$^b$ α3 domain (in italics below)
Flexible GS linker (in bold and underlined below)
6×His tag (in bold and italics below)

SEQ ID NO. 33
```
ATGATGCGGCCCATCGTGCTGGTGCTGCTGTTTGCCACATCTGCCCTGG
CCGGCTCCCACTCCATGAGGTATTTCTACACCGCCATGTCCCGGCCCGG
CCGCGGGGAGCCCCGCTTCATCGCAGTGGGCTACGTGGACGACACCCAG
TTCGTGAGGTTCGACAGCGACGCCGCGAGTCCGAGGACGGAGCCCCGGG
CGCCATGGATAGAGCAGGAGGGGCCGGAGTATTGGGACCGGAACACACA
GATCTTCAAGACCAACACACAGACTTACCGAGAGAGCCTGCGGAACCTG
CGCGGCTACTACAACCAGAGCGAGGCCGGGTCTCACATCATCCAGAGGA
TGTATGGCTGCGACCTGGGGCCCGACGGGCGCCTCCTCCGCGGGCATGA
CCAGTCCGCCTACGACGGCAAGGATTACATCGCCCTGAACGAGGACCTG
AGCTCCTGGACCGCGGCGGACACCGCGGCTCAGATCACCCAGCGCAAGT
GGGAGGCGGCCCGTGTGGCGGAGCAGCTGAGAGCCTACCTGGAGGGCCT
GTGCGTGGAGTGGCTCCGCAGATACCTGGAGAACGGGAAGGAGACGCTG
CAGCGCACAGATTCCCCAAAGGCCCATGTGACCCATCACAGCAGACCTG
AAGATAAAGTCACCCTGAGGTGCTGGGCCCTGGGCTTCTACCCTGCTGA
CATCACCCTGACCTGGCAGTTGAATGGGGAGGAGCTGATCCAGGACATG
GAGCTTGTGGAGACCAGGCCTGCAGGGGATGGAACCTTCCAGAAGTGGG
CATCTGTGGTGGTGCCTCTTGGGAAGGAGCAGTATTACACATGCCATGT
GTACCATCAGGGGCTGCCTGAGCCCCTCACCCTGAGATGGGAGCCGGC
AGCCACCACCACCATCACCATTGA
```

SEQ ID NO. 34
```
MMRPIVLVLLFATSALAGSHSMRYFYTAMSRPGRGEPRFIAVGYVDDTQ
FVRFDSDAASPRTEPRAPWIEQEGPEYWDRNTQIFKTNTQTYRESLRNL
RGYYNQSEAGSHIIQRMYGCDLGPDGRLLRGHDQSAYDGKDYIALNEDL
SSWTAADTAAQITQRKWEAARVAEQLRAYLEGLCVEWLRRYLENGKETL
QRTDSPKAHVTHHSRPEDKVTLRCWALGFYPADITLTWQLNGEELIQDM
ELVETRPAGDTFQKWASVVVPLGKEQYYTCHVYHQGLPEPLTLRWEPG
SHHHHHHZ
```

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

1. Wooldridge L, Lissina A, Cole D K, van den Berg H A, Price D A, Sewell A K. Tricks with tetramers: how to get the most from multimeric peptide-MHC. *Immunology.* 2009; 126(2):147-164.
2. Dolton G, Tungatt K, Lloyd A, Bianchi V, Theaker S M, Trimby A, Holland C J, Donia M, Godkin A J, Cole D K, Straten P T, Peakman M, Svane I M, Sewell A K. More tricks with tetramers: a practical guide to staining T cells with peptide-MHC multimers. *Immunology.* 2015; 146(1):11-22.
3. Rossjohn J, Gras S, Miles J J, Turner S J, Godfrey D I, Mccluskey J. T cell antigen receptor recognition of antigen-presenting molecules. *Annu Rev Immunol.* 2015; 33:169-200.
4. Marrack P, Scott-Browne J P, Dai S, Gapin L, Kappler J W. Evolutionarily conserved amino acids that control TCR-MHC interaction. *Annu Rev Immunol.* 2008; 26:171-203.
5. Altman J D, Moss P A, Goulder P J, Barouch D H, McHeyzer-Williams M G, Bell J I, McMichael A J, Davis M M. Phenotypic analysis of antigen-specific T lymphocytes. *Science.* 1996; 274(5284):94-96.
6. Klenerman P, Cerundolo V, Dunbar P R. Tracking T cells with tetramers: new tales from new tools. *Nat Rev Immunol.* 2002; 2(4):263-272.
7. Janeway C. Immunobiology: the immune system in health and disease (ed 6th). New York: Garland Science; 2005.
8. Migueles S A, Sabbaghian M S, Shupert W L, Bettinotti M P, Marincola F M, Martino L, Hallahan C W, Selig S M, Schwartz D, Sullivan J, Connors M. HLA B*5701 is highly associated with restriction of virus replication in a subgroup of HIV-infected long term nonprogressors. *Proc Natl Acad Sci USA.* 2000; 97(6):2709-2714.
9. Kawase T, Akatsuka Y, Torikai H, Morishima S, Oka A, Tsujimura A, Miyazaki M, Tsujimura K, Miyamura K, Ogawa S, Inoko H, Morishima Y, Kodera Y, Kuzushima K, Takahashi T. Alternative splicing due to an intronic SNP in HMSD generates a novel minor histocompatibility antigen. *Blood.* 2007; 110(3):1055-1063.
10. Rodenko B, Toebes M, Hadrup S R, van Esch W J, Molenaar A M, Schumacher T N, Ovaa H. Generation of peptide-MHC class I complexes through U V-mediated ligand exchange. *Nat Protoc.* 2006; 1(3):1120-1132.
11. Bakker A H, Hoppes R, Linnemann C, Toebes M, Rodenko B, Berkers C R, Hadrup S R, van Esch W J, Heemskerk M H, Ovaa H, Schumacher T N. Conditional MHC class I ligands and peptide exchange technology for the human MHC gene products HLA-A1,-A3,-A11, and -B7. *Proc Natl Acad Sci USA.* 2008; 105(10):3825-3830.
12. Saini S K, Schuster H, Ramnarayan V R, Rammensee H G, Stevanovic S, Springer S. Dipeptides catalyze rapid peptide exchange on MHC class I molecules. *Proc Natl Acad Sci USA.* 2015; 112(1):202-207.
13. Laugel B, van den Berg H A, Gostick E, Cole D K, Wooldridge L, Boulter J, Milicic A, Price D A, Sewell A K. Different T cell receptor affinity thresholds and CD8 coreceptor dependence govern cytotoxic T lymphocyte activation and tetramer binding properties. *J Biol Chem.* 2007; 282(33):23799-23810.
14. Nguyen L T, Yen P H, Nie J, Liadis N, Ghazarian D, Al-Habeeb A, Easson A, Leong W, Lipa J, McCready D, Reedijk M, Hogg D, Joshua A M, Quirt I, Messner H, Shaw P, Crump M, Sharon E, Ohashi P S. Expansion and characterization of human melanoma tumor-infiltrating lymphocytes (TILs). *PLOS One.* 2010; 5(11):e13940.
15. Kagoya Y, Nakatsugawa M, Yamashita Y, Ochi T, Guo T, Anczurowski M, Saso K, Butler M O, Arrowsmith C H, Hirano N. BET bromodomain inhibition enhances T cell persistence and function in adoptive immunotherapy models. *J Clin Invest.* 2016; 126(9):3479-3494.
16. Hirano N, Butler M O, Xia Z, Ansen S, von Bergwelt-Baildon M S, Neuberg D, Freeman G J, Nadler L M. Engagement of CD83 ligand induces prolonged expansion of CD8+ T cells and preferential enrichment for antigen specificity. *Blood.* 2006; 107(4):1528-1536.
17. Butler M O, Lee J S, Ansen S, Neuberg D, Hodi F S, Murray A P, Drury L, Berezovskaya A, Mulligan R C, Nadler L M, Hirano N. Long-lived antitumor CD8+ lymphocytes for adoptive therapy generated using an artificial antigen-presenting cell. *Clin Cancer Res.* 2007; 13(6):1857-1867.
18. Hirano N, Butler M O, Xia Z, Berezovskaya A, Murray A P, Ansen S, Kojima S, Nadler L M. Identification of an immunogenic CD8+ T-cell epitope derived from gamma-globin, a putative tumor-associated antigen for juvenile myelomonocytic leukemia. *Blood.* 2006; 108(8):2662-2668.
19. Imataki O, Ansen S, Tanaka M, Butler M O, Berezovskaya A, Milstein M I, Kuzushima K, Nadler L M, Hirano N. IL-21 can supplement suboptimal Lck-independent MAPK activation in a STAT-3-dependent manner in human CD8(+) T cells. *J Immunol.* 2012; 188(4):1609-1619.
20. Butler M O, Ansen S, Tanaka M, Imataki O, Berezovskaya A, Mooney M M, Metzler G, Milstein M I, Nadler L M, Hirano N. A panel of human cell-based artificial APC enables the expansion of long-lived antigen-specific CD4+ T cells restricted by prevalent HLA-D R alleles. *Int Immunol.* 2010; 22(11):863-873.
21. Wooldridge L, Clement M, Lissina A, Edwards E S, Ladell K, Ekeruche J, Hewitt R E, Laugel B, Gostick E, Cole D K, Debets R, Berrevoets C, Miles J J, Burrows S R, Price D A, Sewell A K. MHC class I molecules with Superenhanced CD8 binding properties bypass the requirement for cognate TCR recognition and nonspecifically activate CTLs. *J Immunol.* 2010; 184(7):3357-3366.
22. Wooldridge L, Lissina A, Vernazza J, Gostick E, Laugel B, Hutchinson S L, Mirza F, Dunbar P R, Boulter J M, Glick M, Cerundolo V, van den Berg H A, Price D A, Sewell A K. Enhanced immunogenicity of CTL antigens through mutation of the CD8 binding MHC class I invariant region. *Eur J Immunol.* 2007; 37(5):1323-1333.
23. Hirano N, Butler M O, Von Bergwelt-Baildon M S, Maecker B, Schultze J L, O'Connor K C, Schur P H, Kojima S, Guinan E C, Nadler L M. Autoantibodies frequently detected in patients with aplastic anemia. *Blood.* 2003; 102(13):4567-4575.
24. Hirano N, Butler M O, Xia Z, Berezovskaya A, Murray A P, Ansen S, Nadler L M. Efficient presentation of naturally processed HLA class I peptides by artificial antigen-presenting cells for the generation of effective antitumor responses. *Clin Cancer Res.* 2006; 12(10): 2967-2975.
25. Tanaka M, Butler M O, Ansen S, Imataki O, Berezovskaya A, Nadler L M, Hirano N. Induction of HLA-DP4-

26. Ochi T, Nakatsugawa M, Chamoto K, Tanaka S, Yamashita Y, Guo T, Fujiwara H, Yasukawa M, Butler M O, Hirano N. Optimization of T-cell Reactivity by Exploiting TCR Chain Centricity for the Purpose of Safe and Effective Antitumor TCR Gene Therapy. *Cancer Immunol Res.* 2015; 3(9):1070-1081.

27. Nakatsugawa M, Yamashita Y, Ochi T, Tanaka S, Chamoto K, Guo T, Butler M O, Hirano N. Specific roles of each TCR hemichain in generating functional chain-centric TCR. *J Immunol.* 2015; 194(7):3487-3500.

28. Feldman S A, Assadipour Y, Kriley I, Goff S L, Rosenberg S A. Adoptive Cell Therapy—Tumor-Infiltrating Lymphocytes, T-Cell Receptors, and Chimeric Antigen Receptors. *Semin Oncol.* 2015; 42(4):626-639.

29. Robbins P F, Lu Y C, El-Gamil M, Li Y F, Gross C, Gartner J, Lin J C, Teer J K, Cliften P, Tycksen E, Samuels Y, Rosenberg S A. Mining exomic sequencing data to identify mutated antigens recognized by adoptively transferred tumor-reactive T cells. *Nat Med.* 2013; 19(6):747-752.

30. Parker K C, Bednarek M A, Coligan J E. Scheme for ranking potential HLA-A2 binding peptides based on independent binding of individual peptide side-chains. *J Immunol.* 1994; 152(1):163-175.

---

SEQUENCE LISTING

```
Sequence total quantity: 122
SEQ ID NO: 1           moltype = DNA  length = 906
FEATURE                Location/Qualifiers
source                 1..906
                       mol_type = genomic DNA
                       organism = Homo sapiens
SEQUENCE: 1
atgatgcggc ccatcgtgct ggtgctgctg tttgccacat ctgccctggc cggaagccac   60
agcatgcggt acttttttcac cagcgtgtcc agacccggca gaggcgagcc cagattcatt  120
gccgtgggct acgtggacga cacccagttc gtcagattcg acagcgacgc cgccagccag  180
cggatggaac ctagagcccc ttggatcgag caggaaggcc ccgagtactg ggacggcgag  240
acacggaaag tgaaggccca cagccagacc cacagagtgg atctgggcac cctgcggggc  300
tactacaatc agtctgaggc cggctcccac accgtgacag ggatgtacgg ctgtgacgtg  360
ggcagcgact ggcggttcct gagaggctac caccagtacg cctacgacgg caaggactat  420
atcgccctga aagaggacct gcggagctgg acagccgccg atatggccgc ccagaccacc  480
aagcacaaat gggaagccgc ccacgtggcc gagcagctga gagcttatct ggaaggcacc  540
tgtgtggaat ggctgcggag atacctggaa aacggcaaag agacactgca gcgcacggac  600
gcccccaaaa cgcatatgac tcaccacgct gtctctgacc atgaagccac cctgaggtgc  660
tgggccctga gcttctaccc tgcggagatc acactgacct ggcagcggga tggggaggac  720
cagacccagg acacggagtc cgtggagacc aggcctcag gggatggaac cttccagaag  780
tgggcggctg tggtggtgcc ttctggacag gagcagagat acacctgcca tgtgcagcat  840
gagggtttgc ccaagccccct caccctgaga tgggagccgg gcagccacca ccaccatcac  900
cattga                                                              906

SEQ ID NO: 2           moltype = AA  length = 302
FEATURE                Location/Qualifiers
source                 1..302
                       mol_type = protein
                       organism = Homo sapiens
SEQUENCE: 2
MMRPIVLVLL FATSALAGSH SMRYFFTSVS RPGRGEPRFI AVGYVDDTQF VRFDSDAASQ   60
RMEPRAPWIE QEGPEYWDGE TRKVKAHSQT HRVDLGTLRG YYNQSEAGSH TVQRMYGCDV  120
GSDWRFLRGY HQYAYDGKDY IALKEDLRSW TAADMAAQTT KHKWEAAHVA EQLRAYLEGT  180
CVEWLRRYLE NGKETLQRTD APKTHMTHHA VSDHEATLRC WALSFYPAEI TLTWQRDGED  240
QTQDTELVET RPAGDGTFQK WAAVVVPSGQ EQRYTCHVQH EGLPKPLTLR WEPGSHHHHH  300
HZ                                                                 302

SEQ ID NO: 3           moltype = DNA  length = 906
FEATURE                Location/Qualifiers
source                 1..906
                       mol_type = genomic DNA
                       organism = Homo sapiens
SEQUENCE: 3
atgatgcggc ccatcgtgct ggtgctgctg tttgccacat ctgccctggc cggaagccac   60
agcatgcggt acttttttcac cagcgtgtcc agacccggca gaggcgagcc cagattcatt  120
gccgtgggct acgtggacga cacccagttc gtcagattcg acagcgacgc cgccagccag  180
cggatggaac ctagagcccc ttggatcgag caggaaggcc ccgagtactg ggacggcgag  240
acacggaaag tgaaggccca cagccagacc cacagagtgg atctgggcac cctgcggggc  300
tactacaatc agtctgaggc cggctcccac accgtgcaga ggatgtacgg ctgtgacgtg  360
ggcagcgact ggcggttcct gagaggctac caccagtacg cctacgacgg caaggactat  420
atcgccctga aagaggacct gcggagctgg acagccgccg atatggccgc ccagaccacc  480
aagcacaaat gggaagccgc ccacgtggcc gagcagctga gagcttatct ggaaggcacc  540
tgtgtggaat ggctgcggag atacctggaa aacggcaaag agacactgca gcgcacagat  600
tccccaaagg cccatgtgac ccatcacagc agacctgaag ataaagtcac cctgaggtgc  660
tgggccctgg gcttctaccc tgctgacatc acctgacct ggcagttgaa tggggaggag  720
ctgatccagg acatggagct tgtggagacc aggcctcag gggatggaac cttccagaag  780
tgggcatctg tggtggtgcc tcttgggaag gagcagtatt acacatgcca tgtgtaccat  840
caggggctgc ctgagcccct caccctgaga tgggagccgg gcagccacca ccaccatcac  900
cattga                                                              906
```

```
SEQ ID NO: 4              moltype = AA   length = 302
FEATURE                   Location/Qualifiers
source                    1..302
                          mol_type = protein
                          organism = Homo sapiens
SEQUENCE: 4
MMRPIVLVLL FATSALAGSH SMRYFFTSVS RPGRGEPRFI AVGYVDDTQF VRFDSDAASQ   60
RMEPRAPWIE QEGPEYWDGE TRKVKAHSQT HRVDLGTLRG YYNQSEAGSH TVQRMYGCDV  120
GSDWRFLRGY HQYAYDGKDY IALKEDLRSW TAADMAAQTT KHKWEAAHVA EQLRAYLEGT  180
CVEWLRRYLE NGKETLQRTD SPKAHVTHHS RPEDKVTLRC WALGFYPADI TLTWQLNGEE  240
LIQDMELVET RPAGDGTFQK WASVVVPLGK EQYYTCHVYH QGLPEPLTLR WEPGSHHHHH  300
HZ                                                                302

SEQ ID NO: 5              moltype = DNA   length = 906
FEATURE                   Location/Qualifiers
source                    1..906
                          mol_type = genomic DNA
                          organism = Homo sapiens
SEQUENCE: 5
atgatgcggc ccatcgtgct ggtgctgctg tttgccacat ctgccctggc cggaagccac   60
agcatgcggt actttttcac cagcgtgtcc agacccggca gaggcgagcc cagattcatt  120
gccgtgggct acgtggacga cacccagttc gtcagattcg acagcgacgc cgccagccag  180
cggatggaac ctagagcccc ttggatcgag caggaaggcc ccgagtactg ggacggcgag  240
acacggaaag tgaaggccca cagccagacc cacagagtgg atctgggcac cctgcggggc  300
tactacaatc agtctgaggc cggctcccac accgtgcaga ggatgtacgg ctgtgacgtg  360
ggcagcgact ggcggttcct gagaggctac acgagtacgc cctacgacgg caaggactat  420
atcgccctga agaggacctg cggagctggg acagccgccg atatggccgc ccagaccacc  480
aagcacaaat gggaagccgc ccacgtggcc gagcagctga gcttatct ggaaggcacc  540
tgtgtggaat ggctgcggag atacctgaaa acggcaaag agacactgca gcgcacagat  600
tccccaaagg cccatgtgac ccatcacagc agacctgaa ataaagtcac cctgaggtgc  660
tgggccctgg gcttctaccc tgctgacatc accctgacct ggcagttgaa tggggaggaa  720
ctgatccagg acatggagct tgtggagacc aggcctgcag gggatggaac cttccagaag  780
tgggcatctg tggtggtgcc tctgggaaag gagcagtatt acacatgcca tgtgtaccat  840
cagggggctg ctgagcccct caccctgaga tgggagccgg gcagccacca ccaccatcac  900
cattga                                                            906

SEQ ID NO: 6              moltype = AA   length = 302
FEATURE                   Location/Qualifiers
source                    1..302
                          mol_type = protein
                          organism = Homo sapiens
SEQUENCE: 6
MMRPIVLVLL FATSALAGSH SMRYFFTSVS RPGRGEPRFI AVGYVDDTQF VRFDSDAASQ   60
RMEPRAPWIE QEGPEYWDGE TRKVKAHSQT HRVDLGTLRG YYNQSEAGSH TVQRMYGCDV  120
GSDWRFLRGY HEYAYDGKDY IALKEDLRSW TAADMAAQTT KHKWEAAHVA EQLRAYLEGT  180
CVEWLRRYLE NGKETLQRTD SPKAHVTHHS RPEDKVTLRC WALGFYPADI TLTWQLNGEE  240
LIQDMELVET RPAGDGTFQK WASVVVPLGK EQYYTCHVYH QGLPEPLTLR WEPGSHHHHH  300
HZ                                                                302

SEQ ID NO: 7              moltype = DNA   length = 906
FEATURE                   Location/Qualifiers
source                    1..906
                          mol_type = genomic DNA
                          organism = Homo sapiens
SEQUENCE: 7
atgatgcggc ccatcgtgct ggtgctgctg tttgccacat ctgccctggc cggctcccac   60
tccatgaggt atttctccac atccgtgtcc cggcccggcc gcggggagcc ccgcttcatc  120
gccgtgggct acgtggacga cacgcagttc gtgcggttcg acagcgacgc cgcgagccag  180
aggatggagc cgcgggcgcc gtggatagag caggagggcg cggagtattg ggacgaggag  240
acacggaaag tgaaggccca ctcacagact gaccgagaga acctgcggat cgcgctccgc  300
tactacaacc agagcgaggc cggttctcac accctccaga tgatgtttgg ctgcgacgtg  360
gggtcggacg ggcgcttcct ccgcgggtac caccagtacg cctacgacgg caaggattac  420
atcgccctga agagaggactg cgctcttgg accgcggcgg acatggcggc tcagatcacc  480
aagcgcaagt gggaggccgc ccatgtggcg gagcagcaga gcctacct ggagggcacg  540
tgcgtggacg gctccgcag atacctggag aacgggaagg agacgctgca gcgcacggac  600
cccccaaga cacatatgac ccaccacccc atctctgacc atgaggccac tctgagatgc  660
tgggccctgg gcttctaccc tgcggagatc acactgacct ggcagcggga tgggaggac  720
cagacccagg acacggagct tgtggagacc aggcctgcag gggatggaac cttccagaag  780
tgggcagctg tggtggtacc ttctggagag gagcagagat acacctgcca tgtgcagcat  840
gagggtctgc ccaagccccc caccctgaga tgggagccgg gcagccacca ccaccatcac  900
cattga                                                            906

SEQ ID NO: 8              moltype = AA   length = 302
FEATURE                   Location/Qualifiers
source                    1..302
                          mol_type = protein
                          organism = Homo sapiens
SEQUENCE: 8
MMRPIVLVLL FATSALAGSH SMRYFSTSVS RPGRGEPRFI AVGYVDDTQF VRFDSDAASQ   60
```

```
RMEPRAPWIE QEGPEYWDEE TGKVKAHSQT DRENLRIALR YYNQSEAGSH TLQMMFGCDV   120
GSDGRFLRGY HQYAYDGKDY IALKEDLRSW TAADMAAQIT KRKWEAAHVA EQQRAYLEGT   180
CVDGLRRYLE NGKETLQRTD PPKTHMTHHP ISDHEATLRC WALGFYPAEI TLTWQRDGED   240
QTQDTELVET RPAGDGTFQK WAAVVVPSGE EQRYTCHVQH EGLPKPLTLR WEPGSHHHHH   300
HZ                                                                 302

SEQ ID NO: 9            moltype = DNA   length = 906
FEATURE                 Location/Qualifiers
source                  1..906
                        mol_type = genomic DNA
                        organism = Homo sapiens
SEQUENCE: 9
atgatgcggc ccatcgtgct ggtgctgctg tttgccacat ctgccctggc cggctcccac    60
tccatgaggt atttctccac atccgtgtcc cggcccggcc gcggggagcc ccgcttcatc   120
gccgtgggct acgtggacga cacgcagttc gtgcggttcg acagcgacgc cgcgagccag   180
aggatggagc cgcgggcgcc cgtggataga caggaggggc cggagtattg ggacgaggag   240
acagggaaag tgaaggccca ctcacagact gaccgagaga acctgcggat cgcgctccgc   300
tactacaacc agagcgaggc cggttctcac accctccaga tgatgtttgg ctgcgacgtg   360
gggtcgacg ggcgcttcct ccgcgggtac caccagtacg cctacgacgg caaggattac   420
atcgccctga agaggacct gcgctcttgg accgcggcgg acatggcggc tcagatcacc   480
aagcgcaagt gggaggcggc ccatgtggcg gagcagcaga gagcctacct ggagggcacg   540
tgcgtggacg ggctccgcag atacctggag aacgggaagg agacgctgca gcgcacagat   600
tccccaaagg cccatgtgac ccatcacagc agacctgaag ataaagtcac cctgaggtgc   660
tgggccctgg gcttctaccc tgctgacatc accctgacct ggcagttgaa tggggaggag   720
ctgatccagg acatggagct gtggagacc aggcctgcag gggatggaac cttccagaag   780
tgggcatctg tggtggtgcc tcttgggaag gagcagtatt acacatgcca tgtgtaccat   840
cagggggctgc ctgagcccct caccctgaga tgggagccgg cagccacca ccaccatcac   900
cattga                                                             906

SEQ ID NO: 10           moltype = AA   length = 302
FEATURE                 Location/Qualifiers
source                  1..302
                        mol_type = protein
                        organism = Homo sapiens
SEQUENCE: 10
MMRPIVLVLL FATSALAGSH SMRYFSTSVS RPGRGEPRFI AVGYVDDTQF VRFDSDAASQ    60
RMEPRAPWIE QEGPEYWDEE TGKVKAHSQT DRENLRIALR YYNQSEAGSH TLQMMFGCDV   120
GSDGRFLRGY HQYAYDGKDY IALKEDLRSW TAADMAAQIT KRKWEAAHVA EQQRAYLEGT   180
CVDGLRRYLE NGKETLQRTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                 302

SEQ ID NO: 11           moltype = DNA   length = 906
FEATURE                 Location/Qualifiers
source                  1..906
                        mol_type = genomic DNA
                        organism = Homo sapiens
SEQUENCE: 11
atgatgcggc ccatcgtgct ggtgctgctg tttgccacat ctgccctggc cggctcccac    60
tccatgaggt atttctccac atccgtgtcc cggcccggcc gcggggagcc ccgcttcatc   120
gccgtgggct acgtggacga cacgcagttc gtgcggttcg acagcgacgc cgcgagccag   180
aggatggagc cgcgggcgcc cgtggataga caggaggggc cggagtattg ggacgaggag   240
acagggaaag tgaaggccca ctcacagact gaccgagaga acctgcggat cgcgctccgc   300
tactacaacc agagcgaggc cggttctcac accctccaga tgatgtttgg ctgcgacgtg   360
gggtcgacg ggcgcttcct ccgcgggtac cacgagtacg cctacgacgg caaggattac   420
atcgccctga agaggacct gcgctcttgg accgcggcgg acatggcggc tcagatcacc   480
aagcgcaagt gggaggcggc ccatgtggcg gagcagcaga gagcctacct ggagggcacg   540
tgcgtggacg ggctccgcag atacctggag aacgggaagg agacgctgca gcgcacagat   600
tccccaaagg cccatgtgac ccatcacagc agacctgaag ataaagtcac cctgaggtgc   660
tgggccctgg gcttctaccc tgctgacatc accctgacct ggcagttgaa tggggaggag   720
ctgatccagg acatggagct gtggagacc aggcctgcag gggatggaac cttccagaag   780
tgggcatctg tggtggtgcc tcttgggaag gagcagtatt acacatgcca tgtgtaccat   840
cagggggctgc ctgagcccct caccctgaga tgggagccgg cagccacca ccaccatcac   900
cattga                                                             906

SEQ ID NO: 12           moltype = AA   length = 302
FEATURE                 Location/Qualifiers
source                  1..302
                        mol_type = protein
                        organism = Homo sapiens
SEQUENCE: 12
MMRPIVLVLL FATSALAGSH SMRYFSTSVS RPGRGEPRFI AVGYVDDTQF VRFDSDAASQ    60
RMEPRAPWIE QEGPEYWDEE TGKVKAHSQT DRENLRIALR YYNQSEAGSH TLQMMFGCDV   120
GSDGRFLRGY HEYAYDGKDY IALKEDLRSW TAADMAAQIT KRKWEAAHVA EQQRAYLEGT   180
CVDGLRRYLE NGKETLQRTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                 302

SEQ ID NO: 13           moltype = DNA   length = 906
```

```
FEATURE                 Location/Qualifiers
source                  1..906
                        mol_type = genomic DNA
                        organism = Homo sapiens
SEQUENCE: 13
atgatgcggc ccatcgtgct ggtgctgctg tttgccacat ctgccctggc cggctcccac    60
tccatgaggt atttctacac cgccatgtcc cggcccggcc gcggggagcc ccgcttcatc   120
gcagtgggct acgtggacga cacccagttc gtgaggttcg acagcgacgc cgcgagtccg   180
aggacggagc cccgggcgcc atggatagag caggaggggc cggagtattg ggaccggaac   240
acacagatct tcaagaccaa cacacagact taccgagagt cgctgcggaa cctgcgcggc   300
tactacaacc agagcgaggc cgggtctcac atcatccaga ggatgtatgg ctgcgacctg   360
gggcccgacg ggcgcctcct ccgcgggcat gacgagtccg cctacgacgg caaggattac   420
atcgccctga cgaggacct gagctcctgg accgcggcgg acaccgcggc tcagatcacc   480
cagcgcaagt gggaaggcgc ccgtgtggcg agcagctgga gcgagggcctg             540
tgcgtggagt ggctccgcag atacctggaa aacgggaagg agacgctgca gcgcacagat   600
tccccaaagg cccatgtgac ccatcacagc agacctgaag ataaagtcac cctgaggtgc   660
tgggccctgg cttctaccc tgctgacatc accctgacct ggcagttgaa tggggaggag   720
ctgatccagg acatggagct tgtggagacc aggcctgcag gggatggaac cttccagaag   780
tgggcatctg tggtggtgcc tcttgggaag gagcagtatt acacatgcca tgtgtaccat   840
cagggggctgc ctgagcccct caccctgaga tgggagccgg gcagccacca ccaccatcac   900
cattga                                                              906

SEQ ID NO: 14           moltype = AA  length = 302
FEATURE                 Location/Qualifiers
source                  1..302
                        mol_type = protein
                        organism = Homo sapiens
SEQUENCE: 14
MMRPIVLVLL FATSALAGSH SMRYFYTAMS RPGRGEPRFI AVGYVDDTQF VRFDSDAASP    60
RTEPRAPWIE QEGPEYWDRN TQIFKTNTQT YRESLRNLRG YYNQSEAGSH IIQRMYGCDL   120
GPDGRLLRGH DESAYDGKDY IALNEDLSSW TAADTAAQIT QRKWEAARVA EQLRAYLEGL   180
CVEWLRRYLE NGKETLQRTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                 302

SEQ ID NO: 15           moltype = DNA  length = 906
FEATURE                 Location/Qualifiers
source                  1..906
                        mol_type = genomic DNA
                        organism = Homo sapiens
SEQUENCE: 15
atgatgcggc ccatcgtgct ggtgctgctg tttgccacat ctgccctggc cggcagccac    60
agcatgcggt acttccacac cagcgtgtcc agacccggaa gaggcgagcc cagattcatc   120
accgtgggct acgtggacga cacccctgttc gtcagattcg acagcgacgc caccagcccc   180
cggaaagaac ctagagcccc ttggatcgag caggaaggcc ccgagtactg ggacagagag   240
acacagatca gcaagaccaa cacccagacc tacagagaga gcctgcggaa cctgcggggc   300
tactacaatc agagcgaggc cggctctcac accctgcagt ctatgtacgg ctgcgacgtg   360
ggccccgatg gcagactgct gagaggccac aacgagtacg cctacgacgg caaggactat   420
atcgccctga cgaggaccct gcggagctgg acagccgccg atacagccgc ccagatcacc   480
cagagaaagt gggaggccgc cagagtggcc gaacagctga gagcctatct ggaaggcgag   540
tgcgtggaat ggctgcggag atacctggaa aacggcaaag agacactgca gcgcacagat   600
tccccaaagg cccatgtgac ccatcacagc agacctgaag ataaagtcac cctgaggtgc   660
tgggccctgg cttctaccc tgctgacatc accctgacct ggcagttgaa tggggaggag   720
ctgatccagg acatggagct gtggagacc aggcctgcag gggatggaac cttccagaag   780
tgggcatctg tggtggtgcc tcttgggaag gagcagtatt acacatgcca tgtgtaccat   840
cagggggctgc ctgagcccct caccctgaga tgggagccgg gcagccacca ccaccatcac   900
cattga                                                              906

SEQ ID NO: 16           moltype = AA  length = 302
FEATURE                 Location/Qualifiers
source                  1..302
                        mol_type = protein
                        organism = Homo sapiens
SEQUENCE: 16
MMRPIVLVLL FATSALAGSH SMRYFHTSVS RPGRGEPRFI TVGYVDDTLF VRFDSDATSP    60
RKEPRAPWIE QEGPEYWDRE TQISKTNTQT YRESLRNLRG YYNQSEAGSH TLQSMYGCDV   120
GPDGRLLRGH NEYAYDGKDY IALNEDLRSW TAADTAAQIT QRKWEAARVA EQLRAYLEGE   180
CVEWLRRYLE NGKETLQRTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                 302

SEQ ID NO: 17           moltype = DNA  length = 906
FEATURE                 Location/Qualifiers
source                  1..906
                        mol_type = genomic DNA
                        organism = Homo sapiens
SEQUENCE: 17
atgatgaggc ccatcgtgct ggtgctgctg ttcgccacat ctgccctggc cggcagccac    60
agcatgcggt actttttacac cgccatgagc agacccggca gaggcgagcc cagattcatc   120
```

```
accgtgggct acgtggacga caccctgttc gtcagattcg acagcgacgc caccagcccc   180
cggaaagaac ctagagcccc ttggatcgag caggaaggcc ccgagtactg ggacagagag   240
acacagatca gcaagaccaa cacccagacc tacagagaga acctgcggac cgccctgcgg   300
tactacaatc agtctgaggc cggctcccac atcatccagc ggatgtacgg ctgtgacgtg   360
ggccccgatg gcagactgct gagaggctac gacgagtacg cctacgacgg caaggactat   420
atcgccctga cgaggacct gagcagctgg acagccgccg atacagccgc ccagatcacc   480
cagagaaagt gggaggccgc cagagtggcc gagcaggata gagcctatct ggaaggcctg   540
tgcgtggaaa gcctgcggag atacctggaa aacggcaaag agacactgca gcgcacagat   600
tccccaaagg cccatgtgac ccatcacagc agacctgagg ataaagtcac cctgaggtgc   660
tgggccctgg gcttctaccc tgctgacatc accctgacct ggcagttgaa tggggaggag   720
ctgatccagg acatggagct tgtggagacc aggcctgcag gggatggaac cttccagaag   780
tgggcatctg tggtggtgcc tcttgggaag gagcagtatt acacatgcca tgtgtaccat   840
cagggggctgc ctgagcccct caccctgaga tgggagccgg gcagccacca ccaccatcac   900
cattga                                                               906

SEQ ID NO: 18           moltype = AA  length = 302
FEATURE                 Location/Qualifiers
source                  1..302
                        mol_type = protein
                        organism = Homo sapiens
SEQUENCE: 18
MMRPIVLVLL FATSALAGSH SMRYFYTAMS RPGRGEPRFI TVGYVDDTLF VRFDSDATSP    60
RKEPRAPWIE QEGPEYWDRE TQISKTNTQT YRENLRTALR YYNQSEAGSH IIQRMYGCDV   120
GPDGRLLRGY DEYAYDKDY IALNEDLSSW TAADTAAQIT QRKWEAARVA EQDRAYLEGL    180
CVESLRRYLE NGKETLQRTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                   302

SEQ ID NO: 19           moltype = DNA  length = 906
FEATURE                 Location/Qualifiers
source                  1..906
                        mol_type = genomic DNA
                        organism = Homo sapiens
SEQUENCE: 19
atgatgcggc ccatcgtgct ggtgctgctg tttgccacat ctgccctggc cggcagccac    60
agcatgcggt acttttacac cagcgtgtcc agacccggca gaggcgagcc cagattcatc   120
agcgtgggct acgtggacga cacccagttc gtcagattcg acagcgacgc cgccagcccc   180
agagaggaac ctagagcccc ttggatcgag caggaaggcc ccgagtactg ggaccggaac   240
acccagatct acaaggccca ggcccagacc gacagagaga ggagccagcc cctgcggggc   300
tactacaacc agagcgaggc cggctctcac accctgcagt ctatgtacgg ctgcgacgtg   360
ggccccgatg gcagactgct gagaggccac gatgagtacg cctacgacgg caaggactat   420
atcgccctga cgaggacct gcggagctgg acagccgccg atacagccgc ccagatcacc   480
cagagaaagt gggaggccgc cagagaggcc gaacagagaa gggcctatct ggaaggcgag   540
tgcgtggaat ggctgcggag atacctggaa aatggcaagg acaagctgga acgcacagat   600
tccccaaagg cccatgtgac ccatcacagc agacctgaag ataaagtcac cctgaggtgc   660
tgggccctgg gcttctaccc tgctgacatc accctgacct ggcagttgaa tggggaggag   720
ctgatccagg acatggagct tgtggagacc aggcctgcag gggatggaac cttccagaag   780
tgggcatctg tggtggtgcc tcttgggaag gagcagtatt acacatgcca tgtgtaccat   840
cagggggctgc ctgagcccct caccctgaga tgggagccgg gcagccacca ccaccatcac   900
cattga                                                               906

SEQ ID NO: 20           moltype = AA  length = 302
FEATURE                 Location/Qualifiers
source                  1..302
                        mol_type = protein
                        organism = Homo sapiens
SEQUENCE: 20
MMRPIVLVLL FATSALAGSH SMRYFYTSVS RPGRGEPRFI SVGYVDDTQF VRFDSDAASP    60
REEPRAPWIE QEGPEYWDRN TQIYKAQAQT DRESLRNLRG YYNQSEAGSH TLQSMYGCDV   120
GPDGRLLRGH DEYAYDGKDY IALNEDLRSW TAADTAAQIT QRKWEAAREA EQRRAYLEGE   180
CVEWLRRYLE NGKDKLERTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                   302

SEQ ID NO: 21           moltype = DNA  length = 906
FEATURE                 Location/Qualifiers
source                  1..906
                        mol_type = genomic DNA
                        organism = Homo sapiens
SEQUENCE: 21
atgatgcggc ccatcgtgct ggtgctgctg tttgccacat ctgccctggc cggcagccac    60
agcatgcggt actttgacac cgccatgagc agacccggca gaggcgagcc cagattcatc   120
agcgtgggct acgtggacga cacccagttc gtcagattcg acagcgacgc cgccagcccc   180
agagaggaac ctagagcccc ttggatcgag caggaaggcc ccgagtactg ggaccggaac   240
acccagatct tcaagaccaa tacccagacc gacagagaga gcctgcgaaa cctgcggggc   300
tactacaatc agagcgaggc cggctctcac accctgcagt ctatgtacgg ctgcgacgtg   360
ggccccgatg gcagactgct gagaggccac aacgagtacg cctacgacgg caaggactat   420
atcgccctga cgaggacct gcggagctgg acagccgccg atacagccgc ccagatcacc   480
cagagaaagt gggaggccgc cagagtggcc gagcaggata gagcctacct ggaaggcacc   540
```

```
tgtgtggaat ggctgcggag atacctggaa aatggcaagg acaccctgga acgcacagat    600
tccccaaagg cccatgtgac ccatcacagc agacctgaag ataaagtcac cctgaggtgc    660
tgggccctgg gcttctaccc tgctgacatc accctgacct ggcagttgaa tggggaggag    720
ctgatccagg acatggagct tgtggagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg gcagccacca ccaccatcac    900
cattga                                                              906

SEQ ID NO: 22           moltype = AA   length = 302
FEATURE                 Location/Qualifiers
source                  1..302
                        mol_type = protein
                        organism = Homo sapiens
SEQUENCE: 22
MMRPIVLVLL FATSALAGSH SMRYFDTAMS RPGRGEPRFI SVGYVDDTQF VRFDSDAASP     60
REEPRAPWIE QEGPEYWDRN TQIFKTNTQT DRESLRNLRG YYNQSEAGSH TLQSMYGCDV    120
GPDGRLLRGH NEYAYDGKDY IALNEDLRSW TAADTAAQIT QRKWEAARVA EQDRAYLEGT    180
CVEWLRRYLE NGKDTLERTD SPKAHVTHHS RPEDKVTLRC WALGFYPADI TLTWQLNGEE    240
LIQDMELVET RPAGDGTFQK WASVVVPLGK EQYYTCHVYH QGLPEPLTLR WEPGSHHHHH    300
HZ                                                                  302

SEQ ID NO: 23           moltype = DNA   length = 906
FEATURE                 Location/Qualifiers
source                  1..906
                        mol_type = genomic DNA
                        organism = Homo sapiens
SEQUENCE: 23
atgatgcggc ccatcgtgct ggtgctgctg tttgccacaa gcgccctggc ctgctctcac     60
agcatgcgct attttacac ggcagttagt cggcctggga gggtgagcc gagattcatt     120
gctgtaggct acgtagacga cactcaattt gtacagttcg actcagacgc tgcttcaccg    180
cgaggagagc ccagggcacc ctgggtagaa caagaaggc ccgaatactg ggatcgagaa     240
acccagaagt ataagaggca agcacaaact gatcgggtca acttgagaaa actgcgaggc    300
tactataatc aaagtgaggc aggatccat acacttcaga ggatgtatgg ctgcgaccttt    360
ggtccagatg gccggctcct cagagggtat aacgaatttg catacgacgg aaggattac    420
atagctctca atgaggacct tagatcatgg acggcagcgg ataaggcagc ccaaattact    480
caaaggaaat gggaggcggc ccgagaagca gagcagagaa gagcctacct ggaaggtaca    540
tgcgtggagt ggcttcggcg ctatctcgaa aacggtaaaa agacattgca acgcacagat    600
tccccaaagg cccatgtgac ccatcacagc agacctgaag ataaagtcac cctgaggtgc    660
tgggccctgg gcttctaccc tgctgacatc accctgacct ggcagttgaa tggggaggag    720
ctgatccagg acatggagct tgtggagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg gcagccacca ccaccatcac    900
cattga                                                              906

SEQ ID NO: 24           moltype = AA   length = 302
FEATURE                 Location/Qualifiers
source                  1..302
                        mol_type = protein
                        organism = Homo sapiens
SEQUENCE: 24
MMRPIVLVLL FATSALACSH SMRYFYTAVS RPGRGEPRFI AVGYVDDTQF VQFDSDAASP     60
RGEPRAPWVE QEGPEYWDRE TQKYKRQAQT DRVNLRKLRG YYNQSEAGSH TLQRMYGCDL    120
GPDGRLLRGY NEFAYDGKDY IALNEDLRSW TAADKAAQIT QRKWEAAREA EQRRAYLEGT    180
CVEWLRRYLE NGKKTLQRTD SPKAHVTHHS RPEDKVTLRC WALGFYPADI TLTWQLNGEE    240
LIQDMELVET RPAGDGTFQK WASVVVPLGK EQYYTCHVYH QGLPEPLTLR WEPGSHHHHH    300
HZ                                                                  302

SEQ ID NO: 25           moltype = DNA   length = 906
FEATURE                 Location/Qualifiers
source                  1..906
                        mol_type = genomic DNA
                        organism = Homo sapiens
SEQUENCE: 25
atgatgcggc ccatcgtgct ggtgctgctg tttgccacaa gcgccctggc ctgcagccac     60
agcatgcggt actttgacac cgccgtgtcc agacccggaa gaggcgagcc cagattcatc    120
agcgtgggct acgtggacga cacccagttc gtcagattcg acagcgacgc cgccagcccc    180
agaggcgaac ctagagcacc ttgggtggaa caggaaggcc ccgagtactg ggacagagag    240
acacagaact acaagcggca ggcccaggcc gacagagtgt ccctgagaaa cctgcggggc    300
tactacaacc agagcgagga cggcagcgga cccctgcac gaatgtacgg ctgtgacctg    360
ggccccgatg gcagactgct gagaggctac gatgagagcg cctacgacgg caaggactat    420
atcgccctga acgaggacct gcggagctgg acagccgccg atacagcgc ccagatcacc    480
cagagaaaac tggaagccgc cagagccgcc gagcagctga gcttatctg ggaaggcacc    540
tgtgtggaat ggctgcggag atacctggaa aacggcaaag agacactgca gcgcacagat    600
tccccaaagg cccatgtgac ccatcacagc agacctgaag ataaagtcac cctgaggtgc    660
tgggccctgg gcttctaccc tgctgacatc accctgacct ggcagttgaa tggggaggag    720
ctgatccagg acatggagct tgtggagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg gcagccacca ccaccatcac    900
cattga                                                              906
```

SEQ ID NO: 26          moltype = AA  length = 302
FEATURE                Location/Qualifiers
source                 1..302
                       mol_type = protein
                       organism = Homo sapiens
SEQUENCE: 26
MMRPIVLVLL FATSALACSH SMRYFDTAVS RPGRGEPRFI SVGYVDDTQF VRFDSDAASP   60
RGEPRAPWVE QEGPEYWDRE TQNYKRQAQA DRVSLRNLRG YYNQSEDGSH TLQRMYGCDL  120
GPDGRLLRGY DESAYDGKDY IALNEDLRSW TAADTAAQIT QRKLEAARAA EQLRAYLEGT  180
CVEWLRRYLE NGKETLQRTD SPKAHVTHHS RPEDKVTLRC WALGFYPADI TLTWQLNGEE  240
LIQDMELVET RPAGDGTFQK WASVVVPLGK EQYYTCHVYH QGLPEPLTLR WEPGSHHHHH  300
HZ                                                                302

SEQ ID NO: 27          moltype = DNA  length = 906
FEATURE                Location/Qualifiers
source                 1..906
                       mol_type = genomic DNA
                       organism = Homo sapiens
SEQUENCE: 27
atgatgcggc ccatcgtgct ggtgctgctg tttgccacat ctgccctggc ctgcagccac   60
agcatgcggt actttgacac cgccgtgtcc agacccgaaa gaggcgagcc cagattcatc  120
agcgtgggct acgtggacga cacccagttc gtcagattcg acagcgacgc cgccagcccc  180
agaggcgaaa ctagagcacc ttgggtggaa caggaaggcc ccgagtactg ggacagagag  240
acacagaagt acaagcggca ggcccaggcc gacagagtgt ccctgagaaa cctgcgggcc  300
tactacaacc agagcgagga cggccaccac ccctgcagta caatgcgccg ctgtgacctg  360
ggcccccgatg gcagactgct gagaggctac gatgagagcg cctacgacgg caaggactat  420
atcgccctga cgaggacct gcggagctgg acagccgccg atacagccgc ccagatcacc  480
cagagaaaac tggaagccgc cagagccgcc gagcagctga gagcttatct ggaaggcacc  540
tgtgtggaat ggctgcggag atacctgaa aacggcaaag agacactgca gcgcacagat  600
tccccaaagg cccatgtgac ccatcacagc agacctgaag ataaagtcac cctgaggtgc  660
tgggccctgg gcttctaccc tgctgacatc accctgacct ggcagttgaa tggggaggag  720
ctgatccagg acatggagct tgtggagacc aggcctgcag ggatggaac cttccagaag  780
tgggcatctg tggtggtgcc tcttgggaag gagcagtatt acacatgcca tgtgtaccat  840
caggggctgc ctgagcccct caccctgaga tgggagccgg cagccacca ccaccatcac  900
cattga                                                            906

SEQ ID NO: 28          moltype = AA  length = 302
FEATURE                Location/Qualifiers
source                 1..302
                       mol_type = protein
                       organism = Homo sapiens
SEQUENCE: 28
MMRPIVLVLL FATSALACSH SMRYFDTAVS RPGRGEPRFI SVGYVDDTQF VRFDSDAASP   60
RGEPRAPWVE QEGPEYWDRE TQKYKRQAQA DRVSLRNLRG YYNQSEDGSH TLQRMSGCDL  120
GPDGRLLRGY DESAYDGKDY IALNEDLRSW TAADTAAQIT QRKLEAARAA EQLRAYLEGT  180
CVEWLRRYLE NGKETLQRTD SPKAHVTHHS RPEDKVTLRC WALGFYPADI TLTWQLNGEE  240
LIQDMELVET RPAGDGTFQK WASVVVPLGK EQYYTCHVYH QGLPEPLTLR WEPGSHHHHH  300
HZ                                                                302

SEQ ID NO: 29          moltype = DNA  length = 906
FEATURE                Location/Qualifiers
source                 1..906
                       mol_type = genomic DNA
                       organism = Homo sapiens
SEQUENCE: 29
atgatgaggc ccatcgtgct ggtgctgctg ttcgccacat ctgccctggc ctgcagccac   60
agcatgcggt acttttacac cgccgtgtcc agacccggca gaggcgagcc tagattcatt  120
gccgtgggct acgtggacga cacccagttc gtcagattcg acagcgacgc cgccagcccc  180
agaggggaac ctagagcacc ttgggtggaa caggaaggcc ccgagtactg ggacagagag  240
acacagaagt acaagcggca ggcccagacc gaccgggtgt ccctgagaaa cctgcgggcc  300
tactacaacc agagcgaggc cggctctcac accctgcagt ggatgtacgg ctgcgacctg  360
ggccctgatg gcagactgct gagaggctac gacgagtccg cctacgacgg caaggactat  420
atcgccctga cgaggacct gcggagctgg acagccgcc atacagccgc ccagatcacc  480
cagagaaagt gggaagccgc cagagccgcc gagcagcaga gagcttatct ggaaggcacc  540
tgtgtggaat ggctgcggag atacctgaa aacggcaaag agacactgca gcgcacagat  600
tccccaaagg cccatgtgac ccatcacagc agacctgaag ataaagtcac cctgaggtgc  660
tgggccctgg gcttctaccc tgctgacatc accctgacct ggcagttgaa tggggaggag  720
ctgatccagg acatggagct tgtggagacc aggcctgcag ggatggaac cttccagaag  780
tgggcatctg tggtggtgcc tcttgggaag gagcagtatt acacatgcca tgtgtaccat  840
caggggctgc ctgagcccct caccctgaga tgggagccgg cagccacca ccaccatcac  900
cattga                                                            906

SEQ ID NO: 30          moltype = AA  length = 302
FEATURE                Location/Qualifiers
source                 1..302
                       mol_type = protein
                       organism = Homo sapiens
SEQUENCE: 30

```
MMRPIVLVLL FATSALACSH SMRYFYTAVS RPGRGEPRFI AVGYVDDTQF VRFDSDAASP    60
RGEPRAPWVE QEGPEYWDRE TQKYKRQAQT DRVSLRNLRG YYNQSEAGSH TLQWMYGCDL   120
GPDGRLLRGY DESAYDGKDY IALNEDLRSW TAADTAAQIT QRKWEAARAA EQQRAYLEGT   180
CVEWLRRYLE NGKETLQRTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                 302

SEQ ID NO: 31           moltype = DNA   length = 906
FEATURE                 Location/Qualifiers
source                  1..906
                        mol_type = genomic DNA
                        organism = Homo sapiens
SEQUENCE: 31
atgatgcggc ccatcgtgct ggtgctgctg tttgccacat ctgccctggc cggctcccac    60
tccatgaggt atttctacac cgccatgtcc cggcccggcc gcggggagcc ccgcttcatc   120
gcagtgggct acgtggacga cacccagttc gtgaggttcg acagcgacgc cgcgagtccg   180
aggacggagc cccgggcgcc atggatagag caggaggggc cggagtattg ggaccggaac   240
acacagatct tcaagaccaa cacacagact taccgagaga gcctgcggaa cctgcgcggc   300
tactacaacc agagcgaggc cgggtctcac atcatccaga ggatgtatgg ctgcgacctg   360
gggcccgacg gcgcctcct ccgcgggcat gaccagtccg cctacgacgg caaggattac   420
atcgccctga cgaggacct gagctcctgg accgcgcgg acaccgcggc tcagatcacc   480
cagcgcaagt gggaggcggc ccgtgtggcg gagcagctga gagcctacct ggagggcctg   540
tgcgtggagt ggctccgcag atacctggag aacgggaagg agacgctgca gcgcgcggga   600
ccccaaaga cacacgtgac ccaccacccc gtctctgacc atgaggccac cctgaggtgc   660
tgggccctgg gcttctaccc tgcggagatc acactgacct ggcagcggga tggcgaggac   720
caaactcagg acactgagct tgtggagacc agaccagcag gagatagaac cttccagaag   780
tgggcagctg tggtggtgcc ttctggagaa gagcagagat acacatgcca tgtacagcat   840
gaggggctgc ccaagcccct cacccctgaga tgggagccgg gcagccacca ccaccatcac   900
cattga                                                             906

SEQ ID NO: 32           moltype = AA   length = 302
FEATURE                 Location/Qualifiers
source                  1..302
                        mol_type = protein
                        organism = Homo sapiens
SEQUENCE: 32
MMRPIVLVLL FATSALAGSH SMRYFYTAMS RPGRGEPRFI AVGYVDDTQF VRFDSDAASP    60
RTEPRAPWIE QEGPEYWDRN TQIFKTNTQT YRESLRNLRG YYNQSEAGSH IIQRMYGCDL   120
GPDGRLLRGH DQSAYDGKDY IALNEDLSSW TAADTAAQIT QRKWEAARVA EQLRAYLEGL   180
CVEWLRRYLE NGKETLQRAD PPKTHVTHHP VSDHEATLRC WALGFYPAEI TLTWQRDGED   240
QTQDTELVET RPAGDRTFQK WAAVVVPSGE EQRYTCHVQH EGLPKPLTLR WEPGSHHHHH   300
HZ                                                                 302

SEQ ID NO: 33           moltype = DNA   length = 906
FEATURE                 Location/Qualifiers
source                  1..906
                        mol_type = genomic DNA
                        organism = Homo sapiens
SEQUENCE: 33
atgatgcggc ccatcgtgct ggtgctgctg tttgccacat ctgccctggc cggctcccac    60
tccatgaggt atttctacac cgccatgtcc cggcccggcc gcggggagcc ccgcttcatc   120
gcagtgggct acgtggacga cacccagttc gtgaggttcg acagcgacgc cgcgagtccg   180
aggacggagc cccgggcgcc atggatagag caggaggggc cggagtattg ggaccggaac   240
acacagatct tcaagaccaa cacacagact taccgagaga gcctgcggaa cctgcgcggc   300
tactacaacc agagcgaggc cgggtctcac atcatccaga ggatgtatgg ctgcgacctg   360
gggcccgacg gcgcctcct ccgcgggcat gaccagtccg cctacgacgg caaggattac   420
atcgccctga cgaggacct gagctcctgg accgcgcgg acaccgcggc tcagatcacc   480
cagcgcaagt gggaggcggc ccgtgtggcg gagcagctga gagcctacct ggagggcctg   540
tgcgtggagt ggctccgcag atacctggag aacgggaagg agacgctgca gcgcgcagat   600
tcccccaaaga cccatgtgac ccatcacagc agacctgacc cctgaggtgc   660
tgggccctgg gcttctaccc tgctgacatc accctgacct ggcagttgaa tggggaggag   720
ctgatccagg acatggagct tgtggagacc aggcctgcag ggatggaac cttccagaag   780
tgggcatctg tggtggtgcc tcttgggaag gagcagtatt acacatgcca tgtgtaccat   840
caggggctgc ctgagcccct cacccctgaga tgggagccgg gcagccacca ccaccatcac   900
cattga                                                             906

SEQ ID NO: 34           moltype = AA   length = 302
FEATURE                 Location/Qualifiers
source                  1..302
                        mol_type = protein
                        organism = Homo sapiens
SEQUENCE: 34
MMRPIVLVLL FATSALAGSH SMRYFYTAMS RPGRGEPRFI AVGYVDDTQF VRFDSDAASP    60
RTEPRAPWIE QEGPEYWDRN TQIFKTNTQT YRESLRNLRG YYNQSEAGSH IIQRMYGCDL   120
GPDGRLLRGH DQSAYDGKDY IALNEDLSSW TAADTAAQIT QRKWEAARVA EQLRAYLEGL   180
CVEWLRRYLE NGKETLQRTD SPKAHVTHHS RPEDKVTLRC WALGFYPADI TLTWQLNGEE   240
LIQDMELVET RPAGDGTFQK WASVVVPLGK EQYYTCHVYH QGLPEPLTLR WEPGSHHHHH   300
HZ                                                                 302
```

-continued

| SEQ ID NO: 35
FEATURE
source

SEQUENCE: 35
VLDFAPPGA | moltype = AA length = 9
Location/Qualifiers
1..9
mol_type = protein
note = Peptide fragment
organism = synthetic construct

| 9 |
|---|---|---|
| SEQ ID NO: 36
FEATURE
source

SEQUENCE: 36
RMFPNAPYL | moltype = AA length = 9
Location/Qualifiers
1..9
mol_type = protein
note = Peptide fragment
organism = synthetic construct

| 9 |
| SEQ ID NO: 37
FEATURE
source

SEQUENCE: 37
SLGEQQYSV | moltype = AA length = 9
Location/Qualifiers
1..9
mol_type = protein
note = Peptide fragment
organism = synthetic construct

| 9 |
| SEQ ID NO: 38
FEATURE
source

SEQUENCE: 38
CMTWNQMNL | moltype = AA length = 9
Location/Qualifiers
1..9
mol_type = protein
note = Peptide fragment
organism = synthetic construct

| 9 |
| SEQ ID NO: 39
FEATURE
source

SEQUENCE: 39
YMAPDCRFL | moltype = AA length = 9
Location/Qualifiers
1..9
mol_type = protein
note = Peptide fragment
organism = synthetic construct

| 9 |
| SEQ ID NO: 40
FEATURE
source

SEQUENCE: 40
RLGYFPSSI | moltype = AA length = 9
Location/Qualifiers
1..9
mol_type = protein
note = Peptide fragment
organism = synthetic construct

| 9 |
| SEQ ID NO: 41
FEATURE
source

SEQUENCE: 41
LQLEELEKV | moltype = AA length = 9
Location/Qualifiers
1..9
mol_type = protein
note = Peptide fragment
organism = synthetic construct

| 9 |
| SEQ ID NO: 42
FEATURE
source

SEQUENCE: 42
ELTEARVQV | moltype = AA length = 9
Location/Qualifiers
1..9
mol_type = protein
note = Peptide fragment
organism = synthetic construct

| 9 |
| SEQ ID NO: 43
FEATURE
source

SEQUENCE: 43 | moltype = AA length = 9
Location/Qualifiers
1..9
mol_type = protein
note = Peptide fragment
organism = synthetic construct

|  |

```
FLGDTHSSI                                                                              9

SEQ ID NO: 44         moltype = AA  length = 9
FEATURE               Location/Qualifiers
source                1..9
                      mol_type = protein
                      note = Peptide fragment
                      organism = synthetic construct
SEQUENCE: 44
ILAYTEDEV                                                                              9

SEQ ID NO: 45         moltype = AA  length = 10
FEATURE               Location/Qualifiers
source                1..10
                      mol_type = protein
                      note = Peptide fragment
                      organism = synthetic construct
SEQUENCE: 45
FLEEIKEQEV                                                                             10

SEQ ID NO: 46         moltype = AA  length = 9
FEATURE               Location/Qualifiers
source                1..9
                      mol_type = protein
                      note = Peptide fragment
                      organism = synthetic construct
SEQUENCE: 46
FMAFVAMVT                                                                              9

SEQ ID NO: 47         moltype = AA  length = 9
FEATURE               Location/Qualifiers
source                1..9
                      mol_type = protein
                      note = Peptide fragment
                      organism = synthetic construct
SEQUENCE: 47
LLDEATSAL                                                                              9

SEQ ID NO: 48         moltype = AA  length = 9
FEATURE               Location/Qualifiers
source                1..9
                      mol_type = protein
                      note = Peptide fragment
                      organism = synthetic construct
SEQUENCE: 48
VLNGTVHPV                                                                              9

SEQ ID NO: 49         moltype = AA  length = 9
FEATURE               Location/Qualifiers
source                1..9
                      mol_type = protein
                      note = Peptide fragment
                      organism = synthetic construct
SEQUENCE: 49
VLLSPRWEL                                                                              9

SEQ ID NO: 50         moltype = AA  length = 9
FEATURE               Location/Qualifiers
source                1..9
                      mol_type = protein
                      note = Peptide fragment
                      organism = synthetic construct
SEQUENCE: 50
FLWDAYFSS                                                                              9

SEQ ID NO: 51         moltype = AA  length = 9
FEATURE               Location/Qualifiers
source                1..9
                      mol_type = protein
                      note = Peptide fragment
                      organism = synthetic construct
SEQUENCE: 51
WLALSASWL                                                                              9

SEQ ID NO: 52         moltype = AA  length = 9
FEATURE               Location/Qualifiers
source                1..9
                      mol_type = protein
                      note = Peptide fragment
```

```
                                 -continued

SEQUENCE: 52
LLLPGIYTV                                                                  9

SEQ ID NO: 53        moltype = AA   length = 9
FEATURE              Location/Qualifiers
source               1..9
                     mol_type = protein
                     note = Peptide fragment
                     organism = synthetic construct SEQUENCE: 53
KLFQKLAKV                                                                  9

SEQ ID NO: 54        moltype = AA   length = 9
FEATURE              Location/Qualifiers
source               1..9
                     mol_type = protein
                     note = Peptide fragment
                     organism = synthetic construct SEQUENCE: 54
YLHTNCFEI                                                                  9

SEQ ID NO: 55        moltype = AA   length = 9
FEATURE              Location/Qualifiers
source               1..9
                     mol_type = protein
                     note = Peptide fragment
                     organism = synthetic construct SEQUENCE: 55
FLSNFPFSL                                                                  9

SEQ ID NO: 56        moltype = AA   length = 9
FEATURE              Location/Qualifiers
source               1..9
                     mol_type = protein
                     note = Peptide fragment
                     organism = synthetic construct SEQUENCE: 56
ALAIGLWGL                                                                  9

SEQ ID NO: 57        moltype = AA   length = 9
FEATURE              Location/Qualifiers
source               1..9
                     mol_type = protein
                     note = Peptide fragment
                     organism = synthetic construct SEQUENCE: 57
ALCENTCLL                                                                  9

SEQ ID NO: 58        moltype = AA   length = 9
FEATURE              Location/Qualifiers
source               1..9
                     mol_type = protein
                     note = Peptide fragment
                     organism = synthetic construct SEQUENCE: 58
LLYPGYAMV                                                                  9

SEQ ID NO: 59        moltype = AA   length = 9
FEATURE              Location/Qualifiers
source               1..9
                     mol_type = protein
                     note = Peptide fragment
                     organism = synthetic construct SEQUENCE: 59
GLYTLLSGV                                                                  9

SEQ ID NO: 60        moltype = AA   length = 9
FEATURE              Location/Qualifiers
source               1..9
                     mol_type = protein
                     note = Peptide fragment
                     organism = synthetic construct SEQUENCE: 60
AVFMYVFYL                                                                  9

SEQ ID NO: 61        moltype = AA   length = 9
FEATURE              Location/Qualifiers
source               1..9
```

```
                        mol_type = protein
                        note = Peptide fragment
                        organism = synthetic construct
SEQUENCE: 61
LMDDTLSPV                                                               9

SEQ ID NO: 62           moltype = AA   length = 9
FEATURE                 Location/Qualifiers
source                  1..9
                        mol_type = protein
                        note = Peptide fragment
                        organism = synthetic construct
SEQUENCE: 62
LQMANTLPV                                                               9

SEQ ID NO: 63           moltype = AA   length = 9
FEATURE                 Location/Qualifiers
source                  1..9
                        mol_type = protein
                        note = Peptide fragment
                        organism = synthetic construct
SEQUENCE: 63
LLSSVSPGA                                                               9

SEQ ID NO: 64           moltype = AA   length = 9
FEATURE                 Location/Qualifiers
source                  1..9
                        mol_type = protein
                        note = Peptide fragment
                        organism = synthetic construct
SEQUENCE: 64
SQFVFSFPV                                                               9

SEQ ID NO: 65           moltype = AA   length = 9
FEATURE                 Location/Qualifiers
source                  1..9
                        mol_type = protein
                        note = Peptide fragment
                        organism = synthetic construct
SEQUENCE: 65
QLLQFESQV                                                               9

SEQ ID NO: 66           moltype = AA   length = 9
FEATURE                 Location/Qualifiers
source                  1..9
                        mol_type = protein
                        note = Peptide fragment
                        organism = synthetic construct
SEQUENCE: 66
FLAHSAGYI                                                               9

SEQ ID NO: 67           moltype = AA   length = 9
FEATURE                 Location/Qualifiers
source                  1..9
                        mol_type = protein
                        note = Peptide fragment
                        organism = synthetic construct
SEQUENCE: 67
FLDRFLSCM                                                               9

SEQ ID NO: 68           moltype = AA   length = 11
FEATURE                 Location/Qualifiers
source                  1..11
                        mol_type = protein
                        note = Peptide fragment
                        organism = synthetic construct
SEQUENCE: 68
SLIAAAAFCL A                                                           11

SEQ ID NO: 69           moltype = AA   length = 9
FEATURE                 Location/Qualifiers
source                  1..9
                        mol_type = protein
                        note = Peptide fragment
                        organism = synthetic construct
SEQUENCE: 69
MLAVISCAV                                                               9

SEQ ID NO: 70           moltype = AA   length = 11
```

```
FEATURE                     Location/Qualifiers
source                      1..11
                            mol_type = protein
                            note = Peptide fragment
                            organism = synthetic construct
SEQUENCE: 70
MLMAQEALAF L                                                                    11

SEQ ID NO: 71               moltype = AA  length = 9
FEATURE                     Location/Qualifiers
source                      1..9
                            mol_type = protein
                            note = Peptide fragment
                            organism = synthetic construct
SEQUENCE: 71
KVLEYVIKV                                                                       9

SEQ ID NO: 72               moltype = AA  length = 10
FEATURE                     Location/Qualifiers
source                      1..10
                            mol_type = protein
                            note = Peptide fragment
                            organism = synthetic construct
SEQUENCE: 72
YLQLVFGIEV                                                                      10

SEQ ID NO: 73               moltype = AA  length = 9
FEATURE                     Location/Qualifiers
source                      1..9
                            mol_type = protein
                            note = Peptide fragment
                            organism = synthetic construct
SEQUENCE: 73
FLWGPRALV                                                                       9

SEQ ID NO: 74               moltype = AA  length = 9
FEATURE                     Location/Qualifiers
source                      1..9
                            mol_type = protein
                            note = Peptide fragment
                            organism = synthetic construct
SEQUENCE: 74
KVAELVHFL                                                                       9

SEQ ID NO: 75               moltype = AA  length = 10
FEATURE                     Location/Qualifiers
source                      1..10
                            mol_type = protein
                            note = Peptide fragment
                            organism = synthetic construct
SEQUENCE: 75
GVYDGREHTV                                                                      10

SEQ ID NO: 76               moltype = AA  length = 9
FEATURE                     Location/Qualifiers
source                      1..9
                            mol_type = protein
                            note = Peptide fragment
                            organism = synthetic construct
SEQUENCE: 76
ALSVMGVYV                                                                       9

SEQ ID NO: 77               moltype = AA  length = 9
FEATURE                     Location/Qualifiers
source                      1..9
                            mol_type = protein
                            note = Peptide fragment
                            organism = synthetic construct
SEQUENCE: 77
GLYDGMEHL                                                                       9

SEQ ID NO: 78               moltype = AA  length = 9
FEATURE                     Location/Qualifiers
source                      1..9
                            mol_type = protein
                            note = Peptide fragment
                            organism = synthetic construct
SEQUENCE: 78
FLWGPRALV                                                                       9
```

```
SEQ ID NO: 79           moltype = AA  length = 10
FEATURE                 Location/Qualifiers
source                  1..10
                        mol_type = protein
                        note = Peptide fragment
                        organism = synthetic construct
SEQUENCE: 79
ILFGISLREV                                                                    10

SEQ ID NO: 80           moltype = AA  length = 9
FEATURE                 Location/Qualifiers
source                  1..9
                        mol_type = protein
                        note = Peptide fragment
                        organism = synthetic construct
SEQUENCE: 80
KVVEFLAML                                                                      9

SEQ ID NO: 81           moltype = AA  length = 11
FEATURE                 Location/Qualifiers
source                  1..11
                        mol_type = protein
                        note = Peptide fragment
                        organism = synthetic construct
SEQUENCE: 81
MLMAQEALAF L                                                                  11

SEQ ID NO: 82           moltype = AA  length = 9
FEATURE                 Location/Qualifiers
source                  1..9
                        mol_type = protein
                        note = Peptide fragment
                        organism = synthetic construct
SEQUENCE: 82
KASEKIFYV                                                                      9

SEQ ID NO: 83           moltype = AA  length = 9
FEATURE                 Location/Qualifiers
source                  1..9
                        mol_type = protein
                        note = Peptide fragment
                        organism = synthetic construct
SEQUENCE: 83
RQKKIRIQL                                                                      9

SEQ ID NO: 84           moltype = AA  length = 9
FEATURE                 Location/Qualifiers
source                  1..9
                        mol_type = protein
                        note = Peptide fragment
                        organism = synthetic construct
SEQUENCE: 84
IMIGVLVGV                                                                      9

SEQ ID NO: 85           moltype = AA  length = 9
FEATURE                 Location/Qualifiers
source                  1..9
                        mol_type = protein
                        note = Peptide fragment
                        organism = synthetic construct
SEQUENCE: 85
KTWGQYWQV                                                                      9

SEQ ID NO: 86           moltype = AA  length = 10
FEATURE                 Location/Qualifiers
source                  1..10
                        mol_type = protein
                        note = Peptide fragment
                        organism = synthetic construct
SEQUENCE: 86
AMLGTHTMEV                                                                    10

SEQ ID NO: 87           moltype = AA  length = 9
FEATURE                 Location/Qualifiers
source                  1..9
                        mol_type = protein
                        note = Peptide fragment
                        organism = synthetic construct
```

```
SEQUENCE: 87
MLGTHTMEV                                                                        9

SEQ ID NO: 88           moltype = AA  length = 9
FEATURE                 Location/Qualifiers
source                  1..9
                        mol_type = protein
                        note = Peptide fragment
                        organism = synthetic construct
SEQUENCE: 88
ITDQVPFSV                                                                        9

SEQ ID NO: 89           moltype = AA  length = 9
FEATURE                 Location/Qualifiers
source                  1..9
                        mol_type = protein
                        note = Peptide fragment
                        organism = synthetic construct
SEQUENCE: 89
YLEPGPVTA                                                                        9

SEQ ID NO: 90           moltype = AA  length = 10
FEATURE                 Location/Qualifiers
source                  1..10
                        mol_type = protein
                        note = Peptide fragment
                        organism = synthetic construct
SEQUENCE: 90
LLDGTATLRL                                                                      10

SEQ ID NO: 91           moltype = AA  length = 10
FEATURE                 Location/Qualifiers
source                  1..10
                        mol_type = protein
                        note = Peptide fragment
                        organism = synthetic construct
SEQUENCE: 91
VLYRYGSFSV                                                                      10

SEQ ID NO: 92           moltype = AA  length = 10
FEATURE                 Location/Qualifiers
source                  1..10
                        mol_type = protein
                        note = Peptide fragment
                        organism = synthetic construct
SEQUENCE: 92
SLADTNSLAV                                                                      10

SEQ ID NO: 93           moltype = AA  length = 9
FEATURE                 Location/Qualifiers
source                  1..9
                        mol_type = protein
                        note = Peptide fragment
                        organism = synthetic construct
SEQUENCE: 93
RLMKQDFSV                                                                        9

SEQ ID NO: 94           moltype = AA  length = 9
FEATURE                 Location/Qualifiers
source                  1..9
                        mol_type = protein
                        note = Peptide fragment
                        organism = synthetic construct
SEQUENCE: 94
RLPRIFCSC                                                                        9

SEQ ID NO: 95           moltype = AA  length = 9
FEATURE                 Location/Qualifiers
source                  1..9
                        mol_type = protein
                        note = Peptide fragment
                        organism = synthetic construct
SEQUENCE: 95
SLSKILDTV                                                                        9

SEQ ID NO: 96           moltype = AA  length = 9
FEATURE                 Location/Qualifiers
source                  1..9
                        mol_type = protein
```

```
                              note = Peptide fragment
                              organism = synthetic construct
SEQUENCE: 96
SVYDFFVWL                                                                  9

SEQ ID NO: 97                 moltype = AA   length = 9
FEATURE                       Location/Qualifiers
source                        1..9
                              mol_type = protein
                              note = Peptide fragment
                              organism = synthetic construct
SEQUENCE: 97
TLDSQVMSL                                                                  9

SEQ ID NO: 98                 moltype = AA   length = 9
FEATURE                       Location/Qualifiers
source                        1..9
                              mol_type = protein
                              note = Peptide fragment
                              organism = synthetic construct
SEQUENCE: 98
MLLAVLYCL                                                                  9

SEQ ID NO: 99                 moltype = AA   length = 10
FEATURE                       Location/Qualifiers
source                        1..10
                              mol_type = protein
                              note = Peptide fragment
                              organism = synthetic construct
SEQUENCE: 99
CLLWSFQTSA                                                                10

SEQ ID NO: 100                moltype = AA   length = 9
FEATURE                       Location/Qualifiers
source                        1..9
                              mol_type = protein
                              note = Peptide fragment
                              organism = synthetic construct
SEQUENCE: 100
YMDGTMSQV                                                                  9

SEQ ID NO: 101                moltype = AA   length = 9
FEATURE                       Location/Qualifiers
source                        1..9
                              mol_type = protein
                              note = Peptide fragment
                              organism = synthetic construct
SEQUENCE: 101
LLNAFTVTV                                                                  9

SEQ ID NO: 102                moltype = AA   length = 9
FEATURE                       Location/Qualifiers
source                        1..9
                              mol_type = protein
                              note = Peptide fragment
                              organism = synthetic construct
SEQUENCE: 102
KVHPVIWSL                                                                  9

SEQ ID NO: 103                moltype = AA   length = 10
FEATURE                       Location/Qualifiers
source                        1..10
                              mol_type = protein
                              note = Peptide fragment
                              organism = synthetic construct
SEQUENCE: 103
LMLQNALTTM                                                                10

SEQ ID NO: 104                moltype = AA   length = 9
FEATURE                       Location/Qualifiers
source                        1..9
                              mol_type = protein
                              note = Peptide fragment
                              organism = synthetic construct
SEQUENCE: 104
LLGATCMFV                                                                  9

SEQ ID NO: 105                moltype = AA   length = 9
FEATURE                       Location/Qualifiers
```

-continued

```
source                          1..9
                                mol_type = protein
                                note = Peptide fragment
                                organism = synthetic construct
SEQUENCE: 105
ALLEIASCL                                                                      9

SEQ ID NO: 106                  moltype = AA   length = 8
FEATURE                         Location/Qualifiers
source                          1..8
                                mol_type = protein
                                note = Peptide fragment
                                organism = synthetic construct
SEQUENCE: 106
VLFYLGQY                                                                       8

SEQ ID NO: 107                  moltype = AA   length = 9
FEATURE                         Location/Qualifiers
source                          1..9
                                mol_type = protein
                                note = Peptide fragment
                                organism = synthetic construct
SEQUENCE: 107
LLGRNSFEV                                                                      9

SEQ ID NO: 108                  moltype = AA   length = 9
FEATURE                         Location/Qualifiers
source                          1..9
                                mol_type = protein
                                note = Peptide fragment
                                organism = synthetic construct
SEQUENCE: 108
RMPEAAPPV                                                                      9

SEQ ID NO: 109                  moltype = AA   length = 9
FEATURE                         Location/Qualifiers
source                          1..9
                                mol_type = protein
                                note = Peptide fragment
                                organism = synthetic construct
SEQUENCE: 109
VLDGLDVLL                                                                      9

SEQ ID NO: 110                  moltype = AA   length = 10
FEATURE                         Location/Qualifiers
source                          1..10
                                mol_type = protein
                                note = Peptide fragment
                                organism = synthetic construct
SEQUENCE: 110
SLYSFPEPEA                                                                    10

SEQ ID NO: 111                  moltype = AA   length = 10
FEATURE                         Location/Qualifiers
source                          1..10
                                mol_type = protein
                                note = Peptide fragment
                                organism = synthetic construct
SEQUENCE: 111
ALYVDSLFFL                                                                    10

SEQ ID NO: 112                  moltype = AA   length = 9
FEATURE                         Location/Qualifiers
source                          1..9
                                mol_type = protein
                                note = Peptide fragment
                                organism = synthetic construct
SEQUENCE: 112
SLLQHLIGL                                                                      9

SEQ ID NO: 113                  moltype = AA   length = 9
FEATURE                         Location/Qualifiers
source                          1..9
                                mol_type = protein
                                note = Peptide fragment
                                organism = synthetic construct
SEQUENCE: 113
AWISKPPGV                                                                      9
```

| | | |
|---|---|---|
| SEQ ID NO: 114<br>FEATURE<br>source | moltype = AA   length = 10<br>Location/Qualifiers<br>1..10<br>mol_type = protein<br>note = Peptide fragment<br>organism = synthetic construct | |
| SEQUENCE: 114<br>SAWISKPPGV | | 10 |
| SEQ ID NO: 115<br>FEATURE<br>source | moltype = AA   length = 10<br>Location/Qualifiers<br>1..10<br>mol_type = protein<br>note = Peptide fragment<br>organism = synthetic construct | |
| SEQUENCE: 115<br>ELTLGEFLKL | | 10 |
| SEQ ID NO: 116<br>FEATURE<br>source | moltype = AA   length = 9<br>Location/Qualifiers<br>1..9<br>mol_type = protein<br>note = Peptide fragment<br>organism = synthetic construct | |
| SEQUENCE: 116<br>RLVDDFLLV | | 9 |
| SEQ ID NO: 117<br>FEATURE<br>source | moltype = AA   length = 9<br>Location/Qualifiers<br>1..9<br>mol_type = protein<br>note = Peptide fragment<br>organism = synthetic construct | |
| SEQUENCE: 117<br>AAGIGILTV | | 9 |
| SEQ ID NO: 118<br>FEATURE<br>source | moltype = AA   length = 10<br>Location/Qualifiers<br>1..10<br>mol_type = protein<br>note = Peptide fragment<br>organism = synthetic construct | |
| SEQUENCE: 118<br>ELAGIGILTV | | 10 |
| SEQ ID NO: 119<br>FEATURE<br>source | moltype = AA   length = 9<br>Location/Qualifiers<br>1..9<br>mol_type = protein<br>note = Peptide fragment<br>organism = synthetic construct | |
| SEQUENCE: 119<br>SLLMWITQC | | 9 |
| SEQ ID NO: 120<br>FEATURE<br>source | moltype = AA   length = 9<br>Location/Qualifiers<br>1..9<br>mol_type = protein<br>note = Peptide fragment<br>organism = synthetic construct | |
| SEQUENCE: 120<br>SLLMWITQV | | 9 |
| SEQ ID NO: 121<br>FEATURE<br>source | moltype = AA   length = 9<br>Location/Qualifiers<br>1..9<br>mol_type = protein<br>note = Peptide fragment<br>organism = synthetic construct | |
| SEQUENCE: 121<br>ILKEPVHGV | | 9 |
| SEQ ID NO: 122<br>FEATURE<br>source | moltype = AA   length = 9<br>Location/Qualifiers<br>1..9<br>mol_type = protein | |

```
                       note = Peptide fragment
                       organism = synthetic construct
SEQUENCE: 122
LLFGYPVYV                                                                    9
```

The invention claimed is:

1. A polypeptide comprising an α1, α2 and α3 domain of an HLA class I molecule, a signal peptide at the N terminus and a 6×His tag joined by a GS linker at the C terminus, wherein:
   (a) the HLA class I molecule is HLA-A and comprises the α1, α2 and α3 domain of any of SEQ ID NOs. 2, 4, 6, 8, 10, and 12;
   (b) the HLA class I molecule is HLA-B and comprises the α1, α2 and α3 domain of any of SEQ ID NOs. 14, 16, 18, 20, and 22;
   (c) the HLA class I molecule is HLA-C and comprises the α1, α2 and α3 domain of any of SEQ ID NOs. 24, 26, 28, and 30; or
   (d) the polypeptide comprises the amino acid sequence set forth in SEQ ID NO: 2, 4, 6, 8, 10, 12, 14, 16, 18, 20, 22, 24, 26, 28, or 30.

2. A compound comprising the polypeptide of claim 1 complexed with a β2m domain.

3. A multimer of at least two compounds according to claim 2.

4. The multimer of claim 3, wherein an antibody recognizing the 6×His tag dimerizes the at least two compounds.

5. The polypeptide of claim 1, which is soluble.

6. The compound of claim 2, wherein the β2m domain is exogenous.

7. The polypeptide of claim 1, wherein the HLA class I molecule is HLA-A and comprises the α1, α2 and α3 domains of any of SEQ ID NOs. 2, 4, 6, 8, 10, or 12.

8. The polypeptide of claim 1, wherein the HLA class I molecule is HLA-B and comprises the α1, α2 and α3 domains of any of SEQ ID NOs. 14, 16, 18, 20, or 22.

9. The polypeptide of claim 1, wherein the HLA class I molecule is HLA-C and comprises the α1, α2 and α3 domains of any of SEQ ID NOs. 24, 26, 28, or 30.

10. The polypeptide of claim 1, wherein the α3 domain of the HLA class I molecule is the mouse $K^b$ α3 domain.

11. The polypeptide of claim 1, wherein in the α2 domain of the HLA class I molecule, Gln has been replaced with Glu at position 115.

12. The compound of claim 2, wherein the HLA class I molecule comprises the amino acid sequence set forth in SEQ ID NO. 2, 4, 6, 8, 10, 12, 14, 16, 18, 20, 22, 24, 26, 28, or 30.

13. The multimer of claim 3, wherein the multimer is a dimer, trimer, tetramer, or pentamer.

14. The compound of claim 2, wherein the HLA class I molecule is complexed to a pre-selected peptide.

15. The compound of claim 14, wherein the pre-selected peptide comprises a portion of a polypeptide selected from the group consisting of a WT1 polypeptide, a MIA polypeptide, an ALX1 polypeptide, a GAPDHS polypeptide, an S100B polypeptide, an ABC5 polypeptide, an EXTL1 polypeptide, a CPN1 polypeptide, a TSPAN10 polypeptide, a GJB1 polypeptide, an MITF polypeptide, a DUSP4 polypeptide, a cyclin-A1 polypeptide, an HERV-K-MEL polypeptide, an LAGE-1 polypeptide, a MAGE polypeptide, an LAGE-2 polypeptide, an SSX-2 polypeptide, an XAGE-1b polypeptide, a CEA polypeptide, a gp100 polypeptide, an NY-BR-1 polypeptide, a TRP-2 polypeptide, a tyrosinase polypeptide, a CD274 polypeptide, a CPSF polypeptide, a cyclin D1 polypeptide, an IDO1 polypeptide, an mdm-2 polypeptide, a p53 polypeptide, a PRAME polypeptide, a SOX10 polypeptide, a survivin polypeptide, a telomerase polypeptide, a wild-type MART1 polypeptide, a heteroclitic MART1 polypeptide, a wild-type NY-ESO-1 polypeptide, a heteroclitic NY-ESO-1 polypeptide, an HIV pol polypeptide, and an HTLV-1 tax polypeptide.

16. The compound of claim 14, wherein the pre-selected peptide comprises an amino acid sequence selected from the amino acid sequences set forth in SEQ ID NOs: 35-122.

* * * * *